(12) United States Patent
Altier et al.

(10) Patent No.: US 8,735,147 B2
(45) Date of Patent: May 27, 2014

(54) POLYNUCLEOTIDES ENCODING CYCLOTIDES HAVING NEMATOCIDAL ACTIVITY

(75) Inventors: Daniel J. Altier, Granger, IA (US); Xuehua Hu, Johnston, IA (US); Daniel L. Siehl, Menlo Park, CA (US); Jun-Zhi Wei, Palo Alto, CA (US); Gusui Wu, Grimes, IA (US)

(73) Assignee: Pioneer Hi Bred International Inc, Johnston, IA (US)

( * ) Notice: Subject to any disclaimer, the term of this patent is extended or adjusted under 35 U.S.C. 154(b) by 0 days.

(21) Appl. No.: 13/439,295

(22) Filed: Apr. 4, 2012

(65) Prior Publication Data

US 2013/0029844 A1 Jan. 31, 2013

Related U.S. Application Data

(60) Provisional application No. 61/512,948, filed on Jul. 29, 2011.

(51) Int. Cl.
*C12N 15/00* (2006.01)
*C07H 21/02* (2006.01)
*C07H 21/04* (2006.01)

(52) U.S. Cl.
USPC ...... 435/320.1; 536/23.1; 536/23.6; 536/24.1

(58) Field of Classification Search
None
See application file for complete search history.

(56) References Cited

U.S. PATENT DOCUMENTS

2005/0268354 A1* 12/2005 Herrmann et al. ............ 800/279
2012/0244575 A1* 9/2012 Poth et al. .................... 435/68.1

OTHER PUBLICATIONS

Nguyen et al., J. Biol. Chem. 286:24275-24287, May 19, 2011.*
Promega Technical Manual "pGEM®-T and pGEM®-T Easy Vector Systems", Jun. 2009, 26 pages.*
Simonsen et al., Plant Cell 17:3176-3189, Nov. 2005.*

* cited by examiner

*Primary Examiner* — David J Steadman
(74) *Attorney, Agent, or Firm* — Pioneer Hi Bred International

(57) ABSTRACT

The invention provides novel cyclotide polypeptides, and variants and fragments thereof, obtained from Butterfly pea and having pesticidal activity against nematodes. Particular embodiments of the invention provide isolated nucleic acids encoding pesticidal proteins, biopesticide compositions, expression cassettes, and transformed microorganisms and plants comprising a nucleic acid of the invention. These compositions find use in methods for controlling pests, especially plant-parasitic pests such as nematodes and insects.

8 Claims, 2 Drawing Sheets

A   B

Control 2ul extract

US 8,735,147 B2

SEQUENCE LISTING

<160> NUMBER OF SEQ ID NOS: 214

<210> SEQ ID NO 1
<211> LENGTH: 30
<212> TYPE: PRT
<213> ORGANISM: Clitoria ternatea

<400> SEQUENCE: 1

Gly Ile Pro Cys Gly Glu Ser Cys Val Phe Ile Pro Cys Ile Ser Ser
1               5                   10                  15

Val Val Gly Cys Ser Cys Lys Ser Lys Val Cys Tyr Asn Asn
            20                  25                  30

<210> SEQ ID NO 2
<211> LENGTH: 30
<212> TYPE: PRT

-continued

```
<213> ORGANISM: Clitoria ternatea

<400> SEQUENCE: 2

Gly Ile Pro Cys Gly Glu Ser Cys Val Phe Ile Pro Cys Leu Thr Thr
1               5                   10                  15

Val Val Gly Cys Ser Cys Lys Asn Lys Val Cys Tyr Asn Asn
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Degenerate CtANP-1/CtANP-2 amino acid sequence
<220> FEATURE:
<223> OTHER INFORMATION: Synthesized
<220> FEATURE:
<221> NAME/KEY: VARIANT
<222> LOCATION: 2
<223> OTHER INFORMATION: Xaa = I or V
<220> FEATURE:
<221> NAME/KEY: VARIANT
<222> LOCATION: 5
<223> OTHER INFORMATION: Xaa = G or S
<220> FEATURE:
<221> NAME/KEY: VARIANT
<222> LOCATION: 10
<223> OTHER INFORMATION: Xaa = F, Y, W or L
<220> FEATURE:
<221> NAME/KEY: VARIANT
<222> LOCATION: 14
<223> OTHER INFORMATION: Xaa = I or L
<220> FEATURE:
<221> NAME/KEY: VARIANT
<222> LOCATION: 15
<223> OTHER INFORMATION: Xaa = S or T
<220> FEATURE:
<221> NAME/KEY: VARIANT
<222> LOCATION: 16
<223> OTHER INFORMATION: Xaa = S, T, A or G
<220> FEATURE:
<221> NAME/KEY: VARIANT
<222> LOCATION: 17, 18
<223> OTHER INFORMATION: Xaa = V, I, L or A
<220> FEATURE:
<221> NAME/KEY: VARIANT
<222> LOCATION: 23
<223> OTHER INFORMATION: Xaa = K or S
<220> FEATURE:
<221> NAME/KEY: VARIANT
<222> LOCATION: 24
<223> OTHER INFORMATION: Xaa = S or N

<400> SEQUENCE: 3

Gly Xaa Pro Cys Xaa Glu Ser Cys Val Xaa Ile Pro Cys Xaa Xaa Xaa
1               5                   10                  15

Xaa Xaa Gly Cys Ser Cys Xaa Xaa Lys Val Cys Tyr Asn Asn
            20                  25                  30

<210> SEQ ID NO 4
<211> LENGTH: 119
<212> TYPE: PRT
<213> ORGANISM: Clitoria ternatea

<400> SEQUENCE: 4

Leu Leu Leu Ser Leu Ser Ser Phe Ser Leu Leu Leu Arg Leu Cys Leu
1               5                   10                  15

Gln Trp Arg Arg Leu Lys Gln Val Ser Phe Leu Ala Gly Glu Ser Cys
            20                  25                  30

Val Phe Ile Pro Cys Ile Ser Thr Val Ile Gly Cys Ser Cys Lys Asn
        35                  40                  45
```

```
Lys Val Cys Tyr Arg Asn His Val Ile Ala Ala Glu Ala Lys Thr Met
     50                  55                  60

Asp Glu His Leu Leu Leu Cys Gln Ser His Glu Asp Cys Ile Ala Lys
 65                  70                  75                  80

Gly Thr Gly Asn Phe Cys Ala Pro Phe Pro Asp Gln Asp Ile Lys Tyr
                 85                  90                  95

Gly Trp Cys Phe Arg Ala Glu Ser Glu Gly Phe Met Leu Lys Asp His
            100                 105                 110

Leu Lys Met Ser Ile Thr Asn
            115

<210> SEQ ID NO 5
<211> LENGTH: 445
<212> TYPE: DNA
<213> ORGANISM: Clitoria ternatea

<400> SEQUENCE: 5
ttgctccttt cgctgtcttc cttttccttg ctgcttcggt tatgtttgca gtggagaaga    60
ctcaagcagg tgtcattcct tgcgggagaa tcttgtgtat ttattccatg tatatcaaca   120
gttatcggct gttcttgtaa gaacaaagtt tgctatcgaa accatgttat tgcagctgag   180
gcaaagacaa tggatgagca tcttctctta tgtcaatctc atgaagattg catcgctaaa   240
ggaactggaa acttttgtgc tccttttcct gatcaagata ttaaatatgg ttggtgtttc   300
cgtgctgagt ctgaaggatt catgttgaaa gaccacttga agatgtctat caccaactga   360
aagtagtcat gcatggataa tgaatctaat actaaaaaaa tgcacatgat gcatgtacta   420
tcttaaataa atggctcttt tagta                                         445

<210> SEQ ID NO 6
<211> LENGTH: 124
<212> TYPE: PRT
<213> ORGANISM: Clitoria ternatea
<220> FEATURE:
<221> NAME/KEY: VARIANT
<222> LOCATION: 95
<223> OTHER INFORMATION: Xaa = Any Amino Acid

<400> SEQUENCE: 6

Met Ala Ser Leu Arg Ile Ala Pro Phe Ala Val Phe Leu Phe Leu Ala
  1               5                  10                  15

Ala Ser Val Met Phe Ala Val Glu Lys Thr Gln Ala Gly Val Ile Pro
             20                  25                  30

Cys Gly Glu Ser Cys Val Phe Ile Pro Cys Ile Ser Thr Val Ile Gly
         35                  40                  45

Cys Ser Cys Lys Asn Lys Val Cys Tyr Arg Asn His Val Ile Ala Ala
     50                  55                  60

Glu Ala Lys Thr Met Asp Glu His Leu Leu Leu Cys Gln Ser His Glu
 65                  70                  75                  80

Asp Cys Ile Ala Lys Gly Thr Gly Asn Phe Cys Ala Pro Phe Xaa Asp
                 85                  90                  95

Gln Asp Ile Lys Tyr Gly Trp Cys Phe Arg Ala Glu Ser Glu Gly Phe
            100                 105                 110

Met Leu Lys Asp His Leu Lys Met Ser Ile Thr Asn
            115                 120

<210> SEQ ID NO 7
<211> LENGTH: 639
<212> TYPE: DNA
```

```
<213> ORGANISM: Clitoria ternatea
<220> FEATURE:
<221> NAME/KEY: misc_feature
<222> LOCATION: 305
<223> OTHER INFORMATION: n = A,T,C or G

<400> SEQUENCE: 7
cattgcttat tttcatcaaa ttatggcttc ccttcgcatt gctcctttcg ctgtcttcct      60
tttccttgct gcttcggtta tgtttgcagt ggagaagact caagcaggtg tcattccttg     120
cggagaatct tgtgtattta ttccatgtat atcaacagtt atcggctgtt cttgtaagaa     180
caaagtttgc tatcgaaacc atgttattgc agctgaggca aagacaatgg atgagcatct     240
tctcttatgt caatctcatg aagattgcat cgctaaagga actggaaact tttgtgctcc     300
tttcnctgat caagatatta aatatggttg gtgtttccgt gctgagtctg aaggattcat     360
gttgaaagac cacttgaaga tgtctatcac caactgaaag tagtcatgca tggataatga     420
atctaatact aaaaaaaatg cacatgatgc atgtactatc ttaaataaat ggctctttta     480
gtgtctattg ttaattttta aatcttaatt gcttatgttt gtacactcta tatgtatgtt     540
gttgagcata catatataaa gtgaacaaag aataatactt tcatttcaat gttgttgcaa     600
gatgatataa gtaaaaataa aattataaat tctttaaaa                            639

<210> SEQ ID NO 8
<211> LENGTH: 119
<212> TYPE: PRT
<213> ORGANISM: Clitoria ternatea
<220> FEATURE:
<221> NAME/KEY: VARIANT
<222> LOCATION: 90, 111
<223> OTHER INFORMATION: Xaa = Any Amino Acid

<400> SEQUENCE: 8

Arg Ile Ala Pro Leu Ala Leu Phe Phe Phe Leu Ala Ala Ser Val Met
 1               5                  10                  15

Phe Thr Val Glu Lys Thr Glu Ala Gly Ile Pro Cys Gly Glu Ser Cys
            20                  25                  30

Val Phe Ile Pro Cys Ile Thr Gly Ala Ile Gly Cys Ser Cys Lys Ser
        35                  40                  45

Lys Val Cys Tyr Arg Asn His Val Ile Ala Ala Glu Ala Lys Thr Met
    50                  55                  60

Asp Asp His His Leu Leu Cys Gln Ser His Glu Asp Cys Ile Thr Lys
65                  70                  75                  80

Gly Thr Gly Asn Phe Cys Ala Pro Phe Xaa Asp Gln Asp Ile Lys Tyr
                85                  90                  95

Gly Trp Cys Phe Arg Ala Glu Ser Glu Gly Phe Met Leu Lys Xaa His
            100                 105                 110

Leu Lys Met Ser Ile Thr Asn
        115

<210> SEQ ID NO 9
<211> LENGTH: 459
<212> TYPE: DNA
<213> ORGANISM: Clitoria ternatea
<220> FEATURE:
<221> NAME/KEY: misc_feature
<222> LOCATION: 270, 335
<223> OTHER INFORMATION: n = A,T,C or G

<400> SEQUENCE: 9
ttcgcattgc tcctctcgct ctcttctttt tccttgccgc ttcggttatg tttacagtgg      60
```

```
agaagactga agccggtatc ccttgtggag aatcttgtgt atttattcca tgcataacag    120
gagccatcgg ttgttcttgt aaaagcaaag tttgctatcg aaaccatgtc attgcagctg    180
aggcaaagac aatggatgat catcatctct tatgtcaatc tcatgaagat tgcatcacta    240
aaggaactga aaacttttgt gctcctttcn ctgatcaaga tattaaatat ggttggtgtt    300
tccgtgctga gtctgaagga ttcatgttga agancactt aaagatgtct atcaccaact    360
gaaagtagtc atgtatgcat aatgaatcta ctattacaaa aagatacaca tgatgcatgt    420
actatcttaa ataaatggtt gttttaattt ctattgttg                           459

<210> SEQ ID NO 10
<211> LENGTH: 112
<212> TYPE: PRT
<213> ORGANISM: Clitoria ternatea

<400> SEQUENCE: 10

Met Ala Ser Leu Arg Ile Ala Pro Leu Ala Leu Phe Phe Phe Leu Ala
1               5                   10                  15

Ala Ser Val Met Phe Thr Val Glu Lys Thr Glu Ala Gly Ile Ser Cys
            20                  25                  30

Gly Glu Ser Cys Val Phe Ile Pro Cys Ile Thr Ala Ala Ile Gly Cys
        35                  40                  45

Ser Cys Lys Ala Lys Phe Ala Ile Glu Thr Met Ser Leu Gln Leu Arg
    50                  55                  60

Gln Arg Gln Trp Met Ile Ile Ser Tyr Val Asn Leu Met Lys Val
65                  70                  75                  80

Ala Ser Leu Lys Glu Leu Glu Thr Phe Val Leu Leu Ser Leu Ile Lys
                85                  90                  95

Ile Leu Asn Met Val Gly Val Ser Val Leu Ser Leu Lys Asp Phe Cys
            100                 105                 110

<210> SEQ ID NO 11
<211> LENGTH: 456
<212> TYPE: DNA
<213> ORGANISM: Clitoria ternatea
<220> FEATURE:
<221> NAME/KEY: misc_feature
<222> LOCATION: 282
<223> OTHER INFORMATION: n = A,T,C or G

<400> SEQUENCE: 11
ttaatggctt cccttcgcat tgctcctctc gctctcttct ttttccttgc cgcttcggtt     60
atgtttacag tggagaagac tgaagccggt atctcttgtg gagaatcttg tgtatttatt    120
ccatgcataa cagcagccat cggttgttct tgtaaagcaa agtttgctat cgaaaccatg    180
tcattgcagc tgaggcaaag acaatggatg atcatcatct cttatgtcaa tctcatgaag    240
gttgcatcac taaaggaact ggaaactttt gtgctccttt cnctgatcaa gatattaaat    300
atggttggtg tttccgtgct gagtctgaag gatttctgtt gaaagaccac ttaaagatgt    360
ctatcaccaa ctgaaagtag tcatgtatgc ataatgaatc tactattaca aaagataca    420 catgatgcat gtactatctt aaataaatgg ttgttt                              456

<210> SEQ ID NO 12
<211> LENGTH: 123
<212> TYPE: PRT
<213> ORGANISM: Clitoria ternatea

<400> SEQUENCE: 12

Met Ala Ser Leu Arg Ile Ala Pro Leu Ala Leu Phe Phe Phe Leu Ala
```

```
          1               5                  10                 15
Ala Ser Val Met Phe Thr Val Glu Lys Thr Glu Ala Gly Ile Pro Cys
                    20                 25                 30

Gly Glu Ser Cys Val Phe Ile Pro Cys Ile Thr Ala Ala Ile Gly Cys
                35                 40                 45

Ser Cys Arg Ser Lys Val Cys Tyr Arg Asn His Val Ile Ala Ala Glu
         50                 55                 60

Ala Lys Thr Met Asp Asp His His Leu Leu Cys Gln Ser His Glu Asp
 65                 70                 75                 80

Cys Ile Thr Lys Gly Thr Gly Asn Phe Cys Ala Pro Phe Pro Asp Gln
                    85                 90                 95

Asp Ile Lys Tyr Gly Trp Cys Phe Arg Ala Glu Ser Glu Gly Phe Leu
                   100                105                110

Leu Lys Asp His Leu Lys Met Ser Ile Thr Asn
                115                120

<210> SEQ ID NO 13
<211> LENGTH: 485
<212> TYPE: DNA
<213> ORGANISM: Clitoria ternatea

<400> SEQUENCE: 13
ggggaaagca tcaacttaat ccattaatgg cttcccttcg cattgctcct ctcgctctct      60 tcttttcct tgccgcttcg gttatgttta cagtggagaa gactgaagcc ggtatccctt     120
gtggagaatc ttgtgtattt attccatgca taacagcagc catcggttgt tcttgtagaa     180
gcaaagtttg ctatcgaaac catgtcattg cagctgaggc aaagacaatg gatgatcatc     240
atctcttatg tcaatctcat gaagattgca tcactaaagg aactgaaaac ttttgtgctc     300
ctttccctga tcaagatatt aaatatggtt ggtgtttccg tgctgagtct gaaggatttc     360
tgttgaaaga ccactaaaag atgtctatca ccaactgaaa gtagtcatgt atgcataatg     420
aatctactat tacaaaaaga tacacatgat gcatgtacta tcttaaataa atggttgttt     480
taatg                                                                 485

<210> SEQ ID NO 14
<211> LENGTH: 124
<212> TYPE: PRT
<213> ORGANISM: Clitoria ternatea

<400> SEQUENCE: 14

Met Ala Ser Leu Arg Ile Ala Pro Phe Ala Val Phe Leu Phe Leu Ala
  1               5                  10                 15

Ala Ser Val Met Phe Ala Val Glu Lys Thr Gln Ala Gly Val Ile Pro
                    20                 25                 30

Cys Gly Glu Ser Cys Val Phe Ile Pro Cys Ile Ser Thr Val Ile Gly
                35                 40                 45

Cys Ser Cys Lys Asn Lys Val Cys Tyr Arg Asn His Val Ile Ala Ala
         50                 55                 60

Glu Ala Lys Thr Met Asp Glu His Leu Leu Cys Gln Ser His Glu
 65                 70                 75                 80

Asp Cys Ile Ala Lys Gly Thr Gly Asn Phe Cys Ala Pro Phe Pro Asp
                    85                 90                 95

Gln Asp Ile Lys Tyr Gly Trp Cys Phe Arg Ala Glu Ser Glu Gly Phe
                   100                105                110

Met Leu Lys Asp His Leu Lys Met Ser Ile Thr Asn
                115                120
```

<210> SEQ ID NO 15
<211> LENGTH: 464
<212> TYPE: DNA
<213> ORGANISM: Clitoria ternatea

<400> SEQUENCE: 15

```
ttatggcttc ccttcgcatt gctcctttcg ctgtcttcct tttccttgct gcttcggtta      60
tgtttgcagt ggagaagact caagcaggtg tcattccttg cggagaatct tgtgtattta     120
ttccatgtat atcaacagtt atcggctgtt cttgtaagaa caaagtttgc tatcgaaacc     180
atgttattgc agctgaggca agacaatgg atgagcatct tctcttatgt caatctcatg     240
aagattgcat cgctaaagga actgaaaact tttgtgctcc tttccctgat caagatatta     300
aatatggttg gtgtttccgt gctgagtctg aaggattcat gttgaaagac cacttgaaga     360
tgtctatcac caactgaaag tagtcatgca tggataatga atctaatact aaaaaaatgt     420
acatgatgca tgtactatct aaataaatg gctcttttag tgtc                      464
```

<210> SEQ ID NO 16
<211> LENGTH: 119
<212> TYPE: PRT
<213> ORGANISM: Clitoria ternatea

<400> SEQUENCE: 16

```
Arg Ile Ala Pro Leu Ala Leu Phe Phe Phe Leu Ala Ala Ser Val Met
  1               5                  10                  15

Phe Thr Val Glu Lys Thr Glu Ala Gly Ile Pro Cys Gly Glu Ser Cys
             20                  25                  30

Val Phe Ile Pro Cys Ile Thr Ala Ala Ile Gly Cys Ser Cys Lys Ser
         35                  40                  45

Lys Val Cys Tyr Arg Asn His Val Ile Ala Ala Glu Ala Lys Thr Met
     50                  55                  60

Asp Asp His His Leu Leu Cys Gln Ser His Glu Asp Cys Ile Thr Lys
 65                  70                  75                  80

Gly Thr Gly Asn Phe Cys Ala Pro Phe Pro Asp Gln Asp Ile Lys Tyr
                 85                  90                  95

Gly Trp Cys Phe Arg Ala Glu Ser Glu Gly Phe Leu Leu Lys Asp His
            100                 105                 110

Leu Lys Met Ser Ile Thr Asn
        115
```

<210> SEQ ID NO 17
<211> LENGTH: 461
<212> TYPE: DNA
<213> ORGANISM: Clitoria ternatea

<400> SEQUENCE: 17

```
cgcattgctc ctctcgctct cttcttttc cttgccgctt cggttatgtt tacagtggag      60
aagactgaag ccggtatccc ttgtggagaa tcttgtgtat ttattccatg cataacagca     120
gccatcggtt gttcttgtaa aagcaaagtt tgctatcgaa accatgtcat tgcagctgag     180
gcaaagacaa tggatgatca tcatctctta tgtcaatctc atgaagattg catcactaaa     240 ggaactgaa acttttgtgc tccttcccct gatcaagata ttaaatatgg ttggtgtttc     300
cgtgctgagt ctgaaggatt tctgttgaaa gaccacttaa agatgtctat caccaactga     360
aagtagtcat gtatgcataa tgaatctact attacaaaaa gatacacatg atgcatgtac     420
tatcttaaat aaatggttgt tttaatttct attgttatttt t                        461
```

<210> SEQ ID NO 18
<211> LENGTH: 123
<212> TYPE: PRT
<213> ORGANISM: Clitoria ternatea
<220> FEATURE:
<221> NAME/KEY: VARIANT
<222> LOCATION: 65, 66, 107
<223> OTHER INFORMATION: Xaa = Any Amino Acid

<400> SEQUENCE: 18

```
Met Ala Ser Leu Arg Ile Ala Pro Leu Ala Leu Phe Phe Phe Leu Ala
 1               5                  10                  15

Ala Ser Val Met Phe Thr Val Glu Lys Thr Glu Ala Gly Ile Pro Cys
            20                  25                  30

Gly Glu Ser Cys Val Phe Ile Pro Cys Ile Thr Ala Ala Ile Gly Cys
        35                  40                  45

Ser Cys Lys Ser Lys Val Cys Tyr Arg Asn His Val Ile Ala Ala Glu
    50                  55                  60

Xaa Xaa Thr Met Asp Asp His His Leu Leu Cys Gln Ser His Glu Asp
65                  70                  75                  80

Cys Ile Thr Lys Gly Thr Gly Asn Phe Cys Ala Pro Phe Pro Asp Gln
                85                  90                  95

Asp Ile Lys Tyr Gly Trp Cys Phe Arg Ala Xaa Ser Glu Gly Phe Leu
            100                 105                 110

Leu Lys Asp His Leu Lys Met Ser Ile Thr Asn
        115                 120
```

<210> SEQ ID NO 19
<211> LENGTH: 475
<212> TYPE: DNA
<213> ORGANISM: Clitoria ternatea
<220> FEATURE:
<221> NAME/KEY: misc_feature
<222> LOCATION: 208, 212, 269, 335, 403, 441
<223> OTHER INFORMATION: n = A,T,C or G

<400> SEQUENCE: 19

```
aacttaatcc attaatggct tcccttcgca ttgctcctct cgctctcttc tttttccttg      60
ccgcttcggt tatgtttaca gtggagaaga ctgaagccgg tatcccttgt ggagaatctt     120
gtgtatttat tccatgcata acagcagcca tcggttgttc ttgtaaaagc aaagtttgct     180
atcgaaacca tgtcattgca gctgaggnaa anacaatgga tgatcatcat ctcttatgtc     240
aatctcatga agattgcatc actaaaggna ctggaaactt ttgtgctcct ttccctgatc     300
aagatattaa atatggttgg tgtttccgtg ctgantctga aggatttctg ttgaaagacc     360
acttaaagat gtctatcacc aactgaaagt agtcatgtat gcntaatgaa tctactatta     420
caaaaagata cacatgatgc ntgtactatc ttaaataaat ggttgtttta atttc          475
```

<210> SEQ ID NO 20
<211> LENGTH: 123
<212> TYPE: PRT
<213> ORGANISM: Clitoria ternatea
<220> FEATURE:
<221> NAME/KEY: VARIANT
<222> LOCATION: 24
<223> OTHER INFORMATION: Xaa = Any Amino Acid

<400> SEQUENCE: 20

```
Met Ala Ser Leu Arg Ile Ala Pro Leu Ala Leu Phe Phe Phe Leu Ala
 1               5                  10                  15
```

```
Ala Ser Val Met Phe Thr Val Xaa Lys Thr Glu Ala Gly Ile Pro Cys
            20                  25                  30

Gly Glu Ser Cys Val Phe Ile Pro Cys Ile Thr Ala Ala Val Gly Cys
        35                  40                  45

Ser Cys Lys Ser Lys Val Cys Tyr Arg Asn His Val Ile Ala Ala Glu
    50                  55                  60

Ala Lys Thr Met Asp Asp His His Leu Leu Cys Gln Ser His Glu Asp
65                  70                  75                  80

Cys Ile Thr Lys Gly Thr Gly Asn Phe Cys Ala Pro Phe Pro Asp Gln
                85                  90                  95

Asp Ile Lys Tyr Gly Trp Cys Phe Arg Ala Glu Ser Glu Gly Phe Leu
            100                 105                 110

Leu Lys Asp His Leu Lys Met Ser Ile Thr Asn
        115                 120

<210> SEQ ID NO 21
<211> LENGTH: 466
<212> TYPE: DNA
<213> ORGANISM: Clitoria ternatea
<220> FEATURE:
<221> NAME/KEY: misc_feature
<222> LOCATION: 73
<223> OTHER INFORMATION: n = A,T,C or G

<400> SEQUENCE: 21
ttaatggctt cccttcgcat tgctcctctc gctctcttct ttttccttgc cgcttcggtt      60
atgtttacag tgnagaagac tgaagccggt atcccttgtg agaatcttg tgtatttatt     120 ccatgcataa cagcagccgt cggttgttct tgtaaaagca aagtttgcta tcgaaaccat    180
gtcattgcag ctgaggcaaa gacaatggat gatcatcatc tcttatgtca atctcatgaa    240
gattgcatca ctaaaggaac tggaaacttt tgtgctcctt tccctgatca agatattaaa    300
tatggttggt gtttccgtgc tgagtctgaa ggatttctgt tgaaagacca cttaaagatg    360
tctatcacca actgaaagta gtcatgtatg cataatgaat ctactattac aaaaagatac    420
acatgatgca tgtactatct taaataaatg gttgttttaa tttcta                   466

<210> SEQ ID NO 22
<211> LENGTH: 126
<212> TYPE: PRT
<213> ORGANISM: Clitoria ternatea

<400> SEQUENCE: 22

Met Ala Lys Leu Val Pro Leu Ile Val Ile Phe Leu Val Ala Thr Ser
1               5                   10                  15

Val Asp Met Thr Lys Ala Ser Ile Pro Cys Gly Glu Ser Cys Val Tyr
            20                  25                  30

Ile Pro Cys Leu Thr Thr Ile Val Gly Cys Ser Cys Lys Ser Asn Val
        35                  40                  45

Cys Tyr Ser Asn His Val Ile Ala Ala Thr Ala Lys Ser Leu Asp Glu
    50                  55                  60

His Arg Leu Leu Cys Gln Ser His Glu Asp Cys Phe Lys Gly Thr
65                  70                  75                  80

Gly Asn Phe Cys Ala His Phe Pro Glu Gly Asp Val Ala Tyr Gly Trp
                85                  90                  95

Cys Phe His Ala Glu Ser Glu Gly Tyr Leu Leu Lys Asp Phe Leu Lys
            100                 105                 110

Met Pro Lys Gly Ile Val Lys Lys Pro Met Glu Ile Val Asn
        115                 120                 125
```

<210> SEQ ID NO 23
<211> LENGTH: 497
<212> TYPE: DNA
<213> ORGANISM: Clitoria ternatea

<400> SEQUENCE: 23

```
gggatagca aaacctataa caaatatcag taatcaactt agtcaaataa tggctaaact      60
tgttcctctc attgtgatct tcttggtcgc cacttctgtg gatatgacaa aagctagtat     120
accttgtgga gaatcctgtg tatacattcc atgtttaacg acaattgtcg gatgttcctg    180
taaaagcaat gtttgttata gtaaccatgt cattgctgcc actgcaaaat cattggatga    240
acatcgtctc ttatgtcaat ctcatgaaga ttgtttcgta aaaggaaccg gaaacttttg    300
tgctcatttt cccgaaggag atgttgcata tggttggtgt ttccatgctg aatctgaagg    360
atatttattg aaggactttc taaaaatgcc caaaggcatc gtgaaaaagc ctatggaaat    420
tgtcaactaa aaattatcat gcatgttgca tctatcacac ctttaattaa aataagatgc    480
atctactcct ttaaata                                                    497
```

<210> SEQ ID NO 24
<211> LENGTH: 123
<212> TYPE: PRT
<213> ORGANISM: Clitoria ternatea

<400> SEQUENCE: 24

```
Met Ala Ser Leu Arg Ile Ala Pro Leu Ala Leu Phe Phe Phe Leu Ala
  1               5                  10                  15

Ala Ser Val Met Ser Thr Val Glu Lys Thr Glu Ala Gly Ile Pro Cys
             20                  25                  30

Gly Glu Ser Cys Val Phe Ile Pro Cys Ile Thr Gly Ala Ile Gly Cys
         35                  40                  45

Ser Cys Lys Ser Lys Val Cys Tyr Arg Asn His Val Ile Ala Ala Glu
     50                  55                  60

Ala Lys Thr Met Asp Asp His His Leu Leu Cys Gln Ser His Glu Asp
 65                  70                  75                  80

Cys Ile Ile Lys Gly Thr Gly Asn Phe Cys Ala Ser Phe Pro Glu Gln
                 85                  90                  95

Asp Ile Lys Tyr Gly Trp Cys Phe Arg Ala Glu Ser Glu Gly Phe Met
            100                 105                 110

Leu Lys Asp His Leu Lys Met Ser Ile Thr Asn
        115                 120
```

<210> SEQ ID NO 25
<211> LENGTH: 454
<212> TYPE: DNA
<213> ORGANISM: Clitoria ternatea

<400> SEQUENCE: 25

```
atcaacttaa tccattaatg gcttcccttc gcattgctcc tctcgctctc ttcttttttcc    60
ttgccgcttc ggttatgtct acagtggaga agactgaagc cggtatccct gtgggagaat   120
cttgtgtatt tattccatgc ataacaggag ccatcggttg ttcttgtaaa agcaaagttt   180
gctatcgaaa ccatgtcatt gcagctgagg caaagacaat ggatgatcat catctcttgt   240
gtcaatctca tgaagattgc atcattaaag gaactggaaa cttttgtgct tctttccctg   300
aacaagatat taaatatggt tggtgttttcc gtgctgagtc tgaaggattc atgttgaaag   360
atcatttaaa gatgtctatc accaactgaa agtagtaatg tatgcataat gaatctacta   420
```

```
ttacaaaaag atacacatga tgcatgtact atct                                454
```

<210> SEQ ID NO 26
<211> LENGTH: 124
<212> TYPE: PRT
<213> ORGANISM: Clitoria ternatea

<400> SEQUENCE: 26

```
Met Ala Ser Leu Arg Ile Ala Pro Phe Ala Val Phe Leu Phe Leu Ala
1               5                   10                  15

Ala Ser Val Met Phe Ala Val Glu Lys Thr Gln Ala Gly Val Ile Pro
            20                  25                  30

Cys Gly Glu Ser Cys Val Phe Ile Pro Cys Ile Ser Thr Val Ile Gly
        35                  40                  45

Cys Ser Cys Lys Asn Lys Val Cys Tyr Arg Asn His Val Ile Ala Ala
    50                  55                  60

Glu Ala Lys Thr Met Asp Glu His Leu Leu Cys Gln Ser His Glu
65                  70                  75                  80

Asp Cys Ile Ala Lys Gly Thr Gly Asn Phe Cys Ala Pro Phe Pro Asp
                85                  90                  95

Gln Asp Ile Lys Tyr Gly Trp Cys Phe Arg Ala Glu Ser Glu Gly Phe
            100                 105                 110

Met Leu Lys Asp His Leu Lys Met Ser Ile Thr Asn
        115                 120
```

<210> SEQ ID NO 27
<211> LENGTH: 499
<212> TYPE: DNA
<213> ORGANISM: Clitoria ternatea
<220> FEATURE:
<221> NAME/KEY: misc_feature
<222> LOCATION: 33
<223> OTHER INFORMATION: n = A,T,C or G

<400> SEQUENCE: 27

```
ggggagagca aagtcattgc ttattttcat canttatggc ttcccttcgc attgctcctt    60
tcgctgtctt cctttcctt gctgcttcgg ttatgtttgc agtggagaag actcaagcag    120
gtgtcattcc ttgcggagaa tcttgtgtat ttattccatg tatatcaaca gttatcggct   180
gttcttgtaa gaacaaagtt tgctatcgaa accatgttat tgcagctgag gcaaagacaa   240
tggatgagca tcttctctta tgtcaatctc atgaagattg catcgctaaa ggaactggaa   300
acttttgtgc tcctttccct gatcaagata ttaaatatgg ttggtgtttc cgtgctgagt   360
ctgaaggatt catgttgaaa gaccacttga agatgtctat caccaactga agtagtcat   420
gcatggataa tgaatctaat actaaaaaaa tgcacatgat gcatgtacta tcttaaataa   480
atggctcttt tagtgcaga                                                499
```

<210> SEQ ID NO 28
<211> LENGTH: 123
<212> TYPE: PRT
<213> ORGANISM: Clitoria ternatea

<400> SEQUENCE: 28

```
Met Ala Ser Leu Arg Ile Ala Pro Leu Ala Leu Phe Phe Leu Ala
1               5                   10                  15

Ala Ser Val Met Phe Thr Val Glu Lys Thr Glu Ala Gly Ile Pro Cys
            20                  25                  30

Gly Glu Ser Cys Val Phe Ile Pro Cys Ile Thr Gly Ala Ile Gly Cys
```

```
                    35                  40                  45
Ser Cys Lys Ser Lys Val Cys Tyr Arg Asn His Val Ile Ala Ala Glu
 50                  55                  60

Ala Lys Thr Met Asp Asp His Leu Leu Cys Gln Ser His Glu Asp
 65                  70                  75                  80

Cys Ile Thr Lys Gly Thr Gly Asn Phe Cys Ala Ser Phe Pro Glu Gln
                     85                  90                  95

Asp Ile Lys Tyr Gly Trp Cys Phe Arg Ala Glu Ser Glu Gly Phe Met
                100                 105                 110

Leu Lys Asp His Leu Lys Met Ser Val Thr Asn
                115                 120

<210> SEQ ID NO 29
<211> LENGTH: 492
<212> TYPE: DNA
<213> ORGANISM: Clitoria ternatea
<220> FEATURE:
<221> NAME/KEY: misc_feature
<222> LOCATION: 4
<223> OTHER INFORMATION: n = A,T,C or G

<400> SEQUENCE: 29
gggncaaagc atcaacttaa tccattaatg gcttcccttc gcattgctcc tctcgctctc     60
ttctttttcc ttgccgcttc ggttatgttt acagtggaga agactgaagc cggtatccct    120
tgtggagaat cttgtgtatt tattccatgc ataacaggag ccatcggttg ttcttgtaaa    180
agcaaagttt gctatcgaaa ccatgtcatt gcagctgagg caaagacaat ggatgatcat    240
catctcttat gtcaatctca tgaagattgc atcactaaag gaactggaaa cttttgtgct    300
tcttttcctg aacaagatat taaatatggt tggtgtttcc gtgctgagtc tgaaggattc    360
atgttgaaag atcatttaaa gatgtctgtc accaactgaa agtagtcatg tatgcataat    420
gaatctacta ttacaaaaag atacacatga tgcatgtact atcttaaata aatggttgtt    480
ttaatttcta tt                                                        492

<210> SEQ ID NO 30
<211> LENGTH: 124
<212> TYPE: PRT
<213> ORGANISM: Clitoria ternatea
<220> FEATURE:
<221> NAME/KEY: VARIANT
<222> LOCATION: 41
<223> OTHER INFORMATION: Xaa = Any Amino Acid

<400> SEQUENCE: 30

Met Ala Ser Leu Arg Ile Ala Pro Phe Ala Val Phe Leu Phe Leu Ala
  1               5                  10                  15

Ala Ser Val Met Phe Ala Val Glu Lys Thr Gln Ala Gly Val Ile Pro
                 20                  25                  30

Cys Gly Glu Ser Cys Val Phe Ile Xaa Cys Ile Ser Thr Val Ile Gly
                 35                  40                  45

Cys Ser Cys Lys Asn Lys Val Cys Tyr Arg Asn His Val Ile Ala Ala
 50                  55                  60

Glu Ala Lys Thr Met Asp Glu His Leu Leu Cys Gln Ser His Glu
 65                  70                  75                  80

Asp Cys Ile Ala Lys Gly Thr Gly Asn Phe Cys Ala Pro Phe Pro Asp
                 85                  90                  95

Gln Asp Ile Lys Tyr Gly Trp Cys Phe Arg Ala Glu Ser Glu Gly Phe
                100                 105                 110
```

```
Met Leu Lys Asp His Leu Lys Met Ser Ile Thr Asn
        115                 120
```

<210> SEQ ID NO 31
<211> LENGTH: 594
<212> TYPE: DNA
<213> ORGANISM: Clitoria ternatea
<220> FEATURE:
<221> NAME/KEY: misc_feature
<222> LOCATION: 153, 549, 552
<223> OTHER INFORMATION: n = A,T,C or G

<400> SEQUENCE: 31

```
gagcaaagtc attgcttatt ttcatcaaat tatggcttcc cttcgcattg ctcctttcgc      60
tgtcttcctt ttccttgctg cttcggttat gtttgcagtg gagaagactc aagcaggtgt    120
cattccttgc ggagaatctt gtgtatttat tcnatgtata tcaacagtta tcggctgttc    180
ttgtaagaac aaagtttgct atcgaaacca tgttattgca gctgaggcaa agacaatgga    240
tgagcatctt ctcttatgtc aatctcatga agattgcatc gctaaaggaa ctggaaactt    300
ttgtgctcct ttccctgatc aagatattaa atatggttgg tgtttccgtg ctgagtctga    360
aggattcatg ttgaaagacc acttgaagat gtctatcacc aactgaaagt agtcatgcat    420
ggataatgaa tctaatacta aaaaaaatgc acatgatgca tgtactatct taaataaatg    480
gctcttttag tgtctattgt taattttttaa atcttaattg tttatgtttg tacactctat    540
atgtatgtng tngagcatac atatataaag tgaacaaaga ataatacttt catt          594
```

<210> SEQ ID NO 32
<211> LENGTH: 124
<212> TYPE: PRT
<213> ORGANISM: Clitoria ternatea

<400> SEQUENCE: 32

```
Met Ala Ser Leu Arg Ile Ala Pro Phe Ala Val Phe Leu Phe Leu Ala
  1               5                  10                  15

Ala Ser Val Met Phe Ala Val Glu Lys Thr Gln Ala Gly Val Ile Pro
             20                  25                  30

Cys Gly Glu Ser Cys Val Phe Ile Pro Cys Ile Ser Thr Val Ile Gly
         35                  40                  45

Cys Ser Cys Lys Asn Lys Val Cys Tyr Arg Asn His Val Ile Ala Ala
     50                  55                  60

Glu Ala Lys Thr Met Asp Glu His Leu Leu Leu Cys Gln Ser His Glu
 65                  70                  75                  80

Asp Cys Ile Ala Lys Gly Thr Gly Asn Phe Cys Ala Pro Phe Pro Asp
                 85                  90                  95

Gln Asp Ile Lys Tyr Gly Trp Cys Phe Arg Ala Glu Ser Glu Gly Phe
            100                 105                 110

Met Leu Lys Asp His Leu Lys Met Ser Ile Thr Asn
        115                 120
```

<210> SEQ ID NO 33
<211> LENGTH: 477
<212> TYPE: DNA
<213> ORGANISM: Clitoria ternatea

<400> SEQUENCE: 33

```
gggggcagag caaagtcatt gcttattttc atcaaattat ggcttccctt cgcattgctc      60
ctttcgctgt cttcctttc cttgctgctt cggttatgtt tgcagtggag aagactcaag    120
caggtgtcat tccttgcgga gaatcttgtg tatttattcc atgtatatca acagttatcg    180
```

```
gctgttcttg taagaacaaa gtttgctatc gaaaccatgt tattgcagct gaggcaaaga    240
caatggatga gcatcttctc ttatgtcaat ctcatgaaga ttgcatcgct aaaggaactg    300
gaaacttttg tgctcctttc cctgatcaag atattaaata tggttggtgt ttccgtgctg    360
agtctgaagg attcatgttg aaagaccact tgaagatgtc tatcaccaac tgaaagtagt    420
catgcatgga taatgaatct aatactaaaa aaatgcacat gatgcatgta ctatctt      477
```

<210> SEQ ID NO 34
<211> LENGTH: 124
<212> TYPE: PRT
<213> ORGANISM: Clitoria ternatea

<400> SEQUENCE: 34

```
Met Ala Ser Leu Arg Ile Ala Pro Phe Ala Val Phe Leu Phe Leu Ala
 1               5                  10                  15

Ala Ser Val Met Phe Ala Val Glu Lys Thr Gln Ala Gly Val Ile Pro
            20                  25                  30

Cys Gly Glu Ser Cys Val Phe Ile Pro Cys Ile Ser Thr Val Ile Gly
        35                  40                  45

Cys Ser Cys Lys Asn Lys Val Cys Tyr Arg Asn His Val Ile Ala Ala
    50                  55                  60

Glu Ala Lys Thr Met Asp Glu His Leu Leu Cys Gln Ser His Glu
65                  70                  75                  80

Asp Cys Ile Ala Lys Gly Thr Gly Asn Phe Cys Ala Pro Phe Pro Asp
                85                  90                  95

Gln Asp Ile Lys Tyr Gly Trp Cys Phe Arg Ala Glu Ser Glu Gly Phe
            100                 105                 110

Met Leu Lys Asp His Leu Lys Met Ser Ile Thr Asn
        115                 120
```

<210> SEQ ID NO 35
<211> LENGTH: 498
<212> TYPE: DNA
<213> ORGANISM: Clitoria ternatea

<400> SEQUENCE: 35

```
gggggcagag caaagtcatt gcttattttc atcaaattat ggcttccctt cgcattgctc     60
ctttcgctgt cttcctttc cttgctgctt cggttatgtt tgcagtggag aagactcaag    120
caggtgtcat tccttgcgga gaatcttgtg tatttattcc atgtatatca acagttatcg    180
gctgttcttg taagaacaaa gtttgctatc gaaaccatgt tattgcagct gaggcaaaga    240
caatggatga gcatcttctc ttatgtcaat ctcatgaaga ttgcatcgct aaaggaactg    300
gaaacttttg tgctcctttc cctgatcaag atattaaata tggttggtgt ttccgtgctg    360
agtctgaagg attcatgttg aaagaccact tgaagatgtc tatcaccaac tgaaagtagt    420
catgcatgga taatgaatct aatactaaaa aaatgcacat gatgcatgta ctatcttaaa    480
taaatggctc ttttagtg                                                  498
```

<210> SEQ ID NO 36
<211> LENGTH: 104
<212> TYPE: PRT
<213> ORGANISM: Clitoria ternatea

<400> SEQUENCE: 36

```
Met Phe Thr Val Glu Lys Thr Glu Ala Gly Ile Pro Cys Gly Glu Ser
 1               5                  10                  15
```

```
Cys Val Phe Ile Pro Cys Ile Ser Thr Val Ile Gly Cys Ser Cys Lys
             20                  25                  30
Asn Lys Val Cys Tyr Arg Asn His Val Ile Ala Ala Glu Ala Lys Thr
         35                  40                  45
Met Asp Asp His His Leu Leu Cys Gln Ser His Glu Asp Cys Ile Thr
 50                  55                  60
Lys Gly Thr Gly Asn Phe Cys Ala Pro Phe Pro Asp Gln Asp Ile Lys
 65                  70                  75                  80
Tyr Gly Trp Cys Phe Arg Ala Glu Ser Glu Gly Phe Met Leu Ile Asp
                 85                  90                  95
His Leu Lys Met Ser Ile Thr Asn
            100
```

<210> SEQ ID NO 37
<211> LENGTH: 454
<212> TYPE: DNA
<213> ORGANISM: Clitoria ternatea

<400> SEQUENCE: 37

```
tcgcattgct cctctccctc tcttcttttt ccttgccgct tcggttatgt ttacagtgga    60
gaagactgaa gccggtatcc cttgtggaga atcttgtgta tttattccat gtatatcaac   120
agttatcggc tgttcttgta agaacaaagt ttgctatcga aaccatgtta ttgcagctga   180
ggcaaagaca atggatgatc atcatctctt atgtcaatct catgaagatt gcatcactaa   240
aggaactgga aacttttgtg ctcctttccc tgatcaagac attaaatatg gttggtgttt   300
ccgtgctgag tctgaaggat tcatgttgat agaccactta aagatgtcta tcaccaactg   360
aaagtagtca tgtatgcata atgaatctac tattacgaaa agatacacat gatgcatgta   420
ctatcttaaa taaatggttg ttttaattto tatt                               454
```

<210> SEQ ID NO 38
<211> LENGTH: 123
<212> TYPE: PRT
<213> ORGANISM: Clitoria ternatea

<400> SEQUENCE: 38

```
Met Ala Ser Leu Arg Ile Ala Pro Leu Ala Leu Phe Phe Phe Leu Ala
  1               5                  10                  15
Ala Ser Val Met Phe Thr Val Glu Lys Thr Glu Ala Gly Ile Pro Cys
             20                  25                  30
Gly Glu Ser Cys Val Phe Ile Pro Cys Ile Thr Ala Ala Ile Gly Cys
         35                  40                  45
Ser Cys Lys Ser Lys Val Cys Tyr Arg Asn His Val Ile Ala Ala Glu
 50                  55                  60
Ala Lys Thr Met Asp Asp His His Leu Leu Cys Gln Ser His Glu Asp
 65                  70                  75                  80
Cys Ile Thr Lys Gly Thr Gly Asn Phe Cys Ala Pro Phe Pro Asp Gln
                 85                  90                  95
Asp Ile Lys Tyr Gly Trp Cys Phe Arg Ala Glu Ser Glu Gly Phe Leu
            100                 105                 110
Leu Lys Asp His Leu Lys Met Ser Ile Thr Asn
            115                 120
```

<210> SEQ ID NO 39
<211> LENGTH: 452
<212> TYPE: DNA
<213> ORGANISM: Clitoria ternatea

<400> SEQUENCE: 39

```
aatggcttcc cttcgcattg ctcctctcgc tctcttcttt ttccttgccg cttcggttat      60
gtttacagtg gagaagactg aagccggtat cccttgtgga gaatcttgtg tatttattcc     120
atgcataaca gcagccatcg gttgttcttg taaaagcaaa gtttgctatc gaaaccatgt     180
cattgcagct gaggcaaaga caatggatga tcatcatctc ttatgtcaat ctcatgaaga     240
ttgcatcact aaaggaactg aaacttttg tgctcctttc cctgatcaag atattaaata      300
tggttggtgt ttccgtgctg agtctgaagg atttctgttg aaagaccact taagatgtc      360
tatcaccaac tgaaagtagt catgtatgca taatgaatct actattacaa aaagatacac     420
atgatgcatg tactatctta aataaatggt tg                                   452
```

<210> SEQ ID NO 40
<211> LENGTH: 126
<212> TYPE: PRT
<213> ORGANISM: Clitoria ternatea

<400> SEQUENCE: 40

```
Met Ala Lys Leu Val Pro Leu Ile Val Ile Phe Leu Val Ala Thr Ser
 1               5                   10                  15
Val Asp Met Thr Lys Ala Ser Ile Pro Cys Gly Glu Ser Cys Val Tyr
            20                  25                  30
Ile Pro Cys Leu Thr Thr Ile Val Gly Cys Ser Cys Lys Ser Asn Val
        35                  40                  45
Cys Tyr Ser Asn His Val Ile Ala Ala Thr Ala Lys Ser Leu Asp Glu
    50                  55                  60
His Arg Leu Leu Cys Gln Ser His Glu Asp Cys Phe Val Lys Gly Thr
65                  70                  75                  80
Gly Asn Phe Cys Ala His Phe Pro Glu Gly Asp Val Ala Tyr Gly Trp
                85                  90                  95
Cys Phe His Ala Glu Ser Glu Gly Tyr Leu Leu Lys Asp Phe Leu Lys
            100                 105                 110
Met Pro Lys Gly Ile Val Lys Lys Pro Met Glu Ile Val Asn
        115                 120                 125
```

<210> SEQ ID NO 41
<211> LENGTH: 567
<212> TYPE: DNA
<213> ORGANISM: Clitoria ternatea

<400> SEQUENCE: 41

```
gggggcatag caaaacctat aacaaatatc agtaatcaac ttagtcaaat aatggctaaa      60
cttgttcctc tcattgtgat cttcttggtc gccacttctg tggatatgac aaaagctagt    120
ataccttgtg gagaatcctg tgtatacatt ccatgtttaa cgacaattgt cggatgttcc    180
tgtaaaagca atgtttgtta tagtaaccat gtcattgctg ccactgcaaa atcattggat    240
gaacatcgtc tcttatgtca atctcatgaa gattgtttcg taaaggaac cggaaacttt     300
tgtgctcatt ttcccgaagg agatgttgca tatggttggt gtttccatgc tgaatctgaa    360
ggatatttat tgaaggactt tctaaaaatg cccaaaggca tcgtgaaaaa gcctatggaa    420
attgtcaact aaaaattatc atgcatgttg catctatcac acctttaatt aaaataagat    480
gcatctactc ctttaaataa tgtcaaaagg ctcgagtgct cctctactac tgaatgtaat    540
ttacaactcc ccaaaataat atatatc                                        567
```

<210> SEQ ID NO 42

<211> LENGTH: 123
<212> TYPE: PRT
<213> ORGANISM: Clitoria ternatea

<400> SEQUENCE: 42

Met Ala Ser Leu Arg Ile Ala Pro Leu Pro Leu Phe Phe Phe Leu Ala
1               5                   10                  15

Ala Ser Val Met Phe Thr Val Glu Lys Thr Glu Ala Gly Ile Pro Cys
            20                  25                  30

Gly Glu Ser Cys Val Phe Ile Pro Cys Ile Ser Thr Val Ile Gly Cys
        35                  40                  45

Ser Cys Lys Asn Lys Val Cys Tyr Arg Asn His Val Ile Ala Ala Glu
    50                  55                  60

Ala Lys Thr Met Asp Asp His His Leu Leu Cys Gln Ser His Glu Asp
65                  70                  75                  80

Cys Ile Thr Lys Gly Thr Gly Asn Phe Cys Ala Pro Phe Pro Asp Gln
                85                  90                  95

Asp Ile Lys Tyr Gly Trp Cys Phe Arg Ala Glu Ser Glu Gly Phe Met
            100                 105                 110

Leu Lys Asp His Leu Lys Met Ser Ile Thr Asn
        115                 120

<210> SEQ ID NO 43
<211> LENGTH: 494
<212> TYPE: DNA
<213> ORGANISM: Clitoria ternatea

<400> SEQUENCE: 43
gggggcaaag catcaactta atccattaat ggcttcccct cgcattgctc ctctccctct      60
cttcttttc cttgccgctt cggttatgtt tacagtggag aagactgaag ccggtatccc     120
ttgtggagaa tcttgtgtat ttattccatg tatatcaaca gttatcggct gttcttgtaa     180
gaacaaagtt tgctatcgaa accatgttat tgcagctgag gcaaagacaa tggatgatca     240
tcatctctta tgtcaatctc atgaagatta tcatcactaa aggaactgaa acttttgtgc     300
tcctttccct gatcaagata ttaaatatgg ttggtgtttc cgtgctgagt ctgaaggatt     360
catgttgaaa gaccacttaa agatgtctat caccaactga agtagtcat gtatgcataa      420
tgaatctact attacaaaaa gatacacatg atgcatgtac tatcttaaat aaatggttgt     480
tttaatttct attg                                                        494

<210> SEQ ID NO 44
<211> LENGTH: 130
<212> TYPE: PRT
<213> ORGANISM: Clitoria ternatea

<400> SEQUENCE: 44

Met Ala Phe Ala Arg Leu Ala Val Ile Phe Phe Leu Ala Ala Ser Val
1               5                   10                  15

Met Phe Ala Met Lys Glu Thr Glu Ala Gly Val Pro Cys Gly Glu Ser
            20                  25                  30

Cys Val Phe Ile Pro Cys Thr Val Thr Ala Leu Leu Gly Cys Ser Cys
        35                  40                  45

Lys Asp Lys Val Cys Tyr Lys Asn His Val Ile Ala Ala Glu Ala Asn
    50                  55                  60

Thr Val Asp Asp His His Leu Leu Cys Gln Ser His Glu Asp Cys Phe
65                  70                  75                  80

Lys Lys Gly Ala Gly Asn Phe Cys Ala Pro Phe Leu Glu His Asp Val

```
                85                  90                  95
Lys Tyr Gly Trp Cys Phe Arg Ala Glu Ser Glu Gly Phe Leu Leu Lys
            100                 105                 110

Asp Phe Leu Lys Thr Pro Ala Asp Thr Leu Lys Met Pro Asn Ala Ile
        115                 120                 125

Thr Asn
    130

<210> SEQ ID NO 45
<211> LENGTH: 516
<212> TYPE: DNA
<213> ORGANISM: Clitoria ternatea

<400> SEQUENCE: 45
gggggtaaca attactacta ttccttgttt ccatcaacta atcaaaata tggcttttgc      60 taggcttgct gtcatattct tccttgctgc ctctgttatg tttgccatga aggagaccga    120
agctggtgtt ccatgcggag aatcttgtgt tttcattcca tgcactgtaa ctgcacttct    180 ggttgttcc tgtaaggata aagtttgtta caaaaaccat gttattgcag ctgaagcaaa    240
caccgtagat gaccatcatc ttttgtgtca atctcatgaa gactgtttca agaaaggagc    300
tggaaatttt tgtgcacctt tccttgagca tgatgttaag tatggatggt gtttccgtgc    360
tgaatctgaa ggattttgt tgaaggactt tttaaagaca ccagctgata ccttgaagat    420
gcctaatgca atcactaatt aaaaatgttg aaatgtatga tgcattctct actactctaa    480
ataaatatga atgatgcatg tactatcatg ctccgc                              516

<210> SEQ ID NO 46
<211> LENGTH: 123
<212> TYPE: PRT
<213> ORGANISM: Clitoria ternatea

<400> SEQUENCE: 46

Met Ala Ser Leu Arg Ile Ala Pro Leu Ala Leu Phe Phe Phe Leu Ala
1               5                   10                  15

Ala Ser Val Met Phe Thr Val Glu Lys Thr Glu Ala Gly Ile Pro Cys
            20                  25                  30

Gly Glu Ser Cys Val Phe Ile Pro Cys Ile Thr Ala Ala Ile Gly Cys
        35                  40                  45

Ser Cys Lys Ser Lys Val Cys Tyr Arg Asn His Val Ile Ala Ala Glu
    50                  55                  60

Ala Lys Thr Met Asp Asp His His Leu Leu Cys Gln Ser His Glu Asp
65                  70                  75                  80

Cys Ile Thr Lys Gly Thr Gly Asn Phe Cys Ala Pro Phe Pro Asp Gln
            85                  90                  95

Asp Ile Lys Tyr Gly Trp Cys Phe Arg Ala Glu Ser Glu Gly Phe Leu
        100                 105                 110

Leu Lys Asp His Leu Lys Met Ser Ile Thr Asn
    115                 120

<210> SEQ ID NO 47
<211> LENGTH: 496
<212> TYPE: DNA
<213> ORGANISM: Clitoria ternatea

<400> SEQUENCE: 47
gggggcaaag catcaactta atccattaat ggcttcccctt cgcattgctc ctctcgctct     60 cttcttttc cttgccgctt cggttatgtt tacagtggag aagactgaag ccggtatccc    120
```

-continued

```
ttgtggagaa tcttgtgtat ttattccatg cataacagca gccatcggtt gttcttgtaa      180
aagcaaagtt tgctatcgaa accatgtcat tgcagctgag gcaaagacaa tggatgatca      240
tcatctctta tgtcaatctc atgaagattg catcactaaa ggaactggaa acttttgtgc      300
tcctttccct gatcaagata ttaaatatgg ttggtgtttc cgtgctgagt ctgaaggatt      360
tctgttgaaa gaccacttaa agatgtctat caccaactga agtagtcat gtatgcataa       420 tgaatctact attacaaaaa gatacacatg atgcatgtac tatcttaaat aaatggttgt      480
tttaatttct attgcc                                                      496
```

<210> SEQ ID NO 48
<211> LENGTH: 123
<212> TYPE: PRT
<213> ORGANISM: Clitoria ternatea

<400> SEQUENCE: 48

```
Met Ala Ser Leu Arg Ile Ala Pro Leu Ala Leu Phe Phe Phe Leu Ala
  1               5                  10                  15

Ala Ser Val Met Phe Thr Val Glu Lys Thr Glu Ala Gly Ile Pro Cys
             20                  25                  30

Gly Glu Ser Cys Val Phe Ile Pro Cys Ile Thr Ala Ala Ile Gly Cys
         35                  40                  45

Ser Cys Lys Ser Lys Val Cys Tyr Arg Asn His Val Val Ala Ala Glu
     50                  55                  60

Ala Lys Thr Met Asp Asp His His Leu Leu Cys Gln Ser His Glu Asp
 65                  70                  75                  80

Cys Ile Thr Lys Gly Thr Gly Asn Phe Cys Ala Pro Phe Pro Asp Gln
                 85                  90                  95

Asp Ile Lys Tyr Gly Trp Cys Phe Arg Ala Glu Ser Glu Gly Phe Leu
            100                 105                 110

Leu Lys Asp His Leu Lys Met Ser Ile Thr Asn
        115                 120
```

<210> SEQ ID NO 49
<211> LENGTH: 497
<212> TYPE: DNA
<213> ORGANISM: Clitoria ternatea

<400> SEQUENCE: 49

```
gggggaaagc atcaacttaa tccattaatg gcttcccttc gcattgctcc tctcgctctc       60 ttcttttttcc ttgccgcttc ggttatgttt acagtggaga agactgaagc cggtatccct     120
tgtggagaat cttgtgtatt tattccatgc ataacagcag ccatcggttg ttcttgtaaa     180
agcaaagttt gctatcgaaa ccatgtcgtt gcagctgagg caaagacaat ggatgatcat     240
catctcttat gtcaatctca tgaagattgc atcactaaag gaactggaaa cttttgtgct     300
cctttccctg atcaagatat taaatatggt tggtgtttcc gtgctgagtc tgaaggattt     360
ctgttgaaag accacttaaa gatgtctatc accaactgaa gtagtcatg tatgcataat      420 gaatctacta ttacaaaaag atacacatga tgcatgtact atcttaaata aatggttgtt     480 taatttcta ttgtaac                                                      497
```

<210> SEQ ID NO 50
<211> LENGTH: 123
<212> TYPE: PRT
<213> ORGANISM: Clitoria ternatea

<400> SEQUENCE: 50

Met Ala Ser Leu Arg Ile Ala Pro Leu Ala Leu Phe Phe Leu Ala
1               5                   10                  15

Ala Ser Val Met Phe Thr Val Glu Lys Thr Glu Ala Gly Ile Pro Cys
            20                  25                  30

Gly Glu Ser Cys Val Phe Ile Pro Cys Ile Thr Ala Ile Gly Cys
            35                  40                  45

Ser Cys Lys Ser Lys Val Cys Tyr Arg Asn His Val Ile Ala Ala Glu
    50                  55                  60

Ala Lys Thr Met Asp Asp His His Leu Leu Cys Gln Ser His Glu Asp
65                  70                  75                  80

Cys Ile Thr Lys Gly Thr Gly Asn Phe Cys Ala Pro Phe Pro Asp Gln
                85                  90                  95

Asp Ile Lys Tyr Gly Trp Cys Phe Arg Ala Glu Ser Glu Gly Phe Leu
            100                 105                 110

Leu Lys Asp His Leu Lys Met Ser Ile Thr Asn
            115                 120

<210> SEQ ID NO 51
<211> LENGTH: 488
<212> TYPE: DNA
<213> ORGANISM: Clitoria ternatea

<400> SEQUENCE: 51
gggggcaaag catcaactta atccattaat ggcttcccctt cgcattgctc ctctcgctct     60
cttcttttc cttgccgctt cggttatgtt tacagtggag aagactgaag ccggtatccc     120
ttgtggagaa tcttgtgtat ttattccatg cataacagca gccatcggtt gttcttgtaa     180
aagcaaagtt tgctatcgaa accatgtcat tgcagctgag gcaaagacaa tggatgatca     240
tcatctctta tgtcaatctc atgaagattg catcactaaa ggaactggaa acttttgtgc     300
tcctttccct gatcaagata ttaaatatgg ttggtgtttc cgtgctgagt ctgaaggatt     360
tctgttgaaa gaccacttaa agatgtctat caccaactga agtagtcat gtatgcataa     420
tgaatctact attacaaaaa gatacacatg atgcatgtac tatcttaaat aaatggttgt     480
tttaattt                                                              488

<210> SEQ ID NO 52
<211> LENGTH: 123
<212> TYPE: PRT
<213> ORGANISM: Clitoria ternatea

<400> SEQUENCE: 52

Met Ala Ser Leu Arg Ile Ala Pro Leu Ala Leu Phe Phe Leu Ala
1               5                   10                  15

Ala Ser Val Met Phe Thr Val Glu Lys Thr Glu Ala Gly Ile Pro Cys
            20                  25                  30

Gly Glu Ser Cys Val Phe Ile Pro Cys Ile Thr Ala Ile Gly Cys
            35                  40                  45

Ser Cys Lys Ser Lys Val Cys Tyr Arg Asn His Val Ile Ala Ala Glu
    50                  55                  60

Ala Lys Thr Met Asp Asp His His Leu Leu Cys Gln Ser His Glu Asp
65                  70                  75                  80

Cys Ile Thr Lys Gly Thr Gly Asn Phe Cys Ala Pro Phe Pro Asp Gln
                85                  90                  95

Asp Ile Lys Tyr Gly Trp Cys Phe Arg Ala Glu Ser Glu Gly Phe Leu
            100                 105                 110

Leu Lys Asp His Leu Lys Met Ser Ile Thr Asn
        115                 120

<210> SEQ ID NO 53
<211> LENGTH: 496
<212> TYPE: DNA
<213> ORGANISM: Clitoria ternatea

<400> SEQUENCE: 53

```
gggggggcaaa gcatcaactt aatccattaa tggcttccct tcgcattgct cctctcgctc      60
tcttcttttt ccttgccgct tcggttatgt ttacagtgga gaagactgaa gccggtatcc     120
cttgtggaga atcttgtgta tttattccat gcataacagc agccatcggt tgttcttgta     180
aaagcaaagt ttgctatcga aaccatgtca ttgcagctga ggcaaagaca atggatgatc     240
atcatctctt atgtcaatct catgaagatt gcatcactaa aggaactgga aactttttgtg    300
ctcctttccc tgatcaagat attaaatatg gttggtgttt ccgtgctgag tctgaaggat     360
ttctgttgaa agaccactta agatgtctat caccaactg aaagtagtca tgtatgcata      420
atgaatctac tattacaaaa agatacacat gatgcatgta ctatcttaaa taaatggttg     480
ttttaatttc tattac                                                    496
```

<210> SEQ ID NO 54
<211> LENGTH: 125
<212> TYPE: PRT
<213> ORGANISM: Clitoria ternatea

<400> SEQUENCE: 54

Met Ala Tyr Val Arg Leu Thr Pro Leu Ala Val Ile Phe Phe Leu Ala
 1               5                  10                  15

Thr Ser Val Met Phe Ala Val Lys Thr Glu Ala Gly Thr Val Pro Cys
            20                  25                  30

Gly Glu Ser Cys Val Phe Ile Pro Cys Ile Thr Gly Ile Ala Gly Cys
        35                  40                  45

Ser Cys Lys Asn Lys Val Cys Tyr Leu Asn His Val Ile Ala Ala Glu
    50                  55                  60

Ala Lys Thr Met Asp Glu His His Leu Leu Cys Gln Ser His Glu Asp
65                  70                  75                  80

Cys Ile Lys Lys Gly Thr Gly Asn Phe Cys Ala Pro Phe Leu Glu His
                85                  90                  95

Asn Val Asn Tyr Gly Trp Cys Phe Asn Ala Gln Ser Glu Gly Tyr Leu
            100                 105                 110

Leu Lys Asp Phe Leu Lys Ile Pro Lys Thr Ile Thr Asn
        115                 120                 125

<210> SEQ ID NO 55
<211> LENGTH: 541
<212> TYPE: DNA
<213> ORGANISM: Clitoria ternatea

<400> SEQUENCE: 55

```
ggggacaaca aatattagta attggttatt ttgatcaact aaatccaacc atggcttatg      60
ttaggcttac tcccctcgct gtcatcttct tccttgccac ttctgttatg tttgcagtaa     120
agacagaagc tggtactgtc ccttgtggag aatcttgtgt atttatccca tgtataactg     180
ggattgctgg ttgttcttgt aagaacaaag tttgttatct aaaccatgtt attgccgctg     240
aagcaaagac catggatgaa caccatcttt tgtgccaatc ccatgaagat tgcattaaaa     300
agggaactgg aaactttttgc gctccttttc ttgaacataa tgttaactat ggctggtgtt    360
```

```
ttaatgctca atcagaagga tatttgttga aagatttctt aaagatacct aagcacaatca      420 ctaactaaaa atgctatgca tgatgtacgg tatcagttta aataaaatct tatgatgccc      480
ctaccatgtt ttgtggagga tcaagtgttc ctgtactagt taatgtactt ttctatttca      540
t                                                                      541
```

<210> SEQ ID NO 56
<211> LENGTH: 123
<212> TYPE: PRT
<213> ORGANISM: Clitoria ternatea

<400> SEQUENCE: 56

```
Met Ala Ser Leu Arg Ile Ala Pro Leu Ala Leu Phe Phe Phe Leu Ala
 1               5                  10                  15

Ala Ser Val Met Phe Thr Val Glu Lys Thr Glu Ala Gly Ile Pro Cys
                20                  25                  30

Gly Glu Ser Cys Val Phe Ile Pro Cys Ile Thr Ala Ala Ile Gly Cys
            35                  40                  45

Ser Cys Lys Ser Lys Val Cys Tyr Arg Asn His Val Ile Ala Ala Glu
        50                  55                  60

Ala Lys Thr Met Asp Asp His His Leu Leu Cys Gln Ser His Glu Asp
65                  70                  75                  80

Cys Ile Thr Lys Gly Thr Gly Asn Phe Cys Ala Pro Phe Pro Asp Gln
                85                  90                  95

Asp Ile Lys Tyr Gly Trp Cys Phe Arg Ala Glu Ser Glu Gly Phe Leu
            100                 105                 110

Leu Lys Asp His Leu Lys Met Ser Ile Thr Asn
        115                 120
```

<210> SEQ ID NO 57
<211> LENGTH: 500
<212> TYPE: DNA
<213> ORGANISM: Clitoria ternatea

<400> SEQUENCE: 57

```
ggggaaaagc atcaacttaa tccattaatg cttcccttc gcattgctcc tctcgctctc       60 ttcttttcc ttgccgcttc ggttatgttt acagtggaga agactgaagc cggtatccct      120
tgtggagaat cttgtgtatt tattccatgc ataacagcag ccatcggttg ttcttgtaaa      180
agcaaagttt gctatcgaaa ccatgtcatt gcagctgagg caaagacaat ggatgatcat      240
catctcttat gtcaatctca tgaagattgc atcactaaag gaactggaaa cttttgtgct      300
cctttccctg atcaagatat taaatatggt tggtgtttcc gtgctgagtc tgaaggattt      360
ctgttgaaag accacttaaa gatgtctatc accaactgaa agtagtcatg tatgcataat      420
gaatctacta ttacaaaaag atacacatga tgcatgtact atcttaaata aatggttgtt      480
ttaatttcta ttgttatttt                                                  500
```

<210> SEQ ID NO 58
<211> LENGTH: 136
<212> TYPE: PRT
<213> ORGANISM: Clitoria ternatea

<400> SEQUENCE: 58

```
Met Gln Ser Lys Val Ile Ala Tyr Phe His Gln Ile Met Ala Ser Leu
 1               5                  10                  15

Arg Ile Ala Pro Phe Ala Val Phe Leu Phe Leu Ala Ala Ser Val Met
                20                  25                  30
```

```
Phe Ala Val Glu Lys Thr Gln Ala Gly Val Ile Pro Cys Gly Glu Ser
         35                  40                  45

Cys Val Phe Ile Pro Cys Ile Ser Thr Val Ile Gly Cys Ser Cys Lys
 50                  55                  60

Asn Lys Val Cys Tyr Arg Asn His Val Ile Ala Glu Ala Lys Thr
 65                  70                  75                  80

Met Asp Glu His Leu Leu Cys Gln Ser His Glu Asp Cys Ile Ala
                 85                  90                  95

Lys Gly Thr Gly Asn Phe Cys Ala Pro Phe Pro Asp Gln Asp Ile Lys
                100                 105                 110

Tyr Gly Trp Cys Phe Arg Ala Glu Ser Glu Gly Phe Met Leu Lys Asp
                115                 120                 125

His Leu Lys Met Ser Ile Thr Asn
                130             135
```

<210> SEQ ID NO 59
<211> LENGTH: 605
<212> TYPE: DNA
<213> ORGANISM: Clitoria ternatea

<400> SEQUENCE: 59

```
ggggatggaa gaaggaagta atgcagagca aagtcattgc ttattttcat caaattatgg      60
cttcccttcg cattgctcct ttcgctgtct tccttttcct tgctgcttcg gttatgtttg     120
cagtggagaa gactcaagca ggtgtcattc cttgcggaga atcttgtgta tttattccat     180
gtatatcaac agttatcggc tgttcttgta agaacaaagt ttgctatcga aaccatgtta     240
ttgcagctga ggcaaagaca atggatgagc atcttctctt atgtcaatct catgaagatt     300
gcatcgctaa aggaactgga aacttttgtg ctccttttccc tgatcaagat attaaatatg     360
gttggtgttt ccgtgctgag tctgaaggat tcatgttgaa agaccacttg aagatgtcta     420
tcaccaactg aaagtagtca tgcatggata atgaatctaa actaaaaaaa atgcacatga     480
tgcatgtact atcttaaata aatggctctt ttagtgtcta tgttaatttt ttaaatctta     540
attgcttatg tttgtacact ctatatgtat gttgctgagc atacatatat aaagtgaaca     600
aagaa                                                                 605
```

<210> SEQ ID NO 60
<211> LENGTH: 123
<212> TYPE: PRT
<213> ORGANISM: Clitoria ternatea

<400> SEQUENCE: 60

```
Met Ala Ser Leu Arg Ile Ala Pro Leu Ala Leu Phe Phe Phe Leu Ala
  1               5                  10                  15

Ala Ser Val Met Phe Thr Val Glu Lys Thr Glu Ala Gly Ile Pro Cys
             20                  25                  30

Gly Glu Ser Cys Val Phe Ile Pro Cys Ile Thr Ala Ala Ile Gly Cys
             35                  40                  45

Ser Cys Lys Ser Lys Val Cys Tyr Arg Asn His Val Ile Ala Ala Glu
 50                  55                  60

Ala Lys Thr Met Asp Asp His Leu Leu Cys Gln Ser His Glu Asp
 65                  70                  75                  80

Cys Ile Thr Lys Gly Thr Gly Asn Phe Cys Ala Pro Phe Pro Asp Gln
                 85                  90                  95

Asp Ile Lys Tyr Gly Trp Cys Phe Arg Ala Glu Ser Glu Gly Phe Leu
                100                 105                 110
```

Leu Lys Asp His Leu Lys Met Ser Ile Thr Asn
        115                 120

<210> SEQ ID NO 61
<211> LENGTH: 466
<212> TYPE: DNA
<213> ORGANISM: Clitoria ternatea

<400> SEQUENCE: 61

```
gggggcaaag catcaactta atccattaat ggcttcccct cgcattgctc ctctcgctct      60
cttcttttc cttgccgctt cggttatgtt tacagtggag aagactgaag ccggtatccc     120
ttgtggagaa tcttgtgtat ttattccatg cataacagca gccatcggtt gttcttgtaa     180
aagcaaagtt tgctatcgaa accatgtcat tgcagctgag gcaaagacaa tggatgatca     240
tcatctctta tgtcaatctc atgaagattg catcactaaa ggaactggaa acttttgtgc     300
tcctttccct gatcaagata ttaaatatgg ttggtgtttc cgtgctgagt ctgaaggatt     360
tctgttgaaa gaccacttaa agatgtctat caccaactga aagtagtcat gtatgcataa     420
tgaatctact attacaaaaa gatacacatg atgcatgtac tatcct                    466
```

<210> SEQ ID NO 62
<211> LENGTH: 123
<212> TYPE: PRT
<213> ORGANISM: Clitoria ternatea

<400> SEQUENCE: 62

Met Ala Ser Leu Arg Ile Ala Pro Leu Ala Leu Phe Phe Phe Leu Ala
 1               5                  10                  15

Ala Ser Val Met Phe Thr Val Glu Lys Thr Glu Ala Gly Ile Pro Cys
            20                  25                  30

Gly Glu Ser Cys Val Phe Ile Pro Cys Ile Thr Ala Ala Ile Gly Cys
        35                  40                  45

Ser Cys Lys Ser Lys Val Cys Tyr Arg Asn His Val Ile Ala Ala Glu
    50                  55                  60

Ala Lys Thr Met Asp Asp His His Leu Leu Cys Gln Ser His Glu Asp
65                  70                  75                  80

Cys Ile Thr Lys Gly Thr Gly Asn Phe Cys Ala Pro Phe Pro Asp Gln
                85                  90                  95

Asp Ile Lys Tyr Gly Trp Cys Phe Arg Ala Glu Ser Glu Gly Phe Leu
            100                 105                 110

Leu Lys Asp His Leu Lys Met Ser Ile Thr Asn
        115                 120

<210> SEQ ID NO 63
<211> LENGTH: 496
<212> TYPE: DNA
<213> ORGANISM: Clitoria ternatea

<400> SEQUENCE: 63

```
gggggcaaag catcaactta atccattaat ggcttcccct cgcattgctc ctctcgctct      60
cttcttttc cttgccgctt cggttatgtt tacagtggag aagactgaag ccggtatccc     120
ttgtggagaa tcttgtgtat ttattccatg cataacagca gccatcggtt gttcttgtaa     180
aagcaaagtt tgctatcgaa accatgtcat tgcagctgag gcaaagacaa tggacgatca     240
tcatctctta tgtcaatctc atgaagattg catcactaaa ggaactggaa acttttgtgc     300
tcctttccct gatcaagata ttaaatatgg ttggtgtttc cgtgctgagt ctgaaggatt     360
```

```
tctgttgaaa gaccacttaa agatgtctat caccaactga aagtagtcat gtatgcataa     420
tgaatctact attacaaaaa gatacacatg atgcatgtac tatcttaaat aaatggttgt     480
tttaatttct attgtt                                                     496
```

<210> SEQ ID NO 64
<211> LENGTH: 124
<212> TYPE: PRT
<213> ORGANISM: Clitoria ternatea

<400> SEQUENCE: 64

```
Met Ala Ser Leu Arg Ile Ala Pro Phe Ala Val Phe Leu Phe Leu Ala
 1               5                  10                  15

Ala Ser Val Met Phe Ala Val Glu Lys Thr Gln Ala Gly Val Ile Pro
            20                  25                  30

Cys Gly Glu Ser Cys Val Phe Ile Pro Cys Ile Ser Thr Val Ile Gly
        35                  40                  45

Cys Ser Cys Lys Asn Lys Val Cys Tyr Arg Asn His Val Ile Ala Ala
    50                  55                  60

Glu Ala Lys Thr Met Asp Glu His Leu Leu Cys Gln Ser His Glu
65                  70                  75                  80

Asp Cys Ile Ala Lys Gly Thr Gly Asn Phe Cys Ala Pro Phe Pro Asp
                85                  90                  95

Gln Asp Ile Lys Tyr Gly Trp Cys Phe Arg Ala Glu Ser Glu Gly Phe
            100                 105                 110

Met Leu Lys Asp His Leu Lys Met Ser Ile Thr Asn
        115                 120
```

<210> SEQ ID NO 65
<211> LENGTH: 588
<212> TYPE: DNA
<213> ORGANISM: Clitoria ternatea

<400> SEQUENCE: 65

```
gggggcagag caaagtcatt gcttattttc atcaaattat ggcttccctt cgcattgctc      60 cttcgctgt cttcctttc cttgctgctt cggttatgtt tgcagtggag aagactcaag     120
caggtgtcat tccttgcgga gaatcttgtg tatttattcc atgtatatca acagttatcg     180
gctgttcttg taagaacaaa gtttgctatc gaaaccatgt tattgcagct gaggcaaaga     240
caatggatga gcatcttctc ttatgtcaat ctcatgaaga ttgcatcgct aaaggaactg     300 gaaactttg tgctccttc cctgatcaag atattaaata tggttggtgt ttccgtgctg     360
agtctgaagg attcatgttg aaagaccact tgaagatgtc tatcaccaac tgaaagtagt     420
catgcatgga taatgaatct aatactaaaa aaatgcaca tgatgcatgt actatcttaa     480
ataaatggct cttttagtgt ctattgttaa tttttaaatc ttaattgctt atgtttgtac     540
actctatatg tatgttgttg agcatacata tataaagtga acaaagaa                 588
```

<210> SEQ ID NO 66
<211> LENGTH: 123
<212> TYPE: PRT
<213> ORGANISM: Clitoria ternatea

<400> SEQUENCE: 66

```
Met Ala Ser Leu Arg Ile Ala Pro Leu Pro Leu Phe Phe Phe Leu Ala
 1               5                  10                  15

Ala Ser Val Met Phe Thr Val Glu Lys Thr Glu Ala Gly Ile Pro Cys
            20                  25                  30
```

```
Gly Glu Ser Cys Val Phe Ile Pro Cys Ile Ser Thr Val Ile Gly Cys
            35                  40                  45

Ser Cys Lys Asn Lys Val Cys Tyr Arg Asn His Val Ile Ala Ala Glu
 50                  55                  60

Ala Lys Thr Met Asp Asp His His Leu Leu Cys Gln Ser His Glu Asp
 65                  70                  75                  80

Cys Ile Thr Lys Gly Thr Gly Asn Phe Cys Ala Pro Phe Pro Asp Gln
                     85                  90                  95

Asp Ile Lys Tyr Gly Trp Cys Phe Arg Ala Glu Ser Glu Gly Phe Met
                100                 105                 110

Leu Lys Asp His Leu Lys Met Ser Ile Thr Asn
            115                 120
```

<210> SEQ ID NO 67
<211> LENGTH: 502
<212> TYPE: DNA
<213> ORGANISM: Clitoria ternatea

<400> SEQUENCE: 67

```
ggggaaaagc atcaacttaa tccattaatg gcttcccttc gcattgctcc tctccctctc    60
ttcttttttcc ttgccgcttc ggttatgttt acagtggaga agactgaagc cggtatccct   120
tgtggagaat cttgtgtatt tattccatgt atatcaacag ttatcggctg ttcttgtaag   180
aacaaagttt gctatcgaaa ccatgttatt gcagctgagg caaagacaat ggatgatcat   240
catctcttat gtcaatctca tgaagattgc atcactaaag gaactgggaa ctttgtgct   300
cctttccctg atcaagatat taaatatggt tggtgtttcc gtgctgagtc tgaaggattc   360
atgttgaaag accacttaaa gatgtctatc accaactgaa agtagtcatg tatgcataat   420
gaatctacta ttacaaaaag atacacatga tgcatgtact atcttaaata aatggttgtt   480
ttaatttcta ttgttatttt cc                                             502
```

<210> SEQ ID NO 68
<211> LENGTH: 123
<212> TYPE: PRT
<213> ORGANISM: Clitoria ternatea

<400> SEQUENCE: 68

```
Met Ala Ser Leu Arg Ile Ala Pro Leu Ala Leu Phe Phe Phe Leu Ala
 1               5                  10                  15

Ala Ser Val Met Phe Thr Val Glu Lys Thr Glu Ala Gly Ile Pro Cys
             20                  25                  30

Gly Glu Ser Cys Val Phe Ile Pro Cys Ile Thr Gly Ala Ile Gly Cys
            35                  40                  45

Ser Cys Lys Ser Lys Val Cys Tyr Arg Asn His Val Ile Ala Ala Glu
 50                  55                  60

Ala Lys Thr Met Asp Asp His His Leu Leu Cys Gln Ser His Glu Asp
 65                  70                  75                  80

Cys Ile Ile Lys Gly Thr Gly Asn Phe Cys Ala Ser Phe Pro Glu Gln
                     85                  90                  95

Asp Ile Lys Tyr Gly Trp Cys Phe Arg Ala Glu Ser Glu Gly Phe Met
                100                 105                 110

Leu Lys Asp His Leu Lys Met Ser Ile Thr Asn
            115                 120
```

<210> SEQ ID NO 69
<211> LENGTH: 496
<212> TYPE: DNA

```
<213> ORGANISM: Clitoria ternatea

<400> SEQUENCE: 69
gggggcaaag catcaactta atccattaat ggcttcccctt cgcattgctc ctctcgctct      60
cttcttttc cttgccgctt cggttatgtt tacagtggag aagactgaag ccggtatccc      120
ttgtggagaa tcttgtgtat ttattccatg cataacagga gccatcggtt gttcttgtaa      180
aagcaaagtt tgctatcgaa accatgtcat tgcagctgag gcaaagacaa tggatgatca      240
tcatctcttg tgtcaatctc atgaagattg catcattaaa ggaactggaa acttttgtgc      300
ttctttccct gaacaagata ttaaaatatgg ttggtgtttc cgtgctgagt ctgaaggatt      360
catgttgaaa gatcatttaa agatgtctat caccaactga agtagtaat gtatgcataa      420
tgaatctact attacaaaaa gatacacatg atgcatgtac tatcttaaat aaatggttgt      480
ttcaattttt attgtt                                                    496

<210> SEQ ID NO 70
<211> LENGTH: 123
<212> TYPE: PRT
<213> ORGANISM: Clitoria ternatea

<400> SEQUENCE: 70

Met Ala Ser Leu Arg Ile Ala Pro Leu Ala Leu Phe Phe Phe Leu Ala
 1               5                  10                  15

Ala Ser Val Met Phe Thr Val Glu Lys Thr Glu Ala Gly Ile Pro Cys
             20                  25                  30

Gly Glu Ser Cys Val Phe Ile Pro Cys Ile Thr Gly Ala Ile Gly Cys
         35                  40                  45

Ser Cys Lys Ser Arg Val Cys Tyr Arg Asn His Val Ile Ala Ala Glu
     50                  55                  60

Ala Lys Thr Met Asp Asp His His Leu Leu Cys Gln Ser His Glu Asp
 65                  70                  75                  80

Cys Ile Thr Lys Gly Thr Gly Asn Phe Cys Ala Ser Phe Pro Glu Gln
                 85                  90                  95

Asp Ile Lys Tyr Gly Trp Cys Phe Arg Ala Glu Ser Glu Gly Phe Met
            100                 105                 110

Leu Lys Asp His Leu Lys Met Ser Val Thr Asn
        115                 120

<210> SEQ ID NO 71
<211> LENGTH: 494
<212> TYPE: DNA
<213> ORGANISM: Clitoria ternatea

<400> SEQUENCE: 71
ggggaaagca tcaacttaat ccattaatgg cttcccttcg cattgctcct ctcgctctct      60
tcttttcct tgccgcttcg gttatgttta cagtggagaa gactgaagcc ggtatccctt      120
gtggagaatc ttgtgtattt attccatgca taacaggagc catcggttgt tcttgtaaaa      180
gcagagtttg ctatcgaaac catgtcattg cagctgaggc aaagacaatg gatgatcatc      240
atctcttatg tcaatctcat gaagattgca tcactaaagg aactggaaac ttttgtgctt      300
cttttcctga acaagatatt aaatatggtt ggtgtttccg tgctgagtct gaaggattca      360
tgttgaaaga tcatttaaag atgtctgtca ccaactgaaa gtagtcatgt atgcataatg      420
aatctactat tacaaaaaga tacacatgat gcatgtacta tcttaaataa atggttgttt      480
taatttctat tgtc                                                      494
```

<210> SEQ ID NO 72
<211> LENGTH: 123
<212> TYPE: PRT
<213> ORGANISM: Clitoria ternatea

<400> SEQUENCE: 72

Met Ala Tyr Leu Arg Leu Ala Ala Leu Ala Val Ile Phe Leu Leu Ala
1               5                   10                  15

Thr Thr Val Lys Lys Thr Gly Ala Ala Arg Ile Pro Cys Gly Glu Ser
            20                  25                  30

Cys Val Trp Ile Pro Cys Thr Ile Thr Ala Leu Val Gly Cys Ala Cys
        35                  40                  45

His Glu Lys Val Cys Tyr Lys Ser Ser Ser Ile Ala Ser Thr Ala Lys
    50                  55                  60

Thr Met Asp Glu His His Asn Leu Cys Gln Ser His Glu Asp Cys Ile
65                  70                  75                  80

Ile Lys Gly Ser Gly Asn Phe Cys Ala Ser Phe Pro Asn Arg Asp Ile
                85                  90                  95

Val Tyr Gly Trp Cys Phe Tyr Val Gln Ser Glu Gly Phe Leu Leu Lys
            100                 105                 110

Asp Phe Leu Lys Met Pro Met Ala Ile Thr Asn
            115                 120

<210> SEQ ID NO 73
<211> LENGTH: 603
<212> TYPE: DNA
<213> ORGANISM: Clitoria ternatea

<400> SEQUENCE: 73
ggggagagca taaccttcaa cgaatatcag ttactagtga tggcctatct taggcttgct      60
gctttagctg tgatcttctt gcttgccact actgtgaaga aaacaggagc tgctcgtatt    120
ccttgtggag aatcttgtgt atggattcca tgtactataa cagcgcttgt tggttgtgca    180
tgccatgaga aagtttgcta taagtcctct agcattgcat ctactgcaaa gacaatggat    240
gaacatcaca acttatgtca atctcatgag gattgcatca taaaaggaag tggaaatttt    300
tgcgcttctt ttcctaatcg tgatattgtt tatggttggt gttttttatgt tcaatctgaa    360
ggattttttgt taaagacttt cttgaaaatg cctatggcaa tcactaatta aaaattgtca    420
tgcatgaagc atgattacta ctatgaataa aaacttttga tgtatctact accttaagta    480
aaggactaag tgcttctcta atgtcctttg tttctgataa atcttaaatg tgtacgacat    540
atatgtacaa gacatgtatg cttttgagct cgtatataag tgaataaagg ataataatta    600
cat                                                                  603

<210> SEQ ID NO 74
<211> LENGTH: 126
<212> TYPE: PRT
<213> ORGANISM: Clitoria ternatea

<400> SEQUENCE: 74

Met Ala Lys Leu Val Pro Leu Ile Val Ile Phe Leu Val Ala Thr Ser
1               5                   10                  15

Val Asp Met Thr Lys Ala Ser Ile Pro Cys Gly Glu Ser Cys Val Tyr
            20                  25                  30

Ile Pro Cys Leu Thr Thr Ile Val Gly Cys Ser Cys Lys Ser Asn Val
        35                  40                  45

Cys Tyr Ser Asn His Val Ile Ala Ala Thr Ala Lys Ser Leu Asp Glu

```
                50                  55                  60
His Arg Leu Leu Cys Gln Ser His Glu Asp Cys Phe Val Lys Gly Thr
 65                  70                  75                  80

Gly Asn Phe Cys Ala His Phe Pro Gly Asp Val Ala Tyr Gly Trp
                 85                  90                  95

Cys Phe His Ala Glu Ser Glu Gly Tyr Leu Leu Lys Asp Ile Leu Lys
                    100                 105                 110

Met Pro Lys Gly Ile Val Lys Lys Pro Met Glu Ile Val Asn
                115                 120                 125

<210> SEQ ID NO 75
<211> LENGTH: 578
<212> TYPE: DNA
<213> ORGANISM: Clitoria ternatea

<400> SEQUENCE: 75 ggggcatag caaaacctat aacaaatatc agtaatcaac ttagtcaaat aatggctaaa      60
cttgttcctc tcattgtgat cttcttggtc gccacttctg tggatatgac aaaagctagt     120
ataccttgtg agaatcctg tgtatacatt ccatgtttaa cgacaattgt cggatgttcc     180
tgtaaaagca atgtttgtta tagtaaccat gtcattgctg ccactgcaaa atcattggat     240
gaacatcgtc tcttatgtca atctcatgaa gattgtttcg taaaaggaac cggaaacttt     300
tgtgctcatt ttcccgaagg agatgttgca tatggttggt gtttccatgc tgaatctgaa     360
ggatatttat tgaaggacat tctaaaaatg cccaaaggca tcgtgaaaaa gcctatggaa     420
attgtcaact aaaaattatc atgcatgttg catctattac acctttaatt aaaataagat     480
gcatctactc ctttaaataa tgtcaaaagg ctcgagtgct cctctactac tgaatgtaat     540
ttacaactcc ccaaaataat atatatcaat ttggagag                             578

<210> SEQ ID NO 76
<211> LENGTH: 123
<212> TYPE: PRT
<213> ORGANISM: Clitoria ternatea

<400> SEQUENCE: 76

Met Ala Ser Leu Arg Ile Ala Pro Leu Pro Leu Phe Phe Phe Leu Ala
 1               5                  10                  15

Ala Ser Val Met Phe Thr Val Glu Lys Thr Glu Ala Gly Ile Pro Cys
                20                  25                  30

Gly Glu Ser Cys Val Phe Ile Pro Cys Ile Ser Ala Val Ile Gly Cys
                35                  40                  45

Ser Cys Lys Asn Lys Val Cys Tyr Arg Asn His Val Ile Ala Ala Glu
 50                  55                  60

Ala Lys Thr Met Asp Asp His His Leu Leu Cys Gln Ser His Glu Asp
 65                  70                  75                  80

Cys Ile Thr Lys Gly Thr Gly Asn Phe Cys Ala Pro Phe Pro Asp Gln
                 85                  90                  95

Asp Ile Lys Tyr Gly Trp Cys Phe Arg Ala Glu Ser Glu Gly Phe Met
                    100                 105                 110

Leu Lys Asp His Leu Lys Met Ser Ile Thr Asn
                115                 120

<210> SEQ ID NO 77
<211> LENGTH: 506
<212> TYPE: DNA
<213> ORGANISM: Clitoria ternatea
```

<400> SEQUENCE: 77

```
gggggcaaag catcaactta atccattaat ggcttccctt cgcattgctc ctctccctct    60
cttcttttc cttgccgctt cggttatgtt tacagtggag aagactgaag ccggtatccc   120
ttgtggagaa tcttgtgtat ttattccatg tatatcagca gttatcggct gttcttgtaa   180
gaacaaagtt tgctatcgaa accatgttat tgcagctgag gcaaagacaa tggatgatca   240
tcatctctta tgtcaatctc atgaagattg catcactaaa ggaactggaa acttttgtgc   300
tcctttccct gatcaagata ttaaatatgg ttggtgtttc cgtgctgagt ctgaaggatt   360
catgttgaaa gaccacttaa agatgtctat caccaactga agtagtcat gtatgcataa   420
tgaatctact attacaaaaa gatacacatg atgcatgtac tatcttaaat aaatggttgt   480
tttaatttct attgttattt tttagc                                       506
```

<210> SEQ ID NO 78
<211> LENGTH: 123
<212> TYPE: PRT
<213> ORGANISM: Clitoria ternatea

<400> SEQUENCE: 78

```
Met Ala Ser Leu Arg Ile Ala Pro Leu Ala Leu Phe Phe Phe Leu Ala
  1               5                  10                  15
Ala Ser Val Met Phe Thr Val Glu Lys Thr Glu Ala Gly Ile Pro Cys
             20                  25                  30
Gly Glu Ser Cys Val Phe Ile Pro Cys Ile Thr Ala Ala Ile Gly Cys
         35                  40                  45
Ser Cys Lys Ser Lys Val Cys Tyr Arg Asn His Val Ile Ala Ala Glu
     50                  55                  60
Ala Lys Thr Met Asp Asp His His Leu Leu Cys Gln Ser His Glu Asp
 65                  70                  75                  80
Cys Ile Thr Lys Gly Thr Gly Asn Phe Cys Ala Pro Phe Pro Asp Gln
                 85                  90                  95
Asp Ile Lys Tyr Gly Trp Cys Phe Arg Ala Glu Ser Val Gly Phe Leu
                100                 105                 110
Leu Lys Asp His Leu Lys Met Ser Ile Thr Asn
            115                 120
```

<210> SEQ ID NO 79
<211> LENGTH: 484
<212> TYPE: DNA
<213> ORGANISM: Clitoria ternatea

<400> SEQUENCE: 79

```
gggggcaaag catcaactta atccattaat ggcttccctt cgcattgctc ctctcgctct    60
cttcttttc cttgccgctt cggttatgtt tacagtggag aagactgaag ccggtatccc   120
ttgtggagaa tcttgtgtat ttattccatg cataacagca gccatcggtt gttcttgtaa   180
aagcaaagtt tgctatcgaa accatgtcat tgcagctgag gcaaagacaa tggatgatca   240
tcatctctta tgtcaatctc atgaagattg catcactaaa ggaactggaa acttttgtgc   300
tcctttccct gatcaagata ttaaatatgg ttggtgtttc cgtgctgagt ctgtaggatt   360
tctgttgaaa gaccacttaa agatgtctat caccaactga agtagtcat gtatgcataa   420
tgaatctact attacaaaaa gatacacatg atgcatgtac tatcttaaat aaatggttgt   480
ttta                                                               484
```

<210> SEQ ID NO 80

-continued

```
<211> LENGTH: 123
<212> TYPE: PRT
<213> ORGANISM: Clitoria ternatea

<400> SEQUENCE: 80

Met Ala Ser Leu Arg Ile Ala Pro Leu Ala Leu Phe Phe Leu Ala
1               5                   10                  15

Ala Ser Val Met Phe Thr Val Glu Lys Thr Glu Ala Gly Ile Pro Arg
            20                  25                  30

Gly Glu Ser Cys Val Phe Ile Pro Cys Ile Thr Ala Ala Ile Gly Cys
                35                  40                  45

Ser Cys Lys Ser Lys Val Cys Tyr Arg Asn His Val Ile Ala Ala Glu
        50                  55                  60

Ala Lys Thr Met Asp Asp His His Leu Leu Cys Gln Ser His Glu Asp
65                  70                  75                  80

Cys Ile Thr Lys Gly Thr Gly Asn Phe Cys Ala Pro Phe Pro Asp Gln
                85                  90                  95

Asp Ile Lys Tyr Gly Trp Cys Phe Arg Ala Glu Ser Glu Gly Phe Leu
            100                 105                 110

Leu Lys Asp His Leu Lys Met Ser Ile Thr Asn
        115                 120

<210> SEQ ID NO 81
<211> LENGTH: 490
<212> TYPE: DNA
<213> ORGANISM: Clitoria ternatea

<400> SEQUENCE: 81
ggggcaaagc atcaacttaa tccattaatg gcttcccttc gcattgctcc tctcgctctc     60
ttcttttttcc ttgccgcttc ggttatgttt acagtggaga agactgaagc cggtatccct   120
cgtggagaat cttgtgtatt tattccatgc ataacagcag ccatcggttg ttcttgtaaa    180
agcaaagttt gctatcgaaa ccatgtcatt gcagctgagg caaagacaat ggatgatcat    240
catctcttat gtcaatctca tgaagattgc atcactaaag gaactggaaa cttttgtgct    300
cctttccctg atcaagatat taaatatggt tggtgtttcc gtgctgagtc tgaaggattt    360
ctgttgaaag accacttaaa gatgtctatc ccaactgaa agtagtcatg tatgcataat     420
gaatctacta ttcaaaaag atacacatga tgcatgtact atcttaaata aatggttgtt    480
ttaattgcga                                                            490

<210> SEQ ID NO 82
<211> LENGTH: 123
<212> TYPE: PRT
<213> ORGANISM: Clitoria ternatea

<400> SEQUENCE: 82

Met Ala Ser Leu Arg Ile Ala Pro Leu Ala Leu Phe Phe Leu Ala
1               5                   10                  15

Ala Ser Val Met Phe Thr Val Glu Lys Thr Glu Ala Gly Ile Pro Cys
            20                  25                  30

Gly Glu Ser Cys Val Phe Ile Pro Cys Ile Thr Gly Ala Ile Gly Cys
                35                  40                  45

Ser Cys Lys Ser Lys Val Cys Tyr Arg Asn His Val Ile Ala Ala Glu
        50                  55                  60

Ala Lys Thr Met Asp Asp His His Leu Leu Cys Gln Ser His Glu Asp
65                  70                  75                  80

Cys Ile Thr Lys Gly Thr Gly Asn Phe Cys Ala Pro Phe Pro Asp Gln
```

```
                    85                  90                  95
Asp Ile Lys Tyr Gly Trp Cys Phe Arg Ala Glu Ser Glu Gly Phe Met
            100                 105                 110

Leu Lys Asp His Leu Lys Met Ser Ile Thr Asn
        115                 120

<210> SEQ ID NO 83
<211> LENGTH: 476
<212> TYPE: DNA
<213> ORGANISM: Clitoria ternatea

<400> SEQUENCE: 83
gggggcaaag catcaactta atccattaat ggcttcccct cgcattgctc ctctcgctct    60 cttcttttc cttgccgctt cggttatgtt tacagtggag aagactgaag ccggtatccc    120
ttgtggagaa tcttgtgtat ttattccatg cataacagga gccatcggtt gttcttgtaa    180
aagcaaagtt tgctatcgaa accatgtcat tgcagctgag gcaaagacaa tggatgatca    240
tcatctctta tgtcaatctc atgaagattg catcactaaa ggaactggaa acttttgtgc    300
tccttcccct gatcaagata ttaaatatgg ttggtgtttc cgtgctgagt ctgaaggatt    360
catgttgaaa gaccacttaa agatgtctat caccaactga aagtagtcat gtatgcataa    420
tgaatctact attacaaaaa gatacacatg atgcatgtac tatcttaaat aaatgg       476

<210> SEQ ID NO 84
<211> LENGTH: 123
<212> TYPE: PRT
<213> ORGANISM: Clitoria ternatea

<400> SEQUENCE: 84

Met Ala Ser Leu Arg Ile Ala Pro Leu Ala Leu Phe Phe Phe Leu Ala
  1               5                  10                  15

Ala Ser Val Met Phe Thr Val Glu Lys Thr Glu Ala Gly Ile Pro Cys
             20                  25                  30

Gly Glu Ser Cys Val Phe Ile Pro Cys Ile Thr Ala Ala Ile Gly Cys
         35                  40                  45

Ser Cys Lys Ser Lys Val Cys Tyr Arg Asn His Val Ile Ala Ala Glu
     50                  55                  60

Ala Lys Thr Met Asp Asp His His Leu Leu Cys Gln Ser His Glu Asp
 65                  70                  75                  80

Cys Ile Thr Lys Gly Thr Gly Asn Phe Cys Ala Pro Phe Pro Asp Gln
                 85                  90                  95

Asp Ile Lys Tyr Gly Trp Cys Phe Arg Ala Glu Ser Glu Gly Phe Leu
            100                 105                 110

Leu Lys Asp His Leu Lys Met Ser Ile Ile Asn
        115                 120

<210> SEQ ID NO 85
<211> LENGTH: 492
<212> TYPE: DNA
<213> ORGANISM: Clitoria ternatea

<400> SEQUENCE: 85
gggggcaaag catcaactta atccattaat ggcttcccct cgcattgctc ctctcgctct    60 cttcttttc cttgccgctt cggttatgtt tacagtggag aagactgaag ccggtatccc    120
ttgtggagaa tcttgtgtat ttattccatg cataacagca gccatcggtt gttcttgtaa    180
aagcaaagtt tgctatcgaa accatgtcat tgcagctgag gcaaagacaa tggatgatca    240
```

```
tcatctctta tgtcaatctc atgaagattg catcactaaa ggaactggaa actttgtgc      300 tcctttccct gatcaagata ttaaatatgg ttggtgtttc cgtgctgagt ctgaaggatt      360
tctgttgaaa gaccacttaa agatgtctat catcaactga agtagtcat  gtatgcataa      420 tgaatctact attacaaaaa gatacacatg atgcatgtac tatcttaaat aaatggttgt      480
tttaattaca gt                                                           492
```

<210> SEQ ID NO 86
<211> LENGTH: 123
<212> TYPE: PRT
<213> ORGANISM: Clitoria ternatea

<400> SEQUENCE: 86

```
Met Ala Ser Leu Arg Ile Ala Pro Leu Ala Leu Phe Phe Phe Leu Ala
  1               5                  10                  15

Ala Ser Val Met Phe Thr Val Glu Lys Thr Glu Ala Gly Ile Pro Cys
             20                  25                  30

Gly Glu Ser Cys Val Phe Ile Pro Cys Ile Thr Ala Ala Ile Gly Cys
         35                  40                  45

Ser Cys Lys Ser Lys Val Cys Tyr Arg Asn His Val Ile Ala Ala Glu
     50                  55                  60

Ala Lys Thr Met Asp Asp His Leu Leu Cys Gln Ser His Glu Asp
 65                  70                  75                  80

Cys Ile Thr Lys Gly Thr Gly Asn Phe Cys Ala Pro Phe Pro Asp Gln
                 85                  90                  95

Asp Ile Lys Tyr Gly Trp Cys Phe Arg Ala Glu Ser Glu Gly Phe Leu
            100                 105                 110

Leu Lys Asp His Leu Lys Met Ser Ile Thr Asn
        115                 120
```

<210> SEQ ID NO 87
<211> LENGTH: 473
<212> TYPE: DNA
<213> ORGANISM: Clitoria ternatea

<400> SEQUENCE: 87

```
ggggaaagca tcaacttaat ccattaatgg cttcccttcg cattgctcct ctcgctctct      60 tcttttttcct tgccgcttcg gttatgttta cagtggagaa gactgaagcc ggtatccctt     120
gtggagaatc ttgtgtattt attccatgca taacagcagc catcggttgt tcttgtaaaa     180
gcaaagtttg ctatcgaaac catgtcattg cagctgaggc aaagacaatg gatgatcatc     240
atctcttatg tcaatctcat gaagattgca tcactaaagg aactggaaac ttttgtgctc     300
ctttccctga tcaagatatt aaatatggtt ggtgtttccg tgctgagtct gaaggatttc     360
tgttgaaaga ccacttaaag atgtctatca ccaactgaaa gtagtcatgt atgcataatg     420
aatctactat tacaaaaaga tacacatgat gcatgtacta tcttaaataa atg            473
```

<210> SEQ ID NO 88
<211> LENGTH: 89
<212> TYPE: PRT
<213> ORGANISM: Clitoria ternatea

<400> SEQUENCE: 88

```
Glu Lys Thr Glu Ala Gly Ile Pro Cys Gly Glu Ser Cys Val Phe Ile
  1               5                  10                  15

Pro Cys Ile Thr Ala Ala Ile Gly Cys Ser Cys Lys Ser Lys Val Cys
             20                  25                  30
```

```
Tyr Arg Asn His Val Ile Ala Ala Glu Ala Lys Thr Met Asp Asp His
        35                  40                  45

His Leu Leu Cys Gln Ser His Glu Asp Cys Ile Thr Lys Gly Thr Gly
 50                  55                  60

Asn Phe Cys Ala Pro Phe Pro Asp Gln Asp Ile Lys Tyr Gly Trp Cys
 65                  70                  75                  80

Phe Arg Ala Glu Ser Glu Gly Phe Leu
                85

<210> SEQ ID NO 89
<211> LENGTH: 507
<212> TYPE: DNA
<213> ORGANISM: Clitoria ternatea

<400> SEQUENCE: 89
gggggagaag actgaagccg gtatcccttg tggagaatct tgtgtattta ttccatgcat    60
aacagcagcc atcggttgtt cttgtaaaag caaagtttgc tatcgaaacc atgtcattgc   120
agctgaggca aagacaatgg atgatcatca tctcttatgt caatctcatg aagattgcat   180
cactaaagga actggaaact tttgtgctcc tttccctgat caagatatta atatggttg    240 gtgtttccgt gctgagtctg aaggatttct gttgaaagac cacttaaaga tgtctatcac   300
caactgaaag tagtcatgta tgcataatga atctactatt acaaaaagat acacatgatg   360
catgtactat cttaaataaa tggttgtttt aatttctatt gttattttt aaatctcaat    420 tgcttatgtt tgtacattat atatgtattc ttttgagcat acatatataa agtgaacaaa   480
gaataatatt tgcatcgaaa aaaaaaa                                      507

<210> SEQ ID NO 90
<211> LENGTH: 123
<212> TYPE: PRT
<213> ORGANISM: Clitoria ternatea

<400> SEQUENCE: 90

Met Ala Ser Leu Arg Ile Ala Pro Leu Ala Leu Phe Phe Phe Leu Ala
 1               5                  10                  15

Ala Ser Val Met Phe Thr Val Glu Lys Thr Glu Ala Gly Ile Pro Cys
                20                  25                  30

Gly Glu Ser Cys Val Phe Ile Pro Cys Ile Thr Gly Ala Ile Gly Cys
            35                  40                  45

Ser Cys Lys Ser Lys Val Cys Tyr Arg Asn His Val Ile Ala Ala Glu
         50                  55                  60

Ala Lys Thr Met Asp Asp His His Leu Leu Cys Gln Ser His Glu Asp
 65                  70                  75                  80

Cys Ile Ile Lys Gly Thr Gly Asn Phe Cys Ala Ser Phe Pro Glu Gln
                85                  90                  95

Asp Ile Lys Tyr Gly Trp Cys Phe Arg Ala Glu Ser Glu Gly Phe Met
            100                 105                 110

Leu Lys Asp His Leu Lys Met Ser Ile Thr Asn
        115                 120

<210> SEQ ID NO 91
<211> LENGTH: 496
<212> TYPE: DNA
<213> ORGANISM: Clitoria ternatea

<400> SEQUENCE: 91
gggggcaaag catcaactta atccattaat ggcttcccct cgcattgctc ctctcgctct    60
```

```
cttcttttc  cttgccgctt  cggttatgtt  tacagtggag  aagactgaag  ccggtatccc     120
ttgtggagaa  tcttgtgtat  ttattccatg  cataacagga  gccatcggtt  gttcttgtaa     180
aagcaaagtt  tgctatcgaa  accatgtcat  tgcagctgag  gcaaagacaa  tggatgatca     240
tcatctcttg  tgtcaatctc  atgaagattg  catcattaaa  ggaactggaa  acttttgtgc     300
ttctttccct  gaacaagata  ttaaatatgg  ttggtgtttc  cgtgctgagt  ctgaaggatt     360
catgttgaaa  gatcatttaa  agatgtctat  caccaactga  aagtagtaat  gtatgcataa     420
tgaatctact  attacaaaaa  gatacacatg  atgcatgtac  tatcttaaat  aaatggttgt     480
ttcaattttt  attgtc                                                         496

<210> SEQ ID NO 92
<211> LENGTH: 123
<212> TYPE: PRT
<213> ORGANISM: Clitoria ternatea
<220> FEATURE:
<221> NAME/KEY: VARIANT
<222> LOCATION: 103
<223> OTHER INFORMATION: Xaa = Any Amino Acid

<400> SEQUENCE: 92

Met Ala Ser Leu Arg Ile Ala Pro Leu Ala Leu Phe Phe Phe Leu Ala
 1               5                  10                  15

Ala Ser Val Met Phe Thr Val Glu Lys Thr Glu Ala Gly Ile Pro Cys
            20                  25                  30

Gly Glu Ser Cys Val Phe Ile Pro Cys Ile Thr Gly Ala Ile Gly Cys
        35                  40                  45

Ser Cys Lys Ser Lys Val Cys Tyr Arg Asn His Val Ile Ala Ala Glu
    50                  55                  60

Ala Lys Thr Met Asp Asp His His Leu Leu Cys Gln Ser His Glu Asp
65                  70                  75                  80

Cys Ile Ile Lys Gly Thr Gly Asn Phe Cys Thr Ser Phe Pro Glu Gln
                85                  90                  95

Asp Ile Lys Tyr Gly Trp Xaa Phe Arg Ala Glu Ser Glu Gly Phe Met
            100                 105                 110

Leu Lys Asp His Leu Lys Met Ser Ile Thr Asn
        115                 120

<210> SEQ ID NO 93
<211> LENGTH: 495
<212> TYPE: DNA
<213> ORGANISM: Clitoria ternatea
<220> FEATURE:
<221> NAME/KEY: misc_feature
<222> LOCATION: 337
<223> OTHER INFORMATION: n = A,T,C or G

<400> SEQUENCE: 93 ggggcaaag  catcaactta  atccattaat  ggcttccctt  cgcattgctc  ctctcgctct      60 cttcttttc  cttgccgctt  cggttatgtt  tacagtggag  aagactgaag  ccggtatccc     120
ttgtggagaa  tcttgtgtat  ttattccatg  cataacagga  gccatcggtt  gttcttgtaa     180
aagcaaagtt  tgctatcgaa  accatgtcat  tgcagctgag  gcaaagacaa  tggatgatca     240
tcatctcttg  tgtcaatctc  atgaagattg  catcattaaa  ggaactggaa  acttttgtac     300
ttctttccct  gaacaagata  ttaaatatgg  ttggtgnttc  cgtgctgagt  ctgaaggatt     360
catgttgaaa  gatcatttaa  agatgtctat  caccaactga  aagtagtaat  gtatgcataa     420
tgaatctact  attacaaaaa  gatacacatg  atgcatgtac  tatcttaaat  aaatggttgt     480
```

```
ttcaattttt attgt                                                    495
```

<210> SEQ ID NO 94
<211> LENGTH: 124
<212> TYPE: PRT
<213> ORGANISM: Clitoria ternatea

<400> SEQUENCE: 94

| Met | Ala | Ser | Leu | Arg | Ile | Ala | Pro | Phe | Ala | Val | Phe | Leu | Phe | Leu | Ala |
|---|---|---|---|---|---|---|---|---|---|---|---|---|---|---|---|
| 1 |  |  |  | 5 |  |  |  |  | 10 |  |  |  |  | 15 |  |

| Ala | Ser | Val | Met | Phe | Ala | Val | Glu | Lys | Thr | Gln | Ala | Gly | Val | Ile | Pro |
|---|---|---|---|---|---|---|---|---|---|---|---|---|---|---|---|
|  |  |  | 20 |  |  |  |  | 25 |  |  |  |  | 30 |  |  |

| Cys | Gly | Glu | Ser | Cys | Val | Phe | Ile | Pro | Cys | Ile | Ser | Thr | Val | Ile | Gly |
|---|---|---|---|---|---|---|---|---|---|---|---|---|---|---|---|
|  |  |  | 35 |  |  |  |  | 40 |  |  |  |  | 45 |  |  |

| Cys | Ser | Cys | Lys | Asn | Lys | Val | Cys | Tyr | Arg | Asn | His | Val | Ile | Ala | Ala |
|---|---|---|---|---|---|---|---|---|---|---|---|---|---|---|---|
|  | 50 |  |  |  |  | 55 |  |  |  |  | 60 |  |  |  |  |

| Glu | Ala | Lys | Thr | Met | Asp | Glu | His | Leu | Leu | Leu | Cys | Gln | Ser | His | Glu |
|---|---|---|---|---|---|---|---|---|---|---|---|---|---|---|---|
| 65 |  |  |  | 70 |  |  |  |  | 75 |  |  |  |  | 80 |  |

| Asp | Cys | Ile | Ala | Lys | Gly | Thr | Gly | Asn | Phe | Cys | Ala | Pro | Phe | Pro | Asp |
|---|---|---|---|---|---|---|---|---|---|---|---|---|---|---|---|
|  |  |  |  | 85 |  |  |  |  | 90 |  |  |  |  | 95 |  |

| Gln | Asp | Ile | Lys | Tyr | Gly | Trp | Cys | Phe | Arg | Ala | Glu | Ser | Glu | Gly | Phe |
|---|---|---|---|---|---|---|---|---|---|---|---|---|---|---|---|
|  |  |  | 100 |  |  |  |  | 105 |  |  |  |  | 110 |  |  |

| Met | Leu | Lys | Asp | His | Leu | Lys | Met | Ser | Ile | Thr | Asn |
|---|---|---|---|---|---|---|---|---|---|---|---|
|  | 115 |  |  |  |  | 120 |  |  |  |  |  |

<210> SEQ ID NO 95
<211> LENGTH: 484
<212> TYPE: DNA
<213> ORGANISM: Clitoria ternatea

<400> SEQUENCE: 95

```
ggggagagca aagtcattgc ttatttcat caaattatgg cttcccttcg cattgctcct      60
ttcgctgtct tccttttcct tgctgcttcg gttatgtttg cagtggagaa gactcaagca    120
ggtgtcattc cttgcggaga atcttgtgta tttattccat gtatatcaac agttatcggc    180
tgttcttgta agaacaaagt ttgctatcga aaccatgtta ttgcagctga ggcaaagaca    240
atggatgagc atcttctctt atgtcaatct catgaagatt gcatcgctaa aggaactgga    300
aacttttgtg ctcctttccc tgatcaagat attaaatatg gttggtgttt ccgtgctgag    360
tctgaaggat tcatgttgaa agaccacttg aagatgtcta tcaccaactg aaagtagtca    420
tgcatggata atgaatctaa tactaaaaaa atgcacatga tgcatgtact atcttaaata    480
aatg                                                                 484
```

<210> SEQ ID NO 96
<211> LENGTH: 123
<212> TYPE: PRT
<213> ORGANISM: Clitoria ternatea

<400> SEQUENCE: 96

| Met | Ala | Ser | Leu | Arg | Ile | Ala | Pro | Leu | Ala | Leu | Phe | Phe | Leu | Ala |
|---|---|---|---|---|---|---|---|---|---|---|---|---|---|---|
| 1 |  |  |  | 5 |  |  |  |  | 10 |  |  |  |  | 15 |

| Ala | Ser | Val | Met | Phe | Thr | Val | Glu | Lys | Thr | Glu | Ala | Gly | Ile | Pro | Cys |
|---|---|---|---|---|---|---|---|---|---|---|---|---|---|---|---|
|  |  |  | 20 |  |  |  |  | 25 |  |  |  |  | 30 |  |  |

| Gly | Glu | Ser | Cys | Val | Phe | Ile | Pro | Cys | Ile | Thr | Ala | Ala | Ile | Gly | Cys |
|---|---|---|---|---|---|---|---|---|---|---|---|---|---|---|---|
|  |  | 35 |  |  |  |  | 40 |  |  |  |  | 45 |  |  |  |

| Ser | Cys | Lys | Ser | Lys | Val | Cys | Tyr | Arg | Asn | His | Val | Ile | Ala | Ala | Glu |
|---|---|---|---|---|---|---|---|---|---|---|---|---|---|---|---|
|  | 50 |  |  |  |  | 55 |  |  |  |  | 60 |  |  |  |  |

```
Ala Lys Thr Met Asp Asp His His Leu Leu Cys Gln Ser His Glu Asp
 65                  70                  75                  80

Cys Ile Thr Lys Gly Thr Gly Asn Phe Cys Ala Pro Phe Pro Asp Gln
                 85                  90                  95

Asp Ile Lys Tyr Gly Trp Cys Phe Arg Ala Glu Ser Glu Gly Phe Leu
            100                 105                 110

Leu Lys Asp His Leu Lys Met Ser Ile Thr Asn
        115                 120

<210> SEQ ID NO 97
<211> LENGTH: 487
<212> TYPE: DNA
<213> ORGANISM: Clitoria ternatea

<400> SEQUENCE: 97
ggggaaagca tcaacttaat ccattaatgg cttcccttcg cattgctcct ctcgctctct      60 tcttttcct tgccgcttcg gttatgttta cagtggagaa gactgaagcc ggtatccctt     120
gtggagaatc ttgtgtattt attccatgca taacagcagc catcggttgt tcttgtaaaa     180
gcaaagtttg ctatcgaaac catgtcattg cagctgaggc aaagacaatg gatgatcatc     240
atctcttatg tcaatctcat gaagattgca tcactaaagg aactggaaac ttttgtgctc     300
ctttccctga tcaagatatt aaatatggtt ggtgtttccg tgctgagtct gaaggatttc     360
tgttgaaaga ccacttaaag atgtctatca ccaactgaaa gtagtcatgt atgcataatg     420
aatctactat tacaaaaaga tacacatgat gcatgtacta tcttaaataa atggttgttt     480
taatttc                                                                487

<210> SEQ ID NO 98
<211> LENGTH: 123
<212> TYPE: PRT
<213> ORGANISM: Clitoria ternatea

<400> SEQUENCE: 98

Met Ala Ser Leu Arg Ile Ala Pro Leu Ala Leu Phe Phe Phe Leu Ala
 1               5                  10                  15

Ala Ser Val Met Phe Thr Val Glu Lys Thr Glu Ala Gly Ile Pro Cys
                 20                  25                  30

Gly Glu Ser Cys Val Phe Ile Pro Cys Ile Thr Ala Ala Ile Gly Cys
             35                  40                  45

Ser Cys Lys Ser Lys Val Cys Tyr Arg Asn His Val Ile Ala Ala Glu
         50                  55                  60

Ala Lys Thr Met Asp Asp His His Leu Leu Cys Gln Ser His Glu Asp
 65                  70                  75                  80

Cys Ile Thr Lys Gly Thr Gly Asn Phe Cys Ala Pro Phe Pro Asp Gln
                 85                  90                  95

Asp Ile Lys Tyr Gly Trp Cys Phe Arg Ala Glu Ser Glu Gly Phe Leu
            100                 105                 110

Leu Lys Asp His Leu Lys Met Ser Ile Thr Asn
        115                 120

<210> SEQ ID NO 99
<211> LENGTH: 488
<212> TYPE: DNA
<213> ORGANISM: Clitoria ternatea

<400> SEQUENCE: 99
ggggcaaagc atcaacttaa tccattaatg gcttcccttc gcattgctcc tctcgctctc      60
```

```
ttcttttttcc ttgccgcttc ggttatgttt acagtggaga agactgaagc cggtatccct    120
tgtggagaat cttgtgtatt tattccatgc ataacagcag ccatcggttg ttcttgtaaa    180
agcaaagttt gctatcgaaa ccatgtcatt gcagctgagg caaagacaat ggatgatcat    240
catctcttat gtcaatctca tgaagattgc atcactaaag gaactggaaa cttttgtgct    300
cctttccctg atcaagatat taaatatggt tggtgtttcc gtgctgagtc tgaaggattt    360
ctgttgaaag accacttaaa gatgtctatc accaactgaa agtagtcatg tatgcataat    420
gaatctacta ttacaaaaag atacacatga tgcatgtact atcttaaata aatggttgtt    480
ttaatttc                                                             488
```

<210> SEQ ID NO 100
<211> LENGTH: 124
<212> TYPE: PRT
<213> ORGANISM: Clitoria ternatea

<400> SEQUENCE: 100

```
Met Ala Ser Leu Arg Ile Ala Pro Phe Ala Val Phe Leu Phe Leu Ala
 1               5                  10                  15

Ala Ser Val Met Phe Ala Val Glu Lys Thr Gln Ala Gly Val Ile Pro
            20                  25                  30

Cys Gly Glu Ser Cys Val Phe Ile Pro Cys Ile Ser Thr Val Ile Gly
        35                  40                  45

Cys Ser Cys Lys Asn Lys Val Cys Tyr Arg Asn His Val Ile Ala Ala
    50                  55                  60

Glu Ala Lys Thr Met Asp Glu His Leu Leu Leu Cys Gln Ser His Glu
65                  70                  75                  80

Asp Cys Ile Ala Lys Gly Thr Gly Asn Phe Cys Ala Pro Phe Pro Asp
                85                  90                  95

Gln Asp Ile Lys Tyr Gly Trp Cys Phe Arg Ala Glu Ser Glu Gly Phe
            100                 105                 110

Met Leu Lys Asp His Leu Lys Met Ser Ile Thr Asn
        115                 120
```

<210> SEQ ID NO 101
<211> LENGTH: 607
<212> TYPE: DNA
<213> ORGANISM: Clitoria ternatea

<400> SEQUENCE: 101

```
gggggcagag caaagtcatt gcttattttc atcaaattat ggcttccctt cgcattgctc     60
ctttcgctgt cttccttttc cttgctgctt cggttatgtt tgcagtggag aagactcaag    120
caggtgtcat tccttgcgga gaatcttgtg tatttattcc atgtatatca acagttatcg    180
gctgttcttg taagaacaaa gtttgctatc gaaaccatgt tattgcagct gaggcaaaga    240
caatggatga gcatcttctc ttatgtcaat ctcatgaaga ttgcatcgct aaaggaactg    300
gaaacttttg tgctcctttc cctgatcaag atattaaata tggttggtgt ttccgtgctg    360
agtctgaagg attcatgttg aaagaccact tgaagatgtc tatcaccaac tgaaagtagt    420
catgcatgga taatgaatct aatactaaaa aaatgcacat gatgcatgta ctatcttaaa    480
taaatggctc tttagtgtc tattgttaat ttttaaatct taattgttta tgtttgtaca    540
ctctatatgt atgttgttga gcatacatat ataaagtgaa caaagaataa tactttcatt    600
tcaatgt                                                              607
```

<210> SEQ ID NO 102

<211> LENGTH: 124
<212> TYPE: PRT
<213> ORGANISM: Clitoria ternatea

<400> SEQUENCE: 102

Met Ala Ser Leu Arg Ile Ala Pro Phe Ala Val Phe Leu Phe Leu Ala
1               5                   10                  15

Ala Ser Val Met Phe Ala Val Glu Lys Thr Gln Ala Gly Val Ile Pro
            20                  25                  30

Cys Gly Glu Ser Cys Val Phe Ile Pro Cys Ile Ser Thr Val Ile Gly
        35                  40                  45

Cys Ser Cys Lys Asn Lys Val Cys Tyr Arg Asn His Val Ile Ala Ala
    50                  55                  60

Glu Ala Lys Thr Met Asp Glu His Leu Leu Cys Gln Ser His Glu
65                  70                  75                  80

Asp Cys Ile Ala Lys Gly Thr Gly Asn Phe Cys Ala Pro Phe Pro Asp
                85                  90                  95

Gln Asp Ile Lys Tyr Gly Trp Cys Phe Arg Ala Glu Ser Glu Gly Phe
            100                 105                 110

Met Leu Lys Asp His Leu Lys Met Ser Ile Thr Asn
        115                 120

<210> SEQ ID NO 103
<211> LENGTH: 512
<212> TYPE: DNA
<213> ORGANISM: Clitoria ternatea

<400> SEQUENCE: 103
ggggagagca aagtcattgc ttattttcat caaattatgg cttcccttcg cattgctcct        60
ttcgctgtct tccttttcct tgctgcttcg gttatgtttg cagtggagaa gactcaagca       120
ggtgtcattc cttgcggaga atcttgtgta tttattccat gtatatcaac agttatcggc       180
tgttcttgta agaacaaagt tgctatcga accatgtta ttgcagctga ggcaaagaca         240
atggatgagc atcttctctt atgtcaatct catgaagatt gcatcgctaa aggaactgga       300
aacttttgtg ctccttttcc ctgatcaagat attaaatatg gttggtgttt ccgtgctgag       360
tctgaaggat tcatgttgaa agaccacttg aagatgtcta tcaccaactg aaagtagtca       420
tgcatggata atgaatctaa tactaaaaaa aatgcacatg atgcatgtac tatcttaaat       480
aaatggctct tttagtgtct attgttaatt tg                                      512

<210> SEQ ID NO 104
<211> LENGTH: 123
<212> TYPE: PRT
<213> ORGANISM: Clitoria ternatea

<400> SEQUENCE: 104

Met Ala Ser Leu Arg Ile Ala Pro Leu Ala Leu Phe Phe Leu Ala
1               5                   10                  15

Ala Ser Val Met Phe Thr Val Glu Lys Thr Glu Ala Gly Ile Pro Cys
            20                  25                  30

Gly Glu Ser Cys Val Phe Ile Pro Cys Ile Thr Gly Ala Ile Gly Cys
        35                  40                  45

Ser Cys Lys Ser Lys Val Cys Tyr Arg Asn His Val Ile Ala Ala Glu
    50                  55                  60

Ala Lys Thr Met Asp Asp His His Leu Leu Cys Gln Ser His Glu Asp
65                  70                  75                  80

Cys Ile Ile Lys Gly Thr Gly Asn Phe Cys Ala Ser Phe Pro Glu Gln

```
                        85                  90                  95
Asp Ile Lys Tyr Gly Trp Cys Phe Arg Ala Glu Ser Glu Gly Phe Met
            100                 105                 110

Leu Lys Asp His Leu Lys Met Ser Ile Thr Asn
        115                 120

<210> SEQ ID NO 105
<211> LENGTH: 466
<212> TYPE: DNA
<213> ORGANISM: Clitoria ternatea

<400> SEQUENCE: 105
catcaactta atccattaat ggcttccctt cgcattgctc ctctcgctct cttcttttc      60 cttgccgctt cggttatgtt tacagtggag aagactgaag ccggtatccc ttgtggagaa   120
tcttgtgtat ttattccatg cataacagga gccatcggtt gttcttgtaa aagcaaagtt   180
tgctatcgaa accatgtcat tgcagctgag gcaaagacaa tggatgatca tcatctcttg   240
tgtcaatctc atgaagattg catcattaaa ggaactggaa acttttgtgc ttcttccct   300 gaacaagata ttaaatatgg ttggtgtttc cgtgctgagt ctgaaggatt catgttgaaa   360
gatcatttaa agatgtctat caccaactga agtagtaat gtatgcataa tgaatctact   420
attacaaaaa gatacacatg atgcatgtac tatcttaaat aaatgg                 466

<210> SEQ ID NO 106
<211> LENGTH: 124
<212> TYPE: PRT
<213> ORGANISM: Clitoria ternatea

<400> SEQUENCE: 106

Met Ala Ser Leu Arg Ile Ala Pro Phe Ala Val Phe Leu Phe Leu Ala
  1               5                  10                  15

Ala Ser Val Met Phe Ala Val Glu Lys Thr Gln Ala Gly Val Ile Pro
            20                  25                  30

Cys Gly Glu Ser Cys Val Phe Ile Pro Cys Ile Ser Thr Val Ile Gly
        35                  40                  45

Cys Ser Cys Lys Asn Lys Val Cys Tyr Arg Asn His Val Ile Ala Ala
    50                  55                  60

Glu Ala Lys Thr Met Asp Glu His Leu Leu Cys Gln Ser His Glu
 65                 70                  75                  80

Asp Cys Ile Ala Lys Gly Thr Gly Asn Phe Cys Ala Pro Phe Pro Asp
                85                  90                  95

Gln Asp Ile Lys Tyr Gly Trp Cys Phe Arg Ala Glu Ser Glu Gly Phe
            100                 105                 110

Met Leu Lys Asp His Leu Lys Met Ser Ile Thr Asn
        115                 120

<210> SEQ ID NO 107
<211> LENGTH: 499
<212> TYPE: DNA
<213> ORGANISM: Clitoria ternatea

<400> SEQUENCE: 107
gggggcagag caaagtcatt gcttatttc atcaaattat ggcttccctt cgcattgctc     60
ctttcgctgt cttccttttc cttgctgctt cggttatgtt tgcagtggag aagactcaag   120
caggtgtcat tccttgcgga gaatcttgtg tatttattcc atgtatatca acagttatcg   180
gctgttcttg taagaacaaa gtttgctatc gaaaccatgt tattgcagct gaggcaaaga   240
```

-continued

| | | | | |
|---|---|---|---|---|
| caatggatga | gcatcttctc | ttatgtcaat | ctcatgaaga | ttgcatcgct | aaaggaactg | 300 |
| gaaactttg | tgctcctttc | cctgatcaag | atattaaata | tggttggtgt | ttccgtgctg | 360 |
| agtctgaagg | attcatgttg | aaagaccact | tgaagatgtc | tatcaccaac | tgaaagtagt | 420 |
| catgcatgga | taatgaatct | aatactaaaa | aaatgcacat | gatgcatgta | ctatcttaaa | 480 |
| taaatggctc | ttttagtgc | | | | | 499 |

<210> SEQ ID NO 108
<211> LENGTH: 123
<212> TYPE: PRT
<213> ORGANISM: Clitoria ternatea

<400> SEQUENCE: 108

Met Ala Ser Leu Arg Ile Ala Pro Leu Ala Leu Phe Phe Phe Leu Ala
1               5                   10                  15

Ala Ser Val Met Phe Thr Val Glu Lys Thr Glu Ala Gly Ile Pro Cys
            20                  25                  30

Gly Glu Ser Cys Val Phe Ile Pro Cys Ile Thr Gly Ala Ile Gly Cys
        35                  40                  45

Ser Cys Lys Ser Lys Val Cys Tyr Arg Asn His Val Ile Ala Ala Glu
    50                  55                  60

Ala Lys Thr Met Asp Asp His Leu Leu Arg Gln Ser His Glu Asp
65                  70                  75                  80

Cys Ile Thr Lys Gly Thr Gly Asn Phe Cys Ala Ser Phe Pro Glu Gln
                85                  90                  95

Asp Ile Lys Tyr Gly Trp Cys Phe Arg Ala Glu Ser Glu Gly Phe Met
            100                 105                 110

Leu Lys Asp His Leu Lys Met Ser Val Thr Asn
        115                 120

<210> SEQ ID NO 109
<211> LENGTH: 483
<212> TYPE: DNA
<213> ORGANISM: Clitoria ternatea

<400> SEQUENCE: 109

| | | | | |
|---|---|---|---|---|
| gggggcaaag | catcaactta | atccattaat | ggcttccctt | cgcattgctc | ctctcgctct | 60 |
| cttcttttc | cttgccgctt | cggttatgtt | tacagtggag | aagactgaag | ccggtatccc | 120 |
| ttgtggagaa | tcttgtgtat | ttattccatg | cataacagga | gccatcggtt | gttcttgtaa | 180 |
| aagcaaagtt | tgctatcgaa | accatgtcat | tgcagctgag | gcaaagacaa | tggatgatca | 240 |
| tcatctctta | cgtcaatctc | atgaagattg | catcactaaa | ggaactggaa | acttttgtgc | 300 |
| ttcttttcct | gaacaagata | ttaaatatgg | ttggtgtttc | cgtgctgagt | ctgaaggatt | 360 |
| catgttgaaa | gatcatttaa | agatgtctgt | caccaactga | agtagtcat | gtatgcataa | 420 |
| tgaatctact | attacaaaaa | gatacacatg | atgcatgtac | tatcttaaat | aaatggttgt | 480 |
| ttt | | | | | | 483 |

<210> SEQ ID NO 110
<211> LENGTH: 123
<212> TYPE: PRT
<213> ORGANISM: Clitoria ternatea

<400> SEQUENCE: 110

Met Ala Ser Leu Arg Ile Ala Pro Leu Ala Leu Phe Phe Phe Leu Ala
1               5                   10                  15

Ala Ser Val Met Phe Thr Val Glu Lys Thr Glu Ala Gly Ile Pro Cys

```
                    20                  25                  30

Gly Glu Ser Cys Val Phe Ile Pro Cys Ile Thr Gly Ala Ile Gly Cys
            35                  40                  45

Ser Cys Lys Ser Lys Val Cys Tyr Arg Asn His Val Ile Ala Ala Glu
        50                  55                  60

Ala Lys Thr Met Asp Asp His His Leu Leu Cys Gln Ser His Glu Asp
 65                 70                  75                  80

Cys Ile Ile Lys Gly Thr Gly Asn Phe Cys Ala Ser Phe Pro Glu Gln
                85                  90                  95

Asp Ile Lys Tyr Gly Trp Cys Phe Arg Ala Glu Ser Glu Gly Phe Met
            100                 105                 110

Leu Lys Asp His Leu Lys Met Ser Ile Thr Asn
            115                 120

<210> SEQ ID NO 111
<211> LENGTH: 504
<212> TYPE: DNA
<213> ORGANISM: Clitoria ternatea

<400> SEQUENCE: 111
gggggcaaag catcaactta atccattaat ggcttcccct cgcattgctc ctctcgctct      60 cttcttttc cttgccgctt cggttatgtt tacagtggag aagactgaag ccggtatccc     120
ttgtggagaa tcttgtgtat ttattccatg cataacagga gccatcggtt gttcttgtaa     180
aagcaaagtt tgctatcgaa accatgtcat tgcagctgag gcaaagacaa tggatgatca     240
tcatctcttg tgtcaatctc atgaagattg catcattaaa ggaactggaa acttttgtgc     300
ttctttccct gaacaagata ttaaatatgg ttggtgtttc cgtgctgagt ctgaaggatt     360
catgttgaaa gatcatttaa agatgtctat caccaactga agtagtaat gtatgcataa     420 tgaatctact attacaaaaa gatacacatg atgcatgtac tatcttaaat aaatggttgt     480 ttcaatttt attgttattt ttag                                             504

<210> SEQ ID NO 112
<211> LENGTH: 123
<212> TYPE: PRT
<213> ORGANISM: Clitoria ternatea

<400> SEQUENCE: 112

Met Ala Ser Leu Arg Ile Ala Pro Leu Ala Leu Phe Phe Phe Leu Ala
  1               5                  10                  15

Ala Ser Val Met Phe Thr Val Glu Lys Thr Glu Ala Gly Ile Pro Cys
            20                  25                  30

Gly Glu Ser Cys Val Phe Ile Pro Cys Ile Thr Gly Ala Ile Gly Cys
            35                  40                  45

Ser Cys Lys Ser Lys Val Cys Tyr Arg Asn His Val Ile Ala Ala Glu
        50                  55                  60

Ala Lys Thr Met Asp Asp His His Leu Leu Cys Gln Ser His Glu Asp
 65                 70                  75                  80

Cys Ile Thr Lys Gly Thr Gly Asn Phe Cys Ala Ser Phe Pro Glu Gln
                85                  90                  95

Asp Ile Lys Tyr Gly Trp Cys Phe Arg Ala Glu Ser Glu Gly Phe Met
            100                 105                 110

Leu Lys Asp His Leu Lys Met Ser Val Thr Asn
            115                 120

<210> SEQ ID NO 113
```

```
<211> LENGTH: 494
<212> TYPE: DNA
<213> ORGANISM: Clitoria ternatea

<400> SEQUENCE: 113
ggggaaagca tcaacttaat ccattaatgg cttcccttcg cattgctcct ctcgctctct      60 tcttttcct  tgccgcttcg gttatgttta cagtggagaa gactgaagcc ggtatccctt     120
gtggagaatc ttgtgtattt attccatgca taacaggagc catcggttgt tcttgtaaaa     180
gcaaagtttg ctatcgaaac catgtcattg cagctgaggc aaagacaatg gatgatcatc     240
atctcttatg tcaatctcat gaagattgca tcactaaagg aactggaaac ttttgtgctt     300
cttttcctga acaagatatt aaatatggtt ggtgtttccg tgctgagtct gaaggattca     360
tgttgaaaga tcatttaaag atgtctgtca ccaactgaaa gtagtcatgt atgcataatg     420
aatctactat tacaaaaaga tacacatgat gcatgtacta tcttaaataa atggttgttt     480
taatttctat tgct                                                       494

<210> SEQ ID NO 114
<211> LENGTH: 123
<212> TYPE: PRT
<213> ORGANISM: Clitoria ternatea

<400> SEQUENCE: 114

Met Ala Ser Leu Arg Ile Ala Pro Leu Ala Leu Phe Phe Phe Leu Ala
 1               5                  10                  15

Ala Ser Val Met Phe Thr Val Glu Lys Thr Glu Ala Gly Ile Pro Cys
            20                  25                  30

Gly Glu Ser Cys Val Phe Ile Pro Cys Ile Thr Ala Ala Ile Gly Cys
        35                  40                  45

Ser Cys Lys Ser Lys Val Cys Tyr Arg Asn His Val Ile Ala Ala Glu
    50                  55                  60

Ala Lys Thr Met Asp Asp His His Leu Leu Cys Gln Ser His Glu Asp
65                  70                  75                  80

Cys Ile Thr Lys Gly Thr Gly Asn Phe Cys Ala Pro Phe Pro Asp Gln
                85                  90                  95

Asp Ile Lys Tyr Gly Trp Cys Phe Arg Ala Glu Ser Glu Gly Phe Leu
            100                 105                 110

Leu Lys Asp His Leu Lys Met Ser Ile Thr Asn
        115                 120

<210> SEQ ID NO 115
<211> LENGTH: 504
<212> TYPE: DNA
<213> ORGANISM: Clitoria ternatea

<400> SEQUENCE: 115 gggggggcaaa gcatcaactt aatccattaa tggcttccct tcgcattgct cctctcgctc      60
tcttcttttt ccttgccgct tcggttatgt ttacagtgga agactgaa  gccggtatcc      120 cttgtggaga atcttgtgta tttattccat gcataacagc agccatcggt tgttcttgta     180
aaagcaaagt ttgctatcga aaccatgtca ttgcagctga ggcaaagaca atggatgatc     240
atcatctctt atgtcaatct catgaagatt gcatcactaa ggaactggaa acttttgtg     300 ctccttttccc tgatcaagat attaaatatg gttggtgttt ccgtgctgag tctgaaggat     360
ttctgttgaa agaccactta agatgtctca tccaactg aaagtagtca tgtatgcata       420
atgaatctac tattacaaaa agatacacat gatgcatgta ctatcttaaa taatggttg     480
```

-continued ttttaatttc tattgttatt tttt                                                    504

<210> SEQ ID NO 116
<211> LENGTH: 124
<212> TYPE: PRT
<213> ORGANISM: Clitoria ternatea

<400> SEQUENCE: 116

Met Ala Ser Leu Arg Ile Ala Pro Phe Ala Val Phe Leu Phe Leu Ala
 1               5                  10                  15

Ala Ser Val Met Phe Ala Val Glu Lys Thr Gln Ala Gly Val Ile Pro
            20                  25                  30

Cys Gly Glu Ser Cys Val Phe Ile Pro Cys Ile Ser Thr Val Ile Gly
        35                  40                  45

Cys Ser Cys Lys Asn Lys Val Cys Tyr Arg Asn His Val Ile Ala Ala
    50                  55                  60

Glu Ala Lys Thr Met Asp Glu His Leu Leu Cys Gln Ser His Glu
65                  70                  75                  80

Asp Cys Ile Ala Lys Gly Thr Gly Asn Phe Cys Ala Pro Pro Asp
                85                  90                  95

Gln Asp Ile Lys Tyr Gly Trp Cys Phe Arg Ala Glu Ser Glu Gly Phe
            100                 105                 110

Met Leu Lys Asp His Leu Lys Met Ser Ile Thr Asn
        115                 120

<210> SEQ ID NO 117
<211> LENGTH: 601
<212> TYPE: DNA
<213> ORGANISM: Clitoria ternatea

<400> SEQUENCE: 117
gggggcagag caaagtcatt gcttattttc atcaaattat ggcttccctt cgcattgctc    60 cttttcgctgt cttcctttc cttgctgctt cggttatgtt tgcagtggag aagactcaag   120
caggtgtcat tccttgcgga gaatcttgcg tatttattcc atgtatatca acagttatcg   180
gctgttcttg taagaacaaa gtttgctatc gaaaccatgt tattgcagct gaggcaaaga   240
caatggatga gcatcttctc ttatgtcaat ctcatgaaga ttgcatcgct aaaggaactg   300
gaaacttttg tgctcctttc cctgatcaag atattaaata tggttggtgt ttccgtgctg   360
agtctgaagg attcatgttg aaagaccact tgaagatgtc tatcaccaac tgaaagtagt   420
catgcatgga taatgaatct aatactaaaa aaatgcacat gatgcatgta ctatcttaaa   480
taaatggctc ttttagtgtc tattgttaat ttttaaatct taattgctta tgtttgtaca   540
ctctatatgt atgttgttga gcatacatat ataaagtgaa caaagaataa tactttcatt   600
t                                                                    601

<210> SEQ ID NO 118
<211> LENGTH: 123
<212> TYPE: PRT
<213> ORGANISM: Clitoria ternatea

<400> SEQUENCE: 118

Met Ala Ser Leu Arg Ile Ala Pro Leu Ala Leu Phe Phe Leu Ala
 1               5                  10                  15

Ala Ser Val Met Phe Thr Val Glu Lys Thr Glu Ala Gly Ile Pro Cys
            20                  25                  30

Gly Glu Ser Cys Val Phe Ile Pro Cys Ile Thr Ala Ala Ile Gly Cys
        35                  40                  45

```
Ser Cys Lys Ser Lys Val Cys Tyr Arg Asn His Val Ile Ala Ala Glu
    50                  55                  60

Ala Lys Thr Met Asp Asp His His Leu Leu Cys Gln Ser His Glu Asp
65                  70                  75                  80

Cys Ile Thr Lys Gly Thr Gly Asn Phe Cys Ala Pro Phe Pro Asp Gln
                85                  90                  95

Asp Ile Lys Tyr Gly Trp Cys Phe Arg Ala Glu Ser Glu Gly Phe Leu
            100                 105                 110

Leu Lys Asp His Leu Lys Met Ser Ile Thr Asn
        115                 120

<210> SEQ ID NO 119
<211> LENGTH: 490
<212> TYPE: DNA
<213> ORGANISM: Clitoria ternatea

<400> SEQUENCE: 119
gggggcaaag catcaactta atccattaat ggcttccctt cgcattgctc ctctcgctct      60 cttcttttc cttgccgctt cggttatgtt tacagtggag aagactgaag ccggtatccc      120
ttgtggagaa tcttgtgtat ttattccatg cataacagca gccatcggtt gttcttgtaa     180
aagcaaagtt tgctatcgaa accatgtcat tgcagctgag gcaaagacaa tggatgatca     240
tcatctctta tgtcaatctc atgaagattg catcactaaa ggaactggaa acttttgtgc     300
tccttcccct gatcaagata ttaaatatgg ttggtgtttc cgtgctgagt ctgaaggatt     360
tctgttgaaa gaccacttaa agatgtctat caccaactga agtagtcat gtatgcataa      420 tgaatctact attacaaaaa gatacacatg atgcatgtac tatcttaaat aaatggttgt     480
tttaattccc                                                            490

<210> SEQ ID NO 120
<211> LENGTH: 124
<212> TYPE: PRT
<213> ORGANISM: Clitoria ternatea

<400> SEQUENCE: 120

Met Ala Ser Leu Arg Ile Ala Pro Phe Ala Val Phe Leu Phe Leu Ala
1               5                   10                  15

Ala Ser Val Met Phe Ala Val Glu Lys Thr Gln Ala Gly Val Ile Pro
            20                  25                  30

Cys Gly Glu Ser Cys Val Phe Ile Pro Cys Ile Ser Thr Val Ile Gly
        35                  40                  45

Cys Ser Cys Lys Asn Lys Val Cys Tyr Arg Asn His Val Ile Ala Ala
    50                  55                  60

Glu Ala Lys Thr Met Asp Glu His Leu Leu Leu Cys Gln Ser His Glu
65                  70                  75                  80

Asp Cys Ile Ala Lys Gly Thr Gly Asn Phe Cys Ala Pro Phe Pro Asp
                85                  90                  95

Gln Asp Ile Lys Tyr Gly Trp Cys Phe Arg Ala Glu Ser Glu Gly Phe
            100                 105                 110

Met Leu Lys Asp His Leu Lys Met Ser Ile Thr Asn
        115                 120

<210> SEQ ID NO 121
<211> LENGTH: 505
<212> TYPE: DNA
<213> ORGANISM: Clitoria ternatea
```

-continued

<400> SEQUENCE: 121

```
gggagagca aagtcattgc ttattttcat caaattatgg cttcccttcg cattgctcct      60
ttcgctgtct tccttttcct tgctgcttcg gttatgtttg cagtggagaa gactcaagca    120
ggtgtcattc cttgcggaga atcttgtgta tttattccat gtatatcaac agttatcggc    180
tgttcttgta agaacaaagt tgctatcga aaccatgtta ttgcagctga ggcaaagaca     240
atggatgagc atcttctctt atgtcaatct catgaagatt gcatcgctaa aggaactgga    300
aacttttgtg ctccttttcc tgatcaagat attaaatatg gttggtgttt ccgtgctgag    360
tctgaaggat tcatgttgaa agaccacttg aagatgtcta tcaccaactg aaagtagtca    420
tgcatggata atgaatctaa tactaaaaaa atgcacatga tgcatgtact atcttaaata    480
aatggctctt ttagtgtcta ttgct                                          505
```

<210> SEQ ID NO 122
<211> LENGTH: 123
<212> TYPE: PRT
<213> ORGANISM: Clitoria ternatea

<400> SEQUENCE: 122

```
Met Ala Ser Leu Arg Ile Ala Pro Leu Ala Leu Phe Phe Phe Leu Ala
  1               5                  10                  15

Ala Ser Val Met Phe Thr Val Glu Lys Thr Glu Ala Gly Ile Pro Cys
             20                  25                  30

Gly Glu Ser Cys Val Phe Ile Pro Cys Ile Thr Gly Ala Ile Gly Cys
         35                  40                  45

Ser Cys Lys Ser Lys Val Cys Tyr Arg Asn His Val Ile Ala Ala Glu
     50                  55                  60

Ala Lys Thr Met Asp Asp His His Leu Leu Cys Gln Ser His Glu Asp
 65                  70                  75                  80

Cys Ile Ile Lys Gly Thr Gly Asn Phe Cys Ala Ser Phe Pro Glu Gln
                 85                  90                  95

Asp Ile Lys Tyr Gly Trp Cys Phe Arg Ala Glu Ser Glu Gly Phe Met
            100                 105                 110

Leu Lys Asp His Leu Lys Met Ser Ile Thr Asn
        115                 120
```

<210> SEQ ID NO 123
<211> LENGTH: 498
<212> TYPE: DNA
<213> ORGANISM: Clitoria ternatea

<400> SEQUENCE: 123

```
gggggcaaag catcaactta atccattaat ggcttcccttcgcattgctc ctctcgctct     60
cttcttttc cttgccgctt cggttatgtt tacagtggag aagactgaag ccggtatccc    120
ttgtggagaa tcttgtgtat ttattccatg cataacagga gccatcggtt gttcttgtaa    180
aagcaaagtt tgctatcgaa accatgtcat tgcagctgag gcaaagacaa tggatgatca    240
tcatctcttg tgtcaatctc atgaagattg catcattaaa ggaactggaa acttttgtgc    300
ttctttccct gaacaagata ttaaatatgg ttggtgtttc cgtgctgagt ctgaaggatt    360
catgttgaaa gatcatttaa agatgtctat caccaactga aagtagtaat gtatgcataa    420
tgaatctact attacaaaaa gatacacatg atgcatgtac tatcttaaat aaatggttgt    480
ttcaattttt attgctag                                                  498
```

<210> SEQ ID NO 124

<211> LENGTH: 126
<212> TYPE: PRT
<213> ORGANISM: Clitoria ternatea

<400> SEQUENCE: 124

```
Met Ala Lys Leu Val Pro Leu Ile Val Ile Phe Leu Val Ala Thr Ser
1               5                   10                  15

Val Asp Met Thr Lys Ala Ser Ile Pro Cys Gly Glu Ser Cys Val Tyr
            20                  25                  30

Ile Pro Cys Leu Thr Thr Ile Val Gly Cys Ser Cys Lys Ser Asn Val
        35                  40                  45

Cys Tyr Ser Asn His Val Ile Ala Ala Thr Ala Lys Ser Leu Asp Glu
    50                  55                  60

His Arg Leu Leu Cys Gln Ser His Glu Asp Cys Phe Val Lys Gly Thr
65                  70                  75                  80

Gly Asn Phe Cys Ala His Phe Pro Glu Gly Asp Val Ala Tyr Gly Trp
                85                  90                  95

Cys Phe His Ala Glu Ser Glu Gly Tyr Leu Leu Lys Asp Phe Leu Lys
            100                 105                 110

Met Pro Lys Gly Ile Val Lys Lys Pro Met Glu Ile Val Asn
        115                 120                 125
```

<210> SEQ ID NO 125
<211> LENGTH: 577
<212> TYPE: DNA
<213> ORGANISM: Clitoria ternatea

<400> SEQUENCE: 125

```
gggggcatag taaaacctat aacaaatatc agtaatcaac ttagtcaaat aatggctaaa      60
cttgttcctc tcattgtgat cttcttggtc gccacttctg tggatatgac aaaagctagt     120
atacettgtg gagaatcctg tgtatacatt ccatgtttaa cgacaattgt cggatgttcc     180
tgtaaaagca atgtttgtta tagtaaccat gtcattgctg ccactgcaaa atcattggat     240
gaacatcgtc tcttatgtca atctcatgaa gattgtttcg taaaaggaac cggaaacttt     300
tgtgctcatt ttcccgaagg agatgttgca tatggttggt gtttccatgc tgaatctgaa     360
ggatatttat tgaaggactt tctaaaaatg cccaaaggca tcgtgaaaaa gcctatggaa     420
attgtcaact aaaaattatc atgcatgttg catctatcac acctttaatt aaaataagat     480
gcatctactc ctttaaataa tgtcaaaagg ctcgagtgct cctctactac tgaatgtaat     540
ttacaactcc ccaaaataat atatatcaat ttggaga                              577
```

<210> SEQ ID NO 126
<211> LENGTH: 126
<212> TYPE: PRT
<213> ORGANISM: Clitoria ternatea

<400> SEQUENCE: 126

```
Met Ala Lys Leu Val Pro Leu Ile Val Ile Phe Leu Val Ala Thr Ser
1               5                   10                  15

Val Asp Met Thr Lys Ala Ser Ile Pro Cys Gly Glu Ser Cys Val Tyr
            20                  25                  30

Ile Pro Cys Leu Thr Thr Ile Val Gly Cys Ser Cys Lys Ser Asn Val
        35                  40                  45

Cys Tyr Ser Asn His Val Ile Ala Ala Thr Ala Lys Ser Leu Asp Glu
    50                  55                  60

His Arg Leu Leu Cys Gln Ser His Glu Asp Cys Phe Val Lys Gly Thr
65                  70                  75                  80
```

```
Gly Asn Phe Cys Ala His Phe Pro Glu Gly Asp Val Ala Tyr Gly Trp
                85                  90                  95

Cys Phe His Ala Glu Ser Glu Gly Tyr Leu Leu Lys Asp Phe Leu Lys
            100                 105                 110

Met Pro Lys Gly Ile Val Lys Pro Met Glu Ile Val Asn
        115                 120                 125

<210> SEQ ID NO 127
<211> LENGTH: 578
<212> TYPE: DNA
<213> ORGANISM: Clitoria ternatea

<400> SEQUENCE: 127
gggggcatag caaaacctat aacaaatatc agtaatcaac ttagtcaaat aatggctaaa      60
cttgttcctc tcattgtgat cttcttggtc gccacttctg tggatatgac aaaagctagt     120
ataccttgtg gagaatcctg tgtatacatt ccatgtttaa cgacaattgt cggatgttcc     180
tgtaaaagca atgtttgtta tgtaaccat gtcattgctg ccactgcaaa atcattggat      240
gaacatcgtc tcttatgtca atctcatgaa gattgtttcg taaaaggaac cggaaacttt     300
tgtgctcatt ttcccgaagg agatgttgca tatggttggt gtttccatgc tgaatctgaa     360
ggatatttat tgaaggactt tctaaaaatg cccaaaggca tcgtgaaaaa gcctatggaa     420
attgtcaact aaaaattatc atgcatgttg catctatcac acctttaatt aaaataagat     480
gcatctactc ctttaaataa tgtcaaaagg ctcgagtgct cctctactac tgaatgtaat     540
ttacaactcc ccaaaataat atatatcaat ttggagtg                            578

<210> SEQ ID NO 128
<211> LENGTH: 123
<212> TYPE: PRT
<213> ORGANISM: Clitoria ternatea

<400> SEQUENCE: 128

Met Ala Ser Leu Arg Ile Ala Pro Leu Ala Leu Phe Phe Phe Leu Ala
  1               5                  10                  15

Ala Ser Val Met Phe Thr Val Glu Lys Thr Glu Ala Gly Ile Pro Cys
             20                  25                  30

Gly Glu Ser Cys Val Phe Ile Pro Cys Ile Thr Ala Ala Ile Gly Cys
         35                  40                  45

Ser Cys Lys Ser Lys Val Cys Tyr Arg Asn His Val Ile Ala Ala Glu
     50                  55                  60

Ala Lys Thr Met Asp Asp His His Leu Leu Cys Gln Ser His Glu Asp
 65                  70                  75                  80

Cys Ile Thr Lys Gly Thr Gly Asn Ser Cys Ala Pro Phe Pro Asp Gln
                 85                  90                  95

Asp Ile Lys Tyr Gly Trp Cys Phe Arg Ala Glu Ser Glu Gly Phe Leu
            100                 105                 110

Leu Lys Asp His Leu Lys Met Ser Ile Thr Asn
        115                 120

<210> SEQ ID NO 129
<211> LENGTH: 499
<212> TYPE: DNA
<213> ORGANISM: Clitoria ternatea

<400> SEQUENCE: 129
ggggatcgca aagcatcaac ttaatccatt aatggcttcc cttcgcattg ctcctctcgc      60
```

```
tctcttctttt tccttgccg cttcggttat gtttacagtg gagaagactg aagccggtat    120
cccttgtgga gaatcttgtg tatttattcc atgcataaca gcagccatcg gttgttcttg    180
taaaagcaaa gtttgctatc gaaaccatgt cattgcagct gaggcaaaga caatggatga    240
tcatcatctc ttatgtcaat ctcatgaaga ttgcatcact aaaggaactg aaactcttg    300 tgctcctttc cctgatcaag atattaaata tggttggtgt ttccgtgctg agtctgaagg    360
atttctgttg aaagaccact aaagatgtc tatcaccaac tgaaagtagt catgtatgca    420
taatgaatct actattacaa aaagatacac atgatgcatg tactatctta aataaatggt    480
tgttttaatt tctattgtg                                                 499

<210> SEQ ID NO 130
<211> LENGTH: 123
<212> TYPE: PRT
<213> ORGANISM: Clitoria ternatea

<400> SEQUENCE: 130

Met Ala Ser Leu Arg Ile Ala Pro Leu Ala Leu Phe Phe Phe Leu Ala
1               5                   10                  15

Ala Ser Val Met Phe Thr Val Glu Lys Thr Glu Ala Gly Ile Pro Cys
            20                  25                  30

Gly Glu Ser Cys Val Phe Ile Pro Cys Ile Thr Gly Ala Ile Gly Cys
        35                  40                  45

Ser Cys Lys Ser Lys Val Cys Tyr Arg Asn His Val Ile Ala Ala Glu
    50                  55                  60

Ala Lys Thr Met Asp Asp His His Leu Leu Cys Gln Ser His Glu Asp
65                  70                  75                  80

Cys Ile Ile Lys Gly Thr Gly Asn Phe Cys Ala Ser Phe Pro Glu Gln
                85                  90                  95

Asp Ile Lys Tyr Gly Trp Cys Phe Arg Ala Glu Ser Glu Gly Phe Met
            100                 105                 110

Leu Lys Asp His Leu Lys Met Ser Ile Thr Asn
        115                 120

<210> SEQ ID NO 131
<211> LENGTH: 491
<212> TYPE: DNA
<213> ORGANISM: Clitoria ternatea

<400> SEQUENCE: 131
gggggcaaag catcaactta atccattaat ggcttcccctt cgcattgctc ctctcgctct    60 cttcttttc cttgccgctt cggttatgtt tacagtggag aagactgaag ccggtatccc    120
ttgtggagaa tcttgtgtat ttattccatg cataacagga gccatcggtt gttcttgtaa    180
aagcaaagtt tgctatcgaa accatgtcat tgcagctgag gcaaagacaa tggatgatca    240
tcatctcttg tgtcaatctc atgaagattg catcattaaa ggaactggaa acttttgtgc    300
ttctttccct gaacaagata ttaaatatgg ttggtgtttc cgtgctgagt ctgaaggatt    360
catgttgaaa gatcatttaa agatgtctat caccaactga agtagtaat gtatgcataa    420 tgaatctact attacaaaaa gatacacatg atgcatgtac tatcttaaat aaatggttgt    480
tcaattttta a                                                         491

<210> SEQ ID NO 132
<211> LENGTH: 124
<212> TYPE: PRT
<213> ORGANISM: Clitoria ternatea
```

<400> SEQUENCE: 132

Met Ala Ser Leu Arg Ile Ala Pro Phe Ala Val Phe Leu Phe Leu Ala
1               5                   10                  15

Ala Ser Val Met Phe Ala Val Glu Lys Thr Gln Ala Gly Val Ile Pro
            20                  25                  30

Cys Gly Glu Ser Cys Val Phe Ile Pro Cys Ile Ser Thr Val Ile Gly
        35                  40                  45

Cys Ser Cys Lys Asn Lys Val Cys Tyr Arg Asn His Val Ile Ala Ala
    50                  55                  60

Glu Ala Lys Thr Met Asp Glu His Leu Leu Cys Gln Ser His Glu
65                  70                  75                  80

Asp Cys Ile Ala Lys Gly Thr Gly Asn Phe Cys Ala Pro Phe Pro Asp
                85                  90                  95

Gln Asp Ile Lys Tyr Gly Trp Cys Phe Arg Ala Glu Ser Glu Gly Phe
            100                 105                 110

Met Leu Lys Asp His Leu Lys Met Ser Ile Thr Asn
        115                 120

<210> SEQ ID NO 133
<211> LENGTH: 500
<212> TYPE: DNA
<213> ORGANISM: Clitoria ternatea

<400> SEQUENCE: 133 ggggcagag caaagtcatt gcttattttc atcaaattat ggcttccctt cgcattgctc      60
ctttcgctgt cttcctttc cttgctgctt cggttatgtt tgcagtggag aagactcaag    120
caggtgtcat tccttgcgga gaatcttgtg tatttattcc atgtatatca acagttatcg   180
gctgttcttg taagaacaaa gtttgctatc gaaaccatgt tattgcagct gaggcaaaga   240
caatggatga gcatcttctc ttatgtcaat ctcatgaaga ttgcatcgct aaaggaactg   300
gaaacttttg tgctcctttc cctgatcaag atattaaata tggttggtgt ttccgtgctg   360
agtctgaagg attcatgctg aaagaccact tgaagatgtc tatcaccaac tgaaagtagt   420
catgcatgga taatgaatct aatactaaaa aaatgcacat gatgcatgta ctatcttaaa   480
taaatggctc ttttagtggc                                               500

<210> SEQ ID NO 134
<211> LENGTH: 123
<212> TYPE: PRT
<213> ORGANISM: Clitoria ternatea

<400> SEQUENCE: 134

Met Ala Ser Leu Arg Ile Ala Pro Leu Ala Leu Phe Phe Leu Ala
1               5                   10                  15

Ala Ser Val Met Phe Thr Val Glu Lys Thr Glu Ala Gly Ile Pro Cys
            20                  25                  30

Gly Glu Ser Cys Val Phe Ile Pro Cys Ile Thr Gly Ala Ile Gly Cys
        35                  40                  45

Ser Cys Lys Ser Lys Val Cys Tyr Arg Asn His Val Ile Ala Ala Glu
    50                  55                  60

Ala Lys Thr Met Asp Asp His His Leu Leu Cys Gln Ser His Glu Asp
65                  70                  75                  80

Cys Ile Ile Lys Gly Thr Gly Asn Phe Cys Ala Ser Phe Pro Glu Gln
                85                  90                  95

Asp Ile Lys Tyr Gly Trp Cys Phe Arg Ala Glu Ser Glu Gly Phe Met
            100                 105                 110

```
<210> SEQ ID NO 135
<211> LENGTH: 494
<212> TYPE: DNA
<213> ORGANISM: Clitoria ternatea

<400> SEQUENCE: 135
ggggaaagca tcaacttaat ccattaatgg cttcccttcg cattgctcct ctcgctctct      60 tcttttcct tgccgcttcg gttatgttta cagtggagaa gactgaagcc ggtatccctt     120
gtggagaatc ttgtgtattt attccatgca taacaggagc catcggttgt tcttgtaaaa    180
gcaaagtttg ctatcgaaac catgtcattg cagctgaggc aaagacaatg gatgatcatc    240
atctcttgtg tcaatctcat gaagattgca tcattaaagg aactggaaac ttttgtgctt    300
ctttccctga caagatatt aaatatggtt ggtgtttccg tgctgagtct gaaggattca     360
tgttgaaaga tcatttaaag atgtctatca ccaactgaaa gtagtaatgt atgcataatg    420
aatctactat tacaaaaaga tacacatgat gcatgtacta tcttaaataa atggttgttt    480
caatttttat tgtt                                                      494

<210> SEQ ID NO 136
<211> LENGTH: 130
<212> TYPE: PRT
<213> ORGANISM: Clitoria ternatea

<400> SEQUENCE: 136

Met Ala Phe Ala Arg Leu Ala Val Ile Phe Phe Leu Ala Ala Ser Val
1               5                   10                  15

Met Phe Ala Val Lys Glu Thr Glu Ala Gly Ile Pro Cys Gly Gly Ser
                20                  25                  30

Cys Val Tyr Ile Pro Cys Thr Val Thr Ala Leu Leu Gly Cys Ser Cys
            35                  40                  45

Lys Asp Lys Val Cys Tyr Lys Asn His Val Ile Ala Ala Glu Ala Asn
        50                  55                  60

Ile Val Asp Asp His His Leu Leu Cys Gln Ser His Glu Asp Cys Phe
65                  70                  75                  80

Lys Lys Gly Thr Gly Asn Phe Cys Ala Pro Phe Leu Gly His Asp Val
                85                  90                  95

Lys Tyr Gly Trp Cys Phe Arg Ala Glu Ser Glu Gly Phe Leu Leu Lys
            100                 105                 110

Asp Phe Leu Lys Thr Pro Val Asp Ile Leu Lys Thr Ala Asn Ala Ile
        115                 120                 125

Arg Asn
130

<210> SEQ ID NO 137
<211> LENGTH: 512
<212> TYPE: DNA
<213> ORGANISM: Clitoria ternatea

<400> SEQUENCE: 137
gggggtaaca aatactacta cttccttgtt tccatcaact gaatcaaaaa atggcttttg     60
ccaggcttgc tgtcatattc ttccttgctg cctctgttat gttcgctgtg aaggaaaccg    120
aagctggtat tccatgtgga ggatcttgtg tttacattcc atgcactgta actgcacttc    180
tgggttgctc ctgcaaggat aaagtttgtt acaaaaatca tgttattgca gctgaagcaa    240
```

```
acatcgtaga tgatcatcat cttttgtgtc aatctcatga agactgtttc aagaaaggaa      300
ctggaaactt ctgtgcacct tccttggac atgatgttaa gtatggatgg tgcttccgtg       360
ctgaatctga aggattttg ttgaaggatt tcttaaagac accagtagat attttaaaga       420
cagctaatgc aatccgtaat taaaaatatt aaaatgtatg atgcattctc taccctttta      480
aataaaaata aatgatgcat ctactaaaaa aa                                    512

<210> SEQ ID NO 138
<211> LENGTH: 123
<212> TYPE: PRT
<213> ORGANISM: Clitoria ternatea

<400> SEQUENCE: 138

Met Ala Ser Leu Arg Ile Ala Pro Leu Ala Leu Phe Phe Phe Leu Ala
1               5                   10                  15

Ala Ser Val Met Phe Thr Val Glu Lys Thr Glu Ala Gly Ile Pro Cys
            20                  25                  30

Gly Glu Ser Cys Val Phe Ile Pro Cys Ile Thr Ala Ala Ile Gly Cys
        35                  40                  45

Ser Cys Lys Ser Lys Val Cys Tyr Arg Asn His Val Ile Ala Ala Glu
    50                  55                  60

Ala Lys Thr Met Asp Asp His His Leu Leu Cys Gln Ser His Glu Asp
65                  70                  75                  80

Cys Ile Thr Lys Gly Thr Gly Asn Phe Cys Ala Pro Phe Pro Asp Gln
                85                  90                  95

Asp Ile Lys Tyr Gly Trp Cys Phe Arg Ala Glu Ser Glu Gly Phe Leu
            100                 105                 110

Leu Lys Asp His Leu Lys Met Ser Ile Thr Asn
        115                 120

<210> SEQ ID NO 139
<211> LENGTH: 490
<212> TYPE: DNA
<213> ORGANISM: Clitoria ternatea

<400> SEQUENCE: 139
ggggcaaagc atcaacttaa tccattaatg gcttcccttc gcattgctcc tctcgctctc      60 ttcttttcc ttgccgcttc ggttatgttt acagtggaga agactgaagc cggtatccct       120
tgtggagaat cttgtgtatt tattccatgc ataacagcag ccatcggttg ttcttgtaaa      180
agcaaagttt gctatcgaaa ccatgtcatt gcagctgagg caaagacaat ggatgatcat      240
catctcttat gtcaatctca tgaagattgc atcactaaag gaactggaaa cttttgtgct      300
cctttccctg atcaagatat taaatatggt tggtgtttcc gtgctgagtc tgaaggattt      360
ctgttgaaag accacttaaa gatgtctatc accaactgaa agtagtcatg tatgcataat      420
gaatctacta ttacaaaaag atacacatga tgcatgtact atcttaaata aatggttgtt      480
ttaatttcat                                                             490

<210> SEQ ID NO 140
<211> LENGTH: 124
<212> TYPE: PRT
<213> ORGANISM: Clitoria ternatea

<400> SEQUENCE: 140

Trp Leu Pro Leu Arg Ile Ala Pro Phe Ala Val Phe Leu Phe Leu Ala
1               5                   10                  15
```

```
Ala Ser Val Met Phe Ala Val Glu Lys Thr Gln Ala Gly Val Ile Pro
            20                  25                  30

Cys Gly Glu Ser Cys Val Phe Ile Pro Cys Ile Ser Thr Val Ile Gly
            35                  40                  45

Cys Ser Cys Lys Asn Lys Val Cys Tyr Arg Asn His Val Ile Ala Ala
 50                  55                  60

Glu Ala Lys Thr Met Asp Glu His Leu Leu Cys Gln Ser His Glu
 65                  70                  75                  80

Asp Arg Ile Ala Lys Gly Thr Gly Asn Phe Cys Ala Pro Phe Pro Asp
                 85                  90                  95

Gln Asp Ile Lys Tyr Gly Trp Cys Phe Arg Ala Glu Ser Glu Gly Phe
                100                 105                 110

Met Leu Lys Asp His Leu Lys Met Ser Ile Thr Asn
            115                 120
```

<210> SEQ ID NO 141
<211> LENGTH: 464
<212> TYPE: DNA
<213> ORGANISM: Clitoria ternatea
<220> FEATURE:
<221> NAME/KEY: misc_feature
<222> LOCATION: 464
<223> OTHER INFORMATION: n = A,T,C or G

<400> SEQUENCE: 141

```
tggcttcccc ttcgcattgc tcctttcgct gtcttccttt tccttgctgc ttcggttatg      60
tttgcagtgg agaagactca agcaggtgtc attccttgcg gagaatcttg tgtatttatt     120
ccatgtatat caacagttat cggctgttct tgtaagaaca agtttgcta tcgaaaccat      180
gttattgcag ctgaggcaaa gacaatggat gagcatcttc tcttatgtca atctcatgaa     240
gatcgcatcg ctaaaggaac tggaaacttt tgtgctcctt tccctgatca agatattaaa     300
tatggttggt gtttccgtgc tgagtctgaa ggattcatgt tgaaagacca cttgaagatg     360
tctatcacca actgaaagta gtcatgcatg ataatgaat ctaatactaa aaaaatgcac      420
atgatgcatg tactatctta aataaatggc tcttttagtg ggan                      464
```

<210> SEQ ID NO 142
<211> LENGTH: 124
<212> TYPE: PRT
<213> ORGANISM: Clitoria ternatea

<400> SEQUENCE: 142

```
Met Ala Ser Leu Arg Ile Ala Pro Phe Ala Val Phe Leu Phe Leu Ala
  1               5                  10                  15

Ala Ser Val Met Phe Ala Val Glu Lys Thr Gln Ala Gly Val Ile Pro
            20                  25                  30

Cys Gly Glu Ser Cys Val Phe Ile Pro Cys Ile Ser Thr Val Ile Gly
            35                  40                  45

Cys Ser Cys Lys Asn Lys Val Cys Tyr Arg Asn His Val Ile Ala Ala
 50                  55                  60

Glu Ala Lys Thr Met Asp Glu His Leu Leu Cys Gln Ser His Glu
 65                  70                  75                  80

Asp Cys Ile Ala Lys Gly Thr Gly Asn Phe Cys Ala Pro Phe Pro Asp
                 85                  90                  95

Gln Asp Ile Lys Tyr Gly Trp Cys Phe Arg Ala Glu Ser Glu Gly Phe
                100                 105                 110

Met Leu Lys Asp His Leu Lys Met Ser Ile Thr Asn
            115                 120
```

<210> SEQ ID NO 143
<211> LENGTH: 507
<212> TYPE: DNA
<213> ORGANISM: Clitoria ternatea

<400> SEQUENCE: 143

```
gggagagcaa agtcattgct tattttcatc aaattatggc ttcccttcgc attgctcctt    60
tcgctgtctt cctttccctt gctgcttcgg ttatgtttgc agtggagaag actcaagcag   120
gtgtcattcc ttgcggagaa tcttgtgtat ttattccatg tatatcaaca gttatcggct   180
gttcttgtaa gaacaaagtt tgctatcgaa accatgttat tgcagctgag gcaaagacaa   240
tggatgagca tcttctctta tgtcaatctc atgaagattg catcgctaaa ggaactggaa   300
actttttgtgc tcctttcct gatcaagata ttaaatatgg ttggtgtttc cgcgctgagt   360
ctgaaggatt catgttgaaa gaccacttga agatgtctat caccaactga agtagtcat   420
gcatggataa tgaatctaat actaaaaaaa tgcacatgat gcatgtacta tcttaaataa   480
atggctcttt tagtgtctat tgttagc                                       507
```

<210> SEQ ID NO 144
<211> LENGTH: 123
<212> TYPE: PRT
<213> ORGANISM: Clitoria ternatea

<400> SEQUENCE: 144

Met Ala Ser Leu Arg Ile Ala Pro Leu Ala Leu Phe Phe Phe Leu Ala
1               5                   10                  15

Ala Ser Val Met Phe Thr Val Glu Lys Thr Glu Ala Gly Ile Pro Cys
            20                  25                  30

Gly Glu Ser Cys Val Phe Ile Pro Cys Ile Thr Gly Ala Ile Gly Cys
        35                  40                  45

Ser Cys Lys Ser Lys Val Cys Tyr Arg Asn His Val Ile Ala Ala Glu
    50                  55                  60

Ala Lys Thr Met Asp Asp His His Leu Leu Cys Gln Ser His Glu Asp
65                  70                  75                  80

Cys Ile Thr Lys Gly Thr Gly Asn Phe Cys Ala Ser Phe Pro Glu Gln
                85                  90                  95

Asp Ile Lys Tyr Gly Trp Cys Phe Arg Ala Glu Ser Glu Gly Phe Met
            100                 105                 110

Leu Lys Asp His Leu Lys Met Ser Val Thr Asn
        115                 120

<210> SEQ ID NO 145
<211> LENGTH: 499
<212> TYPE: DNA
<213> ORGANISM: Clitoria ternatea

<400> SEQUENCE: 145

```
ggggatcgca aagcatcaac ttaatccatt aatggcttcc cttcgcattg ctcctctcgc    60
tctcttcttt ttccttgccg cttcggttat gtttacagtg gagaagactg aagccggtat   120
cccttgtgga gaatcttgtg tatttattcc atgcataaca ggagccatcg gttgttcttg   180
taaaagcaaa gtttgctatc gaaaccatgt cattgcagct gaggcaaaga caatggatga   240
tcatcatctc ttatgtcaat ctcatgaaga ttgcatcact aaaggaactg gaaactttg   300
tgcttctttt cctgaacaag atattaaata tggttggtgt ttccgtgctg agtctgaagg   360
attcatgttg aaagatcatt taaagatgtc tgtcaccaac tgaaagtagt catgtatgca   420
```

```
taatgaatct actattacaa aaagatacac atgatgcatg tactatctta aataaatggt    480
tgttttaatt tctattgtt                                                 499
```

<210> SEQ ID NO 146
<211> LENGTH: 123
<212> TYPE: PRT
<213> ORGANISM: Clitoria ternatea

<400> SEQUENCE: 146

```
Met Ala Ser Leu Arg Ile Ala Pro Leu Ala Leu Phe Phe Phe Leu Ala
 1               5                  10                  15

Ala Ser Val Met Phe Thr Val Glu Lys Thr Glu Ala Gly Ile Pro Cys
             20                  25                  30

Gly Glu Ser Cys Val Phe Ile Pro Cys Ile Thr Gly Ala Ile Gly Cys
         35                  40                  45

Ser Cys Lys Ser Lys Val Cys Tyr Arg Asn His Val Ile Ala Ala Glu
 50                  55                  60

Ala Lys Thr Met Asp Asp His His Leu Leu Cys Gln Ser His Glu Asp
65                  70                  75                  80

Cys Ile Thr Lys Gly Thr Gly Asn Phe Cys Ala Pro Phe Pro Asp Gln
                 85                  90                  95

Asp Ile Lys Tyr Gly Trp Cys Phe Arg Ala Glu Ser Glu Gly Phe Val
            100                 105                 110

Leu Lys Asp His Leu Lys Met Ser Ile Thr Asn
        115                 120
```

<210> SEQ ID NO 147
<211> LENGTH: 496
<212> TYPE: DNA
<213> ORGANISM: Clitoria ternatea

<400> SEQUENCE: 147

```
gggggcaaag catcaactta atccattaat ggcttccctt cgcattgctc ctctcgctct     60 cttcttttc cttgccgctt cggttatgtt tacagtggag aagactgaag ccggtatccc    120
ttgtggagaa tcttgtgtat ttattccatg cataacagga gccatcggtt gttcttgtaa    180
aagcaaagtt tgctatcgaa accatgtcat tgcagctgag gcaaagacaa tggatgatca    240
tcatctctta tgtcaatctc atgaagattg catcactaaa ggaactggaa acttttgtgc    300
tcctttccct gatcaagata ttaaatatgg ttggtgtttc cgtgctgagt ctgaaggatt    360
cgtgttgaaa gaccacttaa agatgtctat caccaactga agtagtcat gtatgcataa    420 tgaatctact attacaaaaa gatacacatg atgcatgtac tatcttaaat aaatggttgt    480
tttaatttct attgag                                                   496
```

<210> SEQ ID NO 148
<211> LENGTH: 123
<212> TYPE: PRT
<213> ORGANISM: Clitoria ternatea

<400> SEQUENCE: 148

```
Met Ala Ser Leu Arg Ile Ala Pro Leu Ala Leu Phe Phe Phe Leu Ala
 1               5                  10                  15

Ala Ser Val Met Phe Thr Val Glu Lys Thr Glu Ala Gly Ile Pro Cys
             20                  25                  30

Gly Glu Ser Cys Val Phe Ile Pro Cys Ile Thr Gly Ala Ile Gly Cys
         35                  40                  45
```

Ser Cys Lys Ser Lys Val Cys Tyr Arg Asn His Val Ile Ala Ala Glu
    50                  55                  60

Ala Lys Thr Met Asp Asp His His Leu Leu Cys Gln Ser His Glu Asp
65                  70                  75                  80

Cys Ile Ile Lys Gly Thr Gly Asn Phe Cys Ala Ser Phe Pro Glu Gln
                85                  90                  95

Asp Ile Lys Tyr Gly Trp Cys Phe Arg Ala Glu Ser Glu Gly Phe Met
                100                 105                 110

Leu Lys Asp His Leu Lys Met Ser Ile Thr Asn
                115                 120

<210> SEQ ID NO 149
<211> LENGTH: 495
<212> TYPE: DNA
<213> ORGANISM: Clitoria ternatea

<400> SEQUENCE: 149
ggggaaaagc atcaacttaa tccattaatg cttcccttc gcattgctcc tctcgctctc        60 ttcttttcc ttgccgcttc ggttatgttt acagtggaga agactgaagc cggtatccct       120
tgtggagaat cttgtgtatt tattccatgc ataacaggag ccatcggttg ttcttgtaaa      180
agcaaagttt gctatcgaaa ccatgtcatt gcagctgagg caaagacaat ggatgatcat      240
cacctcttgt gtcaatctca tgaagattgc atcattaaag gaactgggaa cttttgtgct      300
tctttccctg aacaagatat taaatatggt tggtgtttcc gtgctgagtc tgaaggattc      360
atgttgaaag atcatttaaa gatgtctatc accaactgaa agtagtaatg tatgcataat      420
gaatctacta ttacaaaaag atacacatga tgcatgtact atcttaaata aatggttgtt      480
tcaattttta ttgtt                                                       495

<210> SEQ ID NO 150
<211> LENGTH: 123
<212> TYPE: PRT
<213> ORGANISM: Clitoria ternatea

<400> SEQUENCE: 150

Met Ala Ser Leu Arg Ile Ala Pro Leu Pro Leu Phe Phe Phe Leu Ala
1               5                   10                  15

Ala Ser Val Met Phe Thr Val Glu Lys Thr Glu Ala Gly Ile Pro Cys
                20                  25                  30

Gly Glu Ser Cys Val Phe Ile Pro Cys Ile Ser Thr Val Ile Gly Cys
            35                  40                  45

Ser Cys Lys Asn Lys Val Cys Tyr Arg Asn His Val Ile Ala Ala Glu
    50                  55                  60

Ala Lys Thr Met Asp Asp His His Leu Leu Cys Gln Ser His Glu Asp
65                  70                  75                  80

Cys Ile Thr Lys Gly Thr Gly Asn Phe Cys Ala Pro Phe Pro Asp Gln
                85                  90                  95

Asp Ile Lys Tyr Gly Trp Cys Phe Arg Ala Glu Ser Glu Gly Phe Met
                100                 105                 110

Leu Lys Asp His Leu Lys Met Ser Ile Thr Asn
                115                 120

<210> SEQ ID NO 151
<211> LENGTH: 488
<212> TYPE: DNA
<213> ORGANISM: Clitoria ternatea

<400> SEQUENCE: 151

```
gggggcaaag catcaactta atccattaat ggcttcccct cgcattgctc ctctccctct      60 cttcttttc ctcgccgctt cggttatgtt tacagtggag aagactgaag ccggtatccc     120
ttgtggagaa tcttgtgtat ttattccatg tatatcaaca gttatcggct gttcttgtaa     180
gaacaaagtt tgctatcgaa accatgttat tgcagctgag gcaaagacaa tggatgatca     240
ccatctctta tgtcaatctc atgaagattg catcactaaa ggaactggaa acttttgtgc     300
tcctttccct gatcaagata ttaaatatgg ttggtgtttc cgtgctgagt ctgaaggatt     360
catgttgaaa gaccacttaa agatgtctat caccaactga agtagtcat gtatgcataa      420 tgaatctact attacaaaaa gatacacatg atgcatgtac tatcttaaat aaatggttgt     480
tttaattt                                                             488

<210> SEQ ID NO 152
<211> LENGTH: 123
<212> TYPE: PRT
<213> ORGANISM: Clitoria ternatea

<400> SEQUENCE: 152

Met Ala Ser Leu Arg Ile Ala Pro Leu Ala Leu Phe Phe Phe Leu Ala
 1               5                  10                  15

Ala Ser Val Met Phe Thr Val Glu Lys Thr Glu Ala Gly Ile Pro Cys
            20                  25                  30

Gly Glu Ser Cys Val Phe Ile Pro Cys Ile Thr Ala Ala Ile Gly Cys
        35                  40                  45

Ser Cys Lys Ser Lys Val Cys Tyr Arg Asn His Val Ile Ala Ala Glu
    50                  55                  60

Ala Lys Thr Met Asp Asp His His Leu Leu Cys Gln Ser His Glu Asp
65                  70                  75                  80

Cys Ile Thr Lys Gly Ala Gly Asn Phe Cys Ala Pro Phe Pro Asp Gln
                85                  90                  95

Asp Ile Lys Tyr Gly Trp Cys Phe Arg Ala Glu Ser Glu Gly Phe Leu
            100                 105                 110

Leu Lys Asp His Leu Lys Met Ser Ile Thr Asn
        115                 120

<210> SEQ ID NO 153
<211> LENGTH: 499
<212> TYPE: DNA
<213> ORGANISM: Clitoria ternatea

<400> SEQUENCE: 153
gggggcaaag catcaactta atccattaat ggcttcccct cgcattgctc ctctcgctct      60 cttcttttc cttgccgctt cggttatgtt tacagtggag aagactgaag ccggtatccc     120
ttgtggagaa tcttgtgtat ttattccatg cataacagca gccatcggtt gttcttgtaa     180
aagcaaagtt tgctatcgaa accatgtcat tgcagctgag gcaaagacaa tggatgatca     240
tcatctctta tgtcaatctc atgaagattg catcactaaa ggagctggaa acttttgtgc     300
tcctttccct gatcaagata ttaaatatgg ttggtgtttc cgtgctgagt ctgaaggatt     360
tctgttgaaa gaccacttaa agatgtctat caccaactga agtagtcat gtaagcataa      420 tgaatctact attacaaaaa gatacacatg atgcatgtac tatcttaaat aaatggttgt     480
tttaatttct attgttaag                                                 499

<210> SEQ ID NO 154
<211> LENGTH: 126
```

```
<212> TYPE: PRT
<213> ORGANISM: Clitoria ternatea

<400> SEQUENCE: 154

Met Ala Lys Leu Val Pro Leu Ile Val Ile Phe Leu Val Ala Thr Ser
1               5                   10                  15

Val Asp Met Thr Lys Ala Ser Ile Pro Cys Gly Glu Ser Cys Val Tyr
            20                  25                  30

Ile Pro Cys Leu Thr Thr Ile Val Gly Cys Ser Cys Lys Ser Asn Val
        35                  40                  45

Cys Tyr Ser Asn His Val Ile Ala Ala Thr Ala Lys Ser Leu Asp Glu
50                  55                  60

His Arg Leu Leu Cys Gln Ser His Glu Asp Cys Phe Val Lys Gly Thr
65                  70                  75                  80

Gly Asn Phe Cys Ala His Phe Pro Glu Gly Asp Val Ala Tyr Gly Trp
                85                  90                  95

Cys Phe His Ala Glu Ser Glu Gly Tyr Leu Leu Lys Asp Phe Leu Lys
            100                 105                 110

Met Pro Lys Gly Ile Val Lys Lys Pro Met Glu Ile Val Asn
        115                 120                 125

<210> SEQ ID NO 155
<211> LENGTH: 530
<212> TYPE: DNA
<213> ORGANISM: Clitoria ternatea

<400> SEQUENCE: 155
ggggatagca aaacctataa caaatatcag taatcaactt agtcaaataa tggctaaact       60
tgttcctctc attgtgatct tcttggtcgc cacttctgtg gatatgacaa aagctagtat      120
accttgtgga gaatcctgtg tatacattcc atgtttaacg acaattgtcg gatgttcctg      180
taaaagcaat gtttgttata gtaaccatgt cattgctgcc actgcaaaat cattggatga      240
acatcgtctc ttatgtcaat ctcatgaaga ttgtttcgta aaaggaaccg gaaacttttg      300
tgctcatttt cccgaaggag atgttgcata tggttggtgt ttccatgctg aatctgaagg      360
atatttattg aaggactttc taaaaatgcc caaaggcatc gtgaaaaagc ctatggaaat      420
tgtcaactaa aaattatcat gcatgttgca tctatcacac ctttaattaa ataagatgc       480 atctactcct ttaaataatg tcaaaaggct cgagtgctcc tctactaccg                 530

<210> SEQ ID NO 156
<211> LENGTH: 123
<212> TYPE: PRT
<213> ORGANISM: Clitoria ternatea

<400> SEQUENCE: 156

Met Ala Ser Leu Arg Ile Ala Pro Leu Ala Leu Phe Phe Phe Leu Ala
1               5                   10                  15

Ala Ser Val Met Phe Thr Val Glu Lys Thr Glu Ala Gly Ile Pro Cys
            20                  25                  30

Gly Glu Ser Cys Val Phe Ile Pro Cys Ile Thr Gly Ala Ile Gly Cys
        35                  40                  45

Ser Cys Lys Ser Lys Val Cys Tyr Arg Asn His Val Ile Ala Ala Glu
50                  55                  60

Ala Arg Thr Met Asp Asp His Arg Leu Leu Cys Gln Ser His Glu Asp
65                  70                  75                  80

Cys Ile Thr Lys Gly Thr Gly Asn Phe Cys Ala Ser Phe Pro Glu Gln
            85                  90                  95
```

Asp Ile Lys Tyr Gly Trp Cys Phe Arg Ala Glu Ser Glu Gly Phe Met
            100                 105                 110

Leu Lys Asp His Leu Lys Met Ser Val Thr Asn
        115                 120

<210> SEQ ID NO 157
<211> LENGTH: 488
<212> TYPE: DNA
<213> ORGANISM: Clitoria ternatea

<400> SEQUENCE: 157

```
ggggaaaagc atcaacttaa tccattaatg cttcccttc gcattgctcc tctcgctctc      60
ttctttttcc ttgccgcttc ggttatgttt acagtggaga agactgaagc cggtatccct    120
tgtggagaat cttgtgtatt tattccatgc ataacaggag ccatcggttg ttcttgtaaa    180
agcaaagttt gctatcgaaa ccatgtcatt gcagctgagg caaggacaat ggatgatcat    240
cgtctcttat gtcaatctca tgaagattgc atcactaaag gaactggaaa cttttgtgct    300
tcttttcctg aacaagatat taaatatggt tggtgtttcc gtgctgagtc tgaaggattc    360
atgttgaaag atcatttaaa gatgtctgtc accaactgaa agtagtcatg tatgcataat    420
gaatctacta ttacaaaaag atacacatga tgcatgtact atcttaaata aatggttgtt    480
ttaattgc                                                              488
```

<210> SEQ ID NO 158
<211> LENGTH: 124
<212> TYPE: PRT
<213> ORGANISM: Clitoria ternatea

<400> SEQUENCE: 158

Met Ala Ser Leu Arg Ile Ala Pro Phe Ala Val Phe Leu Phe Leu Ala
 1               5                  10                  15

Ala Ser Val Met Phe Ala Val Glu Lys Thr Gln Ala Gly Val Ile Pro
            20                  25                  30

Cys Gly Glu Ser Cys Val Phe Ile Pro Cys Ile Ser Thr Val Ile Gly
        35                  40                  45

Cys Ser Cys Lys Asn Lys Val Cys Tyr Arg Asn His Val Ile Ala Ala
    50                  55                  60

Glu Ala Lys Thr Met Asp Glu His Leu Leu Leu Cys Gln Ser His Glu
65                  70                  75                  80

Asp Cys Ile Ala Lys Gly Thr Gly Asn Phe Cys Ala Pro Phe Pro Asp
                85                  90                  95

Gln Asp Ile Lys Tyr Gly Trp Cys Phe Arg Ala Glu Ser Glu Gly Phe
            100                 105                 110

Met Leu Lys Asp His Leu Lys Met Ser Ile Thr Asn
        115                 120

<210> SEQ ID NO 159
<211> LENGTH: 495
<212> TYPE: DNA
<213> ORGANISM: Clitoria ternatea

<400> SEQUENCE: 159

```
gggggcagag caaagtcatt gcttattttc atcaaattat ggcttccctt cgcattgctc     60
ctttcgctgt cttcctttc cttgctgctt cggttatgtt tgcagtggag aagactcaag    120
caggtgtcat tccttgcgga gaatcttgtg tattttattcc atgtatatca acagttatcg    180
gctgttcttg taagaacaaa gtttgctatc gaaaccatgt tattgcagct gaggcaaaga    240
```

```
caatggatga gcatcttctc ttatgtcaat ctcatgaaga ttgcatcgct aaaggaactg    300 gaaactttg tgctcctttc cctgatcaag atattaaata tggttggtgt ttccgcgctg     360
agtctgaagg attcatgttg aaagaccact tgaagatgtc tatcaccaac tgaaagtagt    420
catgcatgga taatgaatct aatactaaaa aaatgcacat gacgcatgta ctatcttaaa    480
taaatggctc tttta                                                     495
```

<210> SEQ ID NO 160
<211> LENGTH: 124
<212> TYPE: PRT
<213> ORGANISM: Clitoria ternatea

<400> SEQUENCE: 160

```
Met Ala Ser Leu Arg Ile Ala Pro Phe Ala Val Phe Leu Phe Leu Ala
 1               5                  10                  15

Ala Ser Val Met Phe Ala Val Glu Lys Thr Gln Ala Gly Val Ile Pro
                20                  25                  30

Cys Gly Glu Ser Cys Val Phe Ile Pro Cys Ile Ser Thr Val Ile Gly
            35                  40                  45

Cys Ser Cys Lys Asn Lys Val Cys Tyr Arg Asn His Val Ile Ala Ala
        50                  55                  60

Glu Ala Lys Thr Met Asp Glu His Leu Leu Cys Gln Ser His Glu
65                  70                  75                  80

Asp Cys Ile Ala Lys Gly Thr Gly Asn Phe Cys Ala Pro Phe Pro Asp
                85                  90                  95

Gln Asp Ile Lys Tyr Gly Trp Cys Phe Arg Ala Glu Ser Glu Gly Phe
            100                 105                 110

Met Leu Lys Asp His Leu Lys Met Ser Ile Thr Asn
        115                 120
```

<210> SEQ ID NO 161
<211> LENGTH: 498
<212> TYPE: DNA
<213> ORGANISM: Clitoria ternatea

<400> SEQUENCE: 161

```
ggggagagca aagtcattgc ttattttcat caaattatgg cttcccttcg cattgctcct    60
ttcgctgtct tcctttctcct tgctgcttcg gttatgtttg cagtggagaa gactcaagca   120
ggtgtcattc cttgcggaga atcttgtgta tttattccat gtatcaac agttatcggc     180 tgttcttgta agaacaaagt ttgctatcga accatgttta ttgcagctga ggcaaagaca    240
atggatgagc atcttctctt atgtcaatct catgaagatt gcatcgctaa aggaactgga    300
aacttttgtg ctcctttccc tgatcaagat attaaatatg gttggtgttt ccgtgctgag    360
tctgaaggat tcatgttgaa agaccacttg aagatgtcta tcaccaactg aaagtagtca    420
tgcatggata atgaatctaa actaaaaaa atgcacatga tgcatgtact atcttaaata    480
aatggctctt ttagtgtc                                                  498
```

<210> SEQ ID NO 162
<211> LENGTH: 123
<212> TYPE: PRT
<213> ORGANISM: Clitoria ternatea

<400> SEQUENCE: 162

```
Met Ala Ser Leu Arg Ile Ala Pro Leu Ala Leu Ile Phe Phe Leu Ala
 1               5                  10                  15
```

```
Ala Ser Val Met Phe Thr Val Glu Lys Thr Glu Ala Gly Ile Pro Cys
         20                  25                  30

Gly Glu Ser Cys Val Phe Ile Pro Cys Ile Thr Ala Ile Gly Cys
         35                  40                  45

Ser Cys Lys Ser Lys Val Cys Tyr Arg Asn His Val Ile Ala Ala Glu
 50                  55                  60

Ala Lys Thr Met Asp Asp His Leu Leu Cys Gln Ser His Glu Asp
 65              70                  75                  80

Cys Ile Thr Lys Gly Thr Gly Asn Phe Cys Ala Pro Phe Pro Asp Gln
                 85                  90                  95

Asp Ile Lys Tyr Gly Trp Cys Phe Arg Ala Glu Ser Glu Gly Phe Met
                100                 105                 110

Leu Lys Asp His Leu Lys Met Ser Ile Thr Asn
            115                 120
```

<210> SEQ ID NO 163
<211> LENGTH: 495
<212> TYPE: DNA
<213> ORGANISM: Clitoria ternatea

<400> SEQUENCE: 163

```
gggggcaaag catcaactta atccattaat ggcttccctt cgcattgctc ctctcgctct      60
catcttttc  cttgccgctt cggttatgtt tacagtggag aagactgaag ccggtatccc     120
ttgtggagaa tcttgtgtat ttattccatg cataacagga gccatcggtt gttcttgtaa     180
aagcaaagtt tgctatcgaa accatgtcat tgcagctgag gcaaagacaa tggatgatca     240
tcatctctta tgtcaatctc atgaagattg catcactaaa ggaactggaa acttttgtgc     300
tcctttccct gatcaagata ttaaatatgg ttggtgtttc cgtgctgagt ctgaaggatt     360
catgttgaaa gaccacttaa agatgtctat caccaactga agtagtcat  gtatgcataa     420
tgaatctact attacaaaaa gatacacatg atgcatgtac tatcttaaat aaatggttgt     480
tttaatttct attgc                                                      495
```

<210> SEQ ID NO 164
<211> LENGTH: 123
<212> TYPE: PRT
<213> ORGANISM: Clitoria ternatea
<220> FEATURE:
<221> NAME/KEY: VARIANT
<222> LOCATION: 117
<223> OTHER INFORMATION: Xaa = Any Amino Acid

<400> SEQUENCE: 164

```
Met Ala Ser Leu Arg Ile Ala Pro Leu Ala Leu Phe Phe Leu Ala
 1               5                  10                  15

Ala Ser Val Met Phe Thr Val Glu Lys Thr Glu Ala Gly Ile Pro Cys
         20                  25                  30

Gly Glu Ser Cys Val Phe Ile Pro Cys Ile Thr Ala Ala Ile Gly Cys
         35                  40                  45

Ser Cys Lys Ser Lys Val Cys Tyr Arg Asn His Val Ile Ala Ala Glu
 50                  55                  60

Ala Lys Thr Met Asp Asp His Leu Leu Cys Glu Ser His Glu Asp
 65              70                  75                  80

Cys Ile Thr Lys Gly Thr Gly Asn Phe Cys Ala Pro Phe Pro Asp His
                 85                  90                  95

Asp Ile Lys Tyr Gly Trp Cys Phe Arg Ala Glu Ser Glu Gly Phe Leu
                100                 105                 110
```

Leu Lys Asp Pro Xaa Lys Met Ser Ile Thr Asn
        115                 120

<210> SEQ ID NO 165
<211> LENGTH: 402
<212> TYPE: DNA
<213> ORGANISM: Clitoria ternatea
<220> FEATURE:
<221> NAME/KEY: misc_feature
<222> LOCATION: 363, 364
<223> OTHER INFORMATION: n = A,T,C or G

<400> SEQUENCE: 165
aacttaatcc attaatggct tcccttcgca ttgctcctct cgctctcttc tttttccttg    60
ccgcttcggt tatgtttaca gtggagaaga ctgaagccgg tatcccttgt ggagaatctt   120
gtgtatttat tccatgcata acagcagcca tcggttgttc ttgtaaaagc aaagtttgct   180
atcgaaacca tgtcattgca gctgaggcaa agacaatgga tgatcatcat ctcttatgtg   240
aatctcatga agattgcatc actaaaggaa ctggaaactt tgtgctcct ttccctgatc   300 atgatattaa atatggttgg tgtttccgtg ctgagtctga aggatttctg ttgaaagacc   360
ccnnaaagat gtctatcacc aactgaaagt agtcatgtat gc                      402

<210> SEQ ID NO 166
<211> LENGTH: 123
<212> TYPE: PRT
<213> ORGANISM: Clitoria ternatea

<400> SEQUENCE: 166

Met Ala Ser Leu Arg Ile Ala Pro Leu Ala Leu Phe Phe Phe Leu Ala
 1               5                  10                  15

Ala Ser Val Met Phe Thr Val Glu Lys Thr Glu Ala Gly Ile Pro Cys
            20                  25                  30

Gly Glu Ser Cys Val Phe Ile Pro Cys Ile Thr Ala Ala Ile Gly Cys
        35                  40                  45

Ser Cys Lys Ser Lys Val Cys Tyr Arg Asn His Val Ile Ala Ala Glu
    50                  55                  60

Ala Lys Thr Met Asp Asp His His Leu Leu Cys Gln Ser His Glu Asp
65                  70                  75                  80

Cys Ile Thr Lys Gly Thr Gly Asn Phe Cys Ala Pro Phe Pro Asp Gln
                85                  90                  95

Asp Ile Lys Tyr Gly Trp Cys Phe Arg Ala Glu Ser Glu Gly Phe Leu
            100                 105                 110

Leu Lys Asp His Leu Lys Met Ser Ile Thr Asn
        115                 120

<210> SEQ ID NO 167
<211> LENGTH: 486
<212> TYPE: DNA
<213> ORGANISM: Clitoria ternatea

<400> SEQUENCE: 167
taatccatta atggcttccc ttcgcattgc tcctctcgct ctcttctttt ccttgccgc    60 ttcggttatg tttacagtgg agaagactga agccggtatc ccttgtggag aatcttgtgt   120
atttattcca tgcataacag cagccatcgg ttgttcttgt aaaagcaaag tttgctatcg   180
aaaccatgtc attgcagctg aggcaaagac aatggatgat catcatctct atgtcaatc    240 tcatgaagat tgcatcacta aaggaactgg aaactttgt gctccttcc ctgatcaaga   300 tattaaatat ggttggtgtt tccgtgctga gtctgaagga tttctgttga aagaccactt   360

```
aaagatgtct atcaccaact gaaagtagtc atgtatgcat aatggatcta ctattacaaa    420
aagatacaca tgatgcatgt actatcttaa ataaatggtt gttttaattt ctattgttat    480
tttctt                                                                486
```

<210> SEQ ID NO 168
<211> LENGTH: 123
<212> TYPE: PRT
<213> ORGANISM: Clitoria ternatea

<400> SEQUENCE: 168

```
Trp Leu Pro Phe Ala Leu Leu Ser Leu Ser Phe Phe Leu Ala
  1               5                  10                  15

Ala Ser Val Met Phe Thr Val Glu Lys Thr Glu Ala Gly Ile Pro Cys
             20                  25                  30

Gly Glu Ser Cys Val Phe Ile Pro Cys Ile Thr Ala Ala Ile Gly Cys
         35                  40                  45

Ser Cys Lys Ser Lys Val Cys Tyr Arg Asn His Val Ile Ala Ala Glu
     50                  55                  60

Ala Lys Thr Met Asp Asp His His Leu Leu Cys Gln Ser His Glu Asp
 65                  70                  75                  80

Cys Ile Thr Lys Gly Thr Gly Asn Phe Cys Ala Pro Phe Pro Asp Gln
                 85                  90                  95

Asp Ile Lys Tyr Gly Trp Cys Phe Arg Ala Glu Ser Glu Gly Phe Leu
            100                 105                 110

Leu Lys Asp His Leu Lys Met Ser Ile Thr Asn
            115                 120
```

<210> SEQ ID NO 169
<211> LENGTH: 457
<212> TYPE: DNA
<213> ORGANISM: Clitoria ternatea
<220> FEATURE:
<221> NAME/KEY: misc_feature
<222> LOCATION: 417
<223> OTHER INFORMATION: n = A,T,C or G

<400> SEQUENCE: 169

```
aatggcttcc cttcgcattg ctcctctcgc tctcttcttt tttccttgcc gcttcggtta     60
tgtttacagt ggagaagact gaagccggta tcccttgtgg agaatcttgt gtatttattc    120
catgcataac agcagccatc ggttgttctt gtaaaagcaa agtttgctat cgaaaccatg    180
tcattgcagc tgaggcaaag acaatggatg atcatcatct cttatgtcaa tctcatgaag    240
attgcatcac taaggaact ggaaactttt gtgctccttt ccctgatcaa gatattaaat    300
atggttggtg tttccgtgct gagtctgaag gatttctgtt gaaagaccac ttaaagatgt    360
ctatcaccaa ctgaaagtag tcatgtatgc ataatgaatc tactattaca aaaganaca    420 catgatgcat gtactatctt aaataaatgg ttgttttt                             457
```

<210> SEQ ID NO 170
<211> LENGTH: 123
<212> TYPE: PRT
<213> ORGANISM: Clitoria ternatea

<400> SEQUENCE: 170

```
Met Ala Ser Leu Arg Ile Ala Pro Leu Ala Leu Phe Phe Leu Ala
  1               5                  10                  15

Ala Ser Val Met Phe Thr Val Glu Lys Thr Glu Ala Gly Ile Pro Cys
             20                  25                  30
```

```
Gly Glu Ser Cys Val Phe Ile Pro Cys Ile Thr Ala Ala Ile Gly Cys
            35                  40                  45
Ser Cys Lys Ser Lys Val Cys Tyr Arg Asn His Val Ile Ala Ala Glu
 50                  55                  60
Ala Lys Thr Met Asp Asp His His Leu Leu Cys Gln Ser His Glu Asp
 65                  70                  75                  80
Cys Ile Thr Lys Gly Thr Gly Asn Phe Cys Ala Pro Phe Pro Asp Gln
                85                  90                  95
Asp Ile Lys Tyr Gly Trp Cys Phe Arg Ala Glu Ser Glu Gly Phe Leu
            100                 105                 110
Leu Lys Asp His Leu Lys Met Ser Ile Thr Asn
            115                 120
```

<210> SEQ ID NO 171
<211> LENGTH: 473
<212> TYPE: DNA
<213> ORGANISM: Clitoria ternatea

<400> SEQUENCE: 171

```
ggggaagcat caacttaatc cattaatggc ttcccttcgc attgctcctc tcgctctctt    60
cttttcctt gccgcttcgg ttatgtttac agtggagaag actgaagccg gtatcccttg   120
tggagaatct tgtgtattta ttccatgcat aacagcagcc atcggttgtt cttgtaaaag   180
caaagtttgc tatcgaaacc atgtcattgc agctgaggca agacaatgg atgatcatca   240
tctcttatgt caatctcatg aagattgcat cactaaagga actggaaact tttgtgctcc   300
tttccctgat caagatatta aatatggttg gtgtttccgt gctgagtctg aaggatttct   360
gttgaaagac cacttaaaga tgtctatcac caactgaaag tagtcatgta tgcataatga   420
atctactatt acaaaaagat acacatgatg catgtactat cttaaataaa tgg          473
```

<210> SEQ ID NO 172
<211> LENGTH: 104
<212> TYPE: PRT
<213> ORGANISM: Clitoria ternatea

<400> SEQUENCE: 172

```
Met Phe Thr Val Glu Lys Thr Glu Ala Gly Ile Pro Cys Gly Glu Ser
 1               5                  10                  15
Cys Val Phe Ile Pro Cys Ile Thr Ala Ala Ile Gly Cys Ser Cys Lys
            20                  25                  30
Ser Lys Val Cys Tyr Arg Asn His Val Ile Ala Ala Glu Ala Lys Thr
            35                  40                  45
Met Asp Asp His His Leu Leu Cys Gln Ser His Glu Asp Cys Ile Thr
 50                  55                  60
Lys Gly Thr Gly Asn Phe Cys Ala Pro Phe Pro Asp Gln Asp Ile Lys
 65                  70                  75                  80
Tyr Gly Trp Cys Phe Arg Ala Glu Ser Glu Gly Phe Leu Leu Lys Asp
                85                  90                  95
His Leu Lys Met Ser Ile Thr Asn
            100
```

<210> SEQ ID NO 173
<211> LENGTH: 417
<212> TYPE: DNA
<213> ORGANISM: Clitoria ternatea

<400> SEQUENCE: 173

```
cggttatgtt tacagtggag aagactgaag ccggtatccc ttgtggagaa tcttgtgtat      60
ttattccatg cataacagca gccatcggtt gttcttgtaa aagcaaagtt tgctatcgaa     120
accatgtcat tgcagctgag gcaaagacaa tggatgatca tcatctctta tgtcaatctc     180
atgaagattg catcactaaa ggaactggaa acttttgtgc tcctttccct gatcaagata     240
ttaaatatgg ttggtgtttc cgtgctgagt ctgaaggatt tctgttgaaa gaccacttaa     300
agatgtctat caccaactga agtagtcatg tatgcataa tgaatctact attacaaaaa      360
gatacacatg atgcacgtac tatcttaaat aaatggttgt tttaatttct attacga        417

<210> SEQ ID NO 174
<211> LENGTH: 123
<212> TYPE: PRT
<213> ORGANISM: Clitoria ternatea

<400> SEQUENCE: 174

Met Ala Ser Leu Arg Ile Ala Pro Leu Ala Leu Phe Phe Phe Leu Ala
 1               5                  10                  15

Ala Ser Val Met Phe Thr Val Glu Lys Thr Glu Ala Gly Ile Pro Cys
                20                  25                  30

Gly Glu Ser Cys Val Phe Ile Pro Cys Ile Thr Ala Ala Ile Gly Cys
            35                  40                  45

Ser Cys Lys Ser Lys Val Cys Tyr Arg Asn His Val Ile Ala Ala Glu
        50                  55                  60

Ala Lys Thr Met Asp Asp His Leu Leu Cys Gln Ser His Glu Asp
 65                  70                  75                  80

Cys Ile Thr Lys Gly Thr Gly Asn Phe Cys Ala Pro Phe Pro Asp Gln
                85                  90                  95

Asp Ile Lys Tyr Gly Trp Cys Phe Arg Ala Glu Ser Glu Gly Phe Leu
            100                 105                 110

Leu Lys Asp His Leu Lys Met Ser Ile Thr Asn
        115                 120

<210> SEQ ID NO 175
<211> LENGTH: 496
<212> TYPE: DNA
<213> ORGANISM: Clitoria ternatea
<220> FEATURE:
<221> NAME/KEY: misc_feature
<222> LOCATION: 10
<223> OTHER INFORMATION: n = A,T,C or G

<400> SEQUENCE: 175
ggggcaaagn atcaacttaa tccattaatg gcttcccttc gcattgctcc tctcgctctc      60 ttcttttttcc ttgccgcttc ggttatgttt acagtggaga agactgaagc cggtatccct    120
tgtggagaat cttgtgtatt tattccatgc ataacagcag ccatcggttg ttcttgtaaa    180
agcaaagttt gctatcgaaa ccatgtcatt gcagctgagg caaagacaat ggatgatcat    240
catctcttat gtcaatctca tgaagattgc atcactaaag gaactggaaa cttttgtgct    300
cctttccctg atcaagatat taaatatggt tggtgtttcc gtgctgagtc tgaaggattt    360
ctgttgaaag accacttaaa gatgtctatc accaactgaa gtagtcatg tatgcataat     420 gaatctacta ttacaaaaag atacacatga tgcatgtact atcttaaata aatggttgtt    480
ttaatttcta ttgtga                                                    496

<210> SEQ ID NO 176
<211> LENGTH: 124
<212> TYPE: PRT
```

<213> ORGANISM: Clitoria ternatea

<400> SEQUENCE: 176

Met Ala Ser Leu Arg Ile Ala Pro Phe Ala Val Phe Leu Phe Leu Ala
1               5                   10                  15

Ala Ser Val Met Phe Ala Val Glu Lys Thr Gln Ala Gly Val Ile Pro
            20                  25                  30

Cys Gly Glu Ser Cys Val Phe Ile Pro Cys Ile Ser Thr Val Ile Gly
        35                  40                  45

Cys Ser Cys Lys Asn Lys Val Cys Tyr Arg Asn His Val Ile Ala Ala
    50                  55                  60

Glu Ala Lys Thr Met Asp Glu His Leu Leu Leu Cys Gln Ser His Glu
65                  70                  75                  80

Asp Cys Ile Ala Lys Gly Thr Gly Asn Phe Cys Ala Pro Phe Pro Asp
                85                  90                  95

Gln Asp Ile Lys Tyr Gly Trp Cys Phe Arg Ala Glu Ser Glu Gly Phe
            100                 105                 110

Met Leu Lys Asp His Leu Lys Met Ser Ile Thr Asn
        115                 120

<210> SEQ ID NO 177
<211> LENGTH: 505
<212> TYPE: DNA
<213> ORGANISM: Clitoria ternatea

<400> SEQUENCE: 177

```
gggggcagag caaagtcatt gcttattttc atcaaattat ggcttccctt cgcattgctc      60
ctttcgctgt cttccttttc cttgctgctt cggttatgtt tgcagtggag aagactcaag     120
caggtgtcat tccttgcgga gaatcttgtg tatttattcc atgtatatca acagttatcg     180
gctgttcttg taagaacaaa gtttgctatc gaaaccatgt tattgcagct gaggcaaaga     240
caatggatga gcatcttctc ttatgtcaat ctcatgaaga ttgcatcgct aaaggaactg     300
gaaactttg tgctcctttc cctgatcaag atattaaata tggttggtgt ttccgcgctg     360
agtctgaagg attcatgttg aaagaccact tgaagatgtc tatcaccaac tgaaagtagt     420
catgcatgga taatgaatct aatactaaaa aaatgcacat gatgcatgta ctatcttaaa     480
taaatggctc ttttagtgtc tattg                                            505
```

<210> SEQ ID NO 178
<211> LENGTH: 123
<212> TYPE: PRT
<213> ORGANISM: Clitoria ternatea

<400> SEQUENCE: 178

Met Ala Ser Leu Arg Ile Ala Pro Leu Ala Leu Phe Phe Phe Leu Ala
1               5                   10                  15

Ala Ser Val Met Phe Thr Val Glu Lys Thr Gln Ala Gly Ile Pro Cys
            20                  25                  30

Gly Glu Ser Cys Val Phe Ile Pro Cys Ile Thr Gly Ala Ile Gly Cys
        35                  40                  45

Ser Cys Lys Ser Lys Val Cys Tyr Arg Asn His Val Ile Ala Ala Glu
    50                  55                  60

Ala Lys Thr Met Asp Asp His His Leu Leu Cys Gln Ser His Glu Asp
65                  70                  75                  80

Cys Ile Thr Lys Gly Thr Gly Asn Phe Cys Ala Ser Phe Pro Glu Gln
                85                  90                  95

Asp Ile Lys Tyr Gly Trp Cys Phe Arg Ala Glu Ser Glu Gly Phe Met
         100                 105                 110

Leu Lys Asp His Leu Lys Met Ser Val Thr Asn
         115                 120

<210> SEQ ID NO 179
<211> LENGTH: 493
<212> TYPE: DNA
<213> ORGANISM: Clitoria ternatea

<400> SEQUENCE: 179

```
ggggatcgca aagcatcaac ttaatccatt aatggcttcc cttcgcattg ctcctctcgc    60
tctcttcttt ttccttgccg cttcggttat gtttacagtg gagaagactg aagccggtat   120
cccttgtgga gaatcttgtg tatttattcc atgcataaca ggagccatcg gttgttcttg   180
taaaagcaaa gtttgctatc gaaccatgt cattgcagct gaggcaaaga caatggatga   240
tcatcatctc ttatgtcaat ctcatgaaga ttgcatcact aaaggaactg aaacttttg   300
tgcttctttt cctgaacaag atattaaata tggttggtgt ttccgtgctg agtctgaagg   360
attcatgttg aaagatcatt taagatgtc tgtcaccaac tgaaagtagt catgtatgca   420
taatgaatct actattacaa aaagatacac atgatgcatg tactatctta aataaatggt   480
tgttttaatt tgg                                                     493
```

<210> SEQ ID NO 180
<211> LENGTH: 123
<212> TYPE: PRT
<213> ORGANISM: Clitoria ternatea

<400> SEQUENCE: 180

Met Ala Ser Leu Arg Ile Ala Pro Leu Ala Leu Phe Phe Phe Leu Ala
 1               5                  10                  15

Ala Ser Val Met Phe Thr Val Glu Lys Thr Glu Ala Gly Ile Pro Cys
             20                  25                  30

Gly Glu Ser Cys Val Phe Ile Pro Cys Ile Thr Ala Ala Ile Gly Cys
         35                  40                  45

Ser Cys Lys Ser Lys Val Cys Tyr Arg Asn His Val Ile Ala Ala Glu
     50                  55                  60

Ala Lys Thr Met Asp Asp His His Leu Leu Cys Gln Ser His Glu Asp
 65                  70                  75                  80

Cys Ile Thr Lys Gly Thr Gly Asn Phe Cys Ala Pro Phe Pro Asp Gln
                 85                  90                  95

Asp Ile Lys Tyr Gly Trp Cys Phe Arg Ala Glu Ser Glu Gly Phe Leu
         100                 105                 110

Leu Lys Asp His Leu Lys Met Ser Ile Thr Asn
         115                 120

<210> SEQ ID NO 181
<211> LENGTH: 486
<212> TYPE: DNA
<213> ORGANISM: Clitoria ternatea

<400> SEQUENCE: 181

```
ggggaaagca tcaacttaat ccattaatgg cttcccttcg cattgctcct ctcgctctct    60
tcttttcct tgccgcttcg gttatgttta cagtggagaa gactgaagcc ggtatccctt   120
gtggagaatc ttgtgtattt attccatgca taacagcagc catcggttgt tcttgtaaaa   180
gcaaagtttg ctatcgaaac catgtcattg cagctgaggc aaagacaatg gatgatcatc   240
```

```
atctcttatg tcaatctcat gaagattgca tcactaaagg aactggaaac ttttgtgctc    300 cttttccctga tcaagatatt aaatatggtt ggtgtttccg tgctgagtct gaaggatttc    360
tgttgaaaga ccacttaaag atgtctatca ccaactgaaa gtagtcatgt atgcataatg    420
aatctactat tacaaaaaga tacacatgat gcatgtacta tcttaaataa atggttgttt    480
taattt                                                                486
```

<210> SEQ ID NO 182
<211> LENGTH: 123
<212> TYPE: PRT
<213> ORGANISM: Clitoria ternatea

<400> SEQUENCE: 182

```
Met Ala Ser Leu Arg Ile Ala Pro Leu Ala Leu Phe Phe Phe Leu Ala
1               5                   10                  15

Ala Ser Val Met Phe Thr Val Glu Lys Thr Glu Ala Gly Ile Pro Cys
            20                  25                  30

Gly Glu Ser Cys Val Phe Ile Pro Cys Ile Thr Gly Ala Ile Gly Cys
        35                  40                  45

Ser Cys Lys Ser Lys Val Cys Tyr Arg Asn His Val Ile Ala Ala Glu
    50                  55                  60

Ala Lys Thr Met Asp Asp His Leu Leu Cys Gln Ser His Glu Asp
65                  70                  75                  80

Cys Ile Thr Lys Gly Thr Gly Asn Phe Cys Ala Ser Phe Pro Glu Gln
                85                  90                  95

Asp Ile Lys Tyr Gly Trp Cys Phe Arg Ala Glu Ser Glu Gly Phe Met
            100                 105                 110

Leu Lys Asp His Leu Lys Met Ser Val Thr Asn
        115                 120
```

<210> SEQ ID NO 183
<211> LENGTH: 476
<212> TYPE: DNA
<213> ORGANISM: Clitoria ternatea

<400> SEQUENCE: 183

```
gggggcaaag catcaactta atccattaat ggcttcccctt cgcattgctc ctctcgctct    60 cttcttttc cttgccgctt cggttatgtt tacagtggag aagactgaag ccggtatccc    120
ttgtggagaa tcttgtgtat ttattccatg cataacagga gccatcggtt gttcttgtaa    180
aagcaaagtt tgctatcgaa accatgtcat tgcagctgag gcaaagacaa tggatgatca    240
tcatctctta tgtcaatctc atgaagattg catcactaaa ggaactggaa acttttgtgc    300
ttcttttcct gaacaagata ttaaatatgg ttggtgtttc cgtgctgagt ctgaaggatt    360
catgttgaaa gatcatttaa agatgtctgt caccaactga agtagtcat gtatgcataa    420 tgaatctact attacaaaaa gatacacatg atgcatgtac tatcttaaat aaatgg         476
```

<210> SEQ ID NO 184
<211> LENGTH: 124
<212> TYPE: PRT
<213> ORGANISM: Clitoria ternatea

<400> SEQUENCE: 184

```
Met Ala Ser Leu Arg Ile Ala Pro Phe Ala Val Phe Leu Phe Leu Ala
1               5                   10                  15

Ala Ser Val Met Phe Ala Val Glu Lys Thr Gln Ala Gly Val Ile Pro
            20                  25                  30
```

```
Cys Gly Glu Ser Cys Val Phe Ile Pro Cys Ile Ser Thr Val Ile Gly
            35                  40                  45

Cys Ser Cys Lys Asn Lys Val Cys Tyr Arg Asn His Val Ile Ala Ala
    50                  55                  60

Glu Ala Lys Thr Met Asp Glu His Leu Leu Leu Cys Gln Ser His Glu
65                  70                  75                  80

Asp Cys Ile Ala Lys Gly Thr Gly Asn Phe Cys Ala Pro Phe Pro Asp
                85                  90                  95

Gln Asp Ile Lys Tyr Gly Trp Cys Phe Arg Ala Glu Ser Glu Gly Phe
            100                 105                 110

Met Leu Lys Asp His Leu Lys Met Ser Ile Thr Asn
            115                 120

<210> SEQ ID NO 185
<211> LENGTH: 463
<212> TYPE: DNA
<213> ORGANISM: Clitoria ternatea

<400> SEQUENCE: 185
agtcattgct tatttcatc aaattatggc ttcccttcgc attgctcctt tcgctgtctt      60
ccttttcctt gctgcttcgg ttatgtttgc agtggagaag actcaagcag gtgtcattcc    120
ttgcggagaa tcttgtgtat ttattccatg tatatcaaca gttatcggct gttcttgtaa    180
gaacaaagtt tgctatcgaa accatgttat tgcagctgag gcaaagacaa tggatgagca    240
tcttctctta tgtcaatctc atgaagattg catcgctaaa ggaactggaa acttttgtgc    300
tcctttccct gatcaagata ttaaatatgg ttggtgtttc cgtgctgagt ctgaaggatt    360
catgttgaaa gaccacttga agatgtctat caccaactga agtagtcat gcatggataa     420 tgaatctaat actaaaaaaa tgcacatgat gcatgtacta tct                      463

<210> SEQ ID NO 186
<211> LENGTH: 126
<212> TYPE: PRT
<213> ORGANISM: Clitoria ternatea

<400> SEQUENCE: 186

Met Ala Lys Leu Val Pro Leu Ile Val Ile Phe Leu Val Ala Thr Ser
1               5                   10                  15

Val Asp Met Thr Lys Ala Ser Ile Pro Cys Gly Glu Ser Cys Val Tyr
            20                  25                  30

Ile Pro Cys Leu Thr Thr Ile Val Gly Cys Ser Cys Lys Ser Asn Val
            35                  40                  45

Cys Tyr Ser Asn His Val Ile Ala Ala Thr Ala Lys Ser Leu Asp Glu
    50                  55                  60

His Arg Leu Leu Cys Gln Ser His Glu Asp Cys Phe Val Lys Gly Thr
65                  70                  75                  80

Gly Asn Phe Cys Ala His Phe Pro Glu Gly Asp Val Ala Tyr Gly Trp
                85                  90                  95

Cys Phe His Ala Glu Ser Glu Gly Tyr Leu Leu Lys Asp Phe Leu Lys
            100                 105                 110

Met Pro Lys Gly Ile Val Lys Pro Met Glu Ile Val Asn
            115                 120                 125

<210> SEQ ID NO 187
<211> LENGTH: 573
<212> TYPE: DNA
<213> ORGANISM: Clitoria ternatea
```

```
<400> SEQUENCE: 187
gggatagcaa aacctataac aaatatcagt aatcaactta gtcaaataat ggctaaactt      60
gttcctctca ttgtgatctt cttggtcgcc acttctgtgg atatgacaaa agctagtata     120
ccttgtggag aatcctgtgt atacattcca tgtttaacga caattgtcgg atgttcctgt     180
aaaagcaatg tttgttatag taaccatgtc attgctgcca ctgcaaaatc attggatgaa     240
catcgtctct tatgtcaatc tcatgaagat tgtttcgtaa aaggaaccgg aaacttttgt     300
gctcattttc ccgaaggaga tgttgcatat ggttggtgtt tccatgctga atctgaagga     360
tatttattga aggactttct aaaaatgccc aaaggcatcg tgaaaaagcc tatggaaatt     420
gtcaactaaa aattatcatg catgttgcat ctatcacacc tttaattaaa ataagatgca     480
tctactcctt taaataatgt caaaaggctc gagtgctcct ctaccactga atgtaattta     540
caactcccca aataatata tatcaatttg gag                                   573

<210> SEQ ID NO 188
<211> LENGTH: 124
<212> TYPE: PRT
<213> ORGANISM: Clitoria ternatea

<400> SEQUENCE: 188

Met Ala Ser Leu Arg Ile Ala Pro Phe Ala Val Phe Leu Phe Leu Ala
1               5                   10                  15

Ala Ser Val Met Phe Ala Val Glu Lys Thr Gln Ala Gly Val Ile Pro
            20                  25                  30

Cys Gly Glu Ser Cys Val Phe Ile Pro Cys Ile Ser Thr Val Ile Gly
        35                  40                  45

Cys Ser Cys Lys Asn Lys Val Cys Tyr Arg Asn His Val Ile Ala Ala
    50                  55                  60

Glu Ala Lys Thr Met Asp Glu His Leu Leu Leu Cys Gln Ser His Glu
65                  70                  75                  80

Asp Cys Ile Ala Lys Gly Thr Gly Asn Phe Cys Ala Pro Phe Pro Asp
                85                  90                  95

Gln Asp Ile Lys Tyr Gly Trp Cys Phe Arg Ala Glu Ser Glu Gly Phe
            100                 105                 110

Met Leu Lys Asp His Leu Lys Met Ser Ile Thr Asn
        115                 120

<210> SEQ ID NO 189
<211> LENGTH: 499
<212> TYPE: DNA
<213> ORGANISM: Clitoria ternatea

<400> SEQUENCE: 189
gggggcagag caaagtcatt gcttattttc atcaaattat ggcttccctt cgcattgctc      60
ctttcgctgt cttcctttc cttgctgctt cggttatgtt tgcagtggag aagactcaag     120
caggtgtcat tccttgcgga gaatcttgtg tatttattcc atgtatatca acagttatcg     180
gctgttcttg taagaacaaa gtttgctatc gaaatcatgt tattgcagct gaggcaaaga     240
caatggatga gcatcttctc ttatgtcaat ctcatgaaga ttgcatcgct aaaggaactg     300
gaaacttttg tgctcctttc cctgatcaag atattaaata tggttggtgt ttccgtgctg     360
agtctgaagg attcatgttg aaagaccact tgaagatgtc tatcaccaac tgaaagtagt     420
catgcatgga taatgaatct aatactaaaa aaaatgcaca tgatgcatgt actatcttaa     480
ataaatggct cttttagtg                                                  499
```

```
<210> SEQ ID NO 190
<211> LENGTH: 123
<212> TYPE: PRT
<213> ORGANISM: Clitoria ternatea

<400> SEQUENCE: 190

Met Ala Ser Leu Arg Ile Ala Pro Leu Ala Leu Phe Phe Phe Leu Ala
1               5                   10                  15

Ala Ser Val Met Phe Thr Val Glu Lys Thr Glu Ala Gly Ile Pro Cys
            20                  25                  30

Gly Glu Ser Cys Val Phe Ile Pro Cys Ile Thr Gly Ala Ile Gly Cys
        35                  40                  45

Ser Cys Lys Ser Lys Val Cys Tyr Arg Asn His Val Ile Ala Ala Glu
    50                  55                  60

Ala Lys Thr Met Asp Asp His His Leu Leu Cys Gln Ser His Glu Asp
65                  70                  75                  80

Cys Ile Ile Lys Gly Thr Gly Asn Phe Cys Ala Ser Phe Pro Glu Gln
                85                  90                  95

Asp Ile Lys Tyr Gly Trp Cys Phe Arg Ala Glu Ser Glu Gly Phe Met
            100                 105                 110

Leu Lys Asp His Leu Lys Met Ser Ile Thr Asn
        115                 120

<210> SEQ ID NO 191
<211> LENGTH: 481
<212> TYPE: DNA
<213> ORGANISM: Clitoria ternatea

<400> SEQUENCE: 191
ggggcaaagc atcaacttaa tccattaatg gcttcccttc gcattgctcc tctcgctctc      60 ttcttttttcc ttgccgcttc ggttatgttt acagtggaga agactgaagc cggtatccct    120
tgtggagaat cttgtgtatt tattccatgc ataacaggag ccatcggttg ttcttgtaaa     180
agcaaagttt gctatcgaaa ccatgtcatt gcagctgagg caaagacaat ggatgatcat     240
catctcttgt gtcaatctca tgaagattgc atcattaaag gaactggaaa cttttgtgct     300
tctttccctg aacaagatat taaatatggt tggtgtttcc gtgctgagtc tgaaggattc     360
atgttgaaag atcatttaaa gatgtctatc accaactgaa agtagtaatg tatgcataat     420
gaatctacta ttacaaaaag atacacatga tgcatgtact atcttaaata aatggttgtt     480
c                                                                     481

<210> SEQ ID NO 192
<211> LENGTH: 83
<212> TYPE: PRT
<213> ORGANISM: Clitoria ternatea

<400> SEQUENCE: 192

Met Ala Ser Leu Arg Ile Ala Pro Leu Pro Leu Phe Phe Phe Leu Ala
1               5                   10                  15

Ala Ser Val Met Phe Thr Val Glu Lys Thr Glu Ala Gly Ile Pro Cys
            20                  25                  30

Gly Glu Ser Cys Val Phe Ile Pro Cys Ile Ser Thr Val Ile Gly Cys
        35                  40                  45

Ser Cys Lys Asn Lys Val Cys Tyr Arg Asn His Val Ile Ala Ala Glu
    50                  55                  60

Ala Lys Thr Met Asp Asp His His Leu Leu Cys Gln Ser His Glu Asp
65                  70                  75                  80
```

Cys Ile Thr

<210> SEQ ID NO 193
<211> LENGTH: 493
<212> TYPE: DNA
<213> ORGANISM: Clitoria ternatea

<400> SEQUENCE: 193

```
ggggcaaagc atcaacttaa tccattaatg gcttcccttc gcattgctcc tctccctctc      60
ttcttttcc ttgccgcttc ggttatgttt acagtggaga agactgaagc cggtatccct     120
tgtggagaat cttgtgtatt tattccatgt atatcaacag ttatcggctg ttcatgtaag    180
aacaaagttt gctatcgaaa ccatgttatt gcagctgagg caaagacaat ggatgatcat    240
catctcttat gtcaatctca tgaagattgc atcacttaag gaactggaaa cttttgtgct    300
cctttccctg atcaagatat taaatatggt tggtgtttcc gtgctgagtc tgaaggattc    360
atgttgaaag accacttaaa gatgtctatc accaactgaa agtagtcatg tatgcataat    420
gaatctacta ttacaaaaag atacacatga tgcatgtact atcttaaata aatggttgtt    480
ttaatttcta ttg                                                       493
```

<210> SEQ ID NO 194
<211> LENGTH: 126
<212> TYPE: PRT
<213> ORGANISM: Clitoria ternatea
<220> FEATURE:
<221> NAME/KEY: VARIANT
<222> LOCATION: 90
<223> OTHER INFORMATION: Xaa = Any Amino Acid

<400> SEQUENCE: 194

```
Met Ala Lys Leu Val Pro Leu Ile Val Ile Phe Leu Val Ala Thr Ser
 1               5                  10                  15

Val Asp Met Thr Lys Ala Ser Ile Pro Cys Gly Glu Ser Cys Val Tyr
             20                  25                  30

Ile Pro Cys Leu Thr Thr Ile Val Gly Cys Ser Cys Lys Ser Asn Val
         35                  40                  45

Cys Tyr Ser Asn His Val Ile Ala Ala Thr Ala Lys Ser Leu Asp Glu
     50                  55                  60

His Arg Leu Leu Cys Gln Ser His Glu Asp Cys Phe Val Lys Gly Thr
 65                  70                  75                  80

Gly Asn Phe Cys Ala His Phe Pro Glu Xaa Asp Val Ala Tyr Gly Trp
                 85                  90                  95

Cys Phe His Ala Glu Ser Glu Gly Tyr Leu Leu Lys Asp Phe Leu Lys
            100                 105                 110

Met Pro Lys Gly Ile Val Lys Lys Pro Met Glu Ile Val Asn
        115                 120                 125
```

<210> SEQ ID NO 195
<211> LENGTH: 573
<212> TYPE: DNA
<213> ORGANISM: Clitoria ternatea
<220> FEATURE:
<221> NAME/KEY: misc_feature
<222> LOCATION: 317
<223> OTHER INFORMATION: n = A,T,C or G

<400> SEQUENCE: 195

```
ggggatagca aacctataa caaatatcag taatcaactt agtcaaataa tggctaaact       60
tgttcctctc attgtgatct tcttggtcgc cacttctgtg gatatgacaa aagctagtat    120
```

```
accttgtgga gaatcctgtg tatacattcc atgtttaacg acaattgtcg gatgttcctg      180
taaaagcaat gtttgttata gtaaccatgt cattgctgcc actgcaaaat cattggatga      240
acatcgtctc ttatgtcaat ctcatgaaga ttgtttcgta aaaggaaccg gaaacttttg      300
tgctcatttt cccgaangag atgttgcata tggttggtgt ttccatgctg aatctgaagg      360
atatttattg aaggactttc taaaaatgcc caaaggcatc gtgaaaaagc ctatggaaat      420
tgtcaactaa aaattatcat gcatgttgca tctatcacac ctttaattaa aataagatgc      480
atctactcct ttaaataatg tcaaaaggct cgagtgctcc tctactactg aatgtaattt      540
acaactcccc aaaataatac atatcaattt gga                                   573
```

<210> SEQ ID NO 196
<211> LENGTH: 29
<212> TYPE: PRT
<213> ORGANISM: Melicytus ramiflorus

<400> SEQUENCE: 196

Ile Pro Cys Gly Glu Ser Cys Val Phe Ile Pro Cys Ile Ser Ser Ile
 1               5                  10                  15

Val Gly Cys Ser Cys Lys Ser Lys Val Cys Tyr Lys Asn
            20                  25

<210> SEQ ID NO 197
<211> LENGTH: 29
<212> TYPE: PRT
<213> ORGANISM: Melicytus ramiflorus

<400> SEQUENCE: 197

Ile Pro Cys Gly Glu Ser Cys Val Phe Ile Pro Cys Ile Ser Ser Val
 1               5                  10                  15

Val Gly Cys Ser Cys Lys Asn Lys Val Cys Tyr Lys Asn
            20                  25

<210> SEQ ID NO 198
<211> LENGTH: 29
<212> TYPE: PRT
<213> ORGANISM: Viola baoshanensis

<400> SEQUENCE: 198

Ile Pro Cys Gly Glu Ser Cys Val Phe Ile Pro Cys Ile Ser Ser Val
 1               5                  10                  15

Ile Gly Cys Ser Cys Lys Ser Lys Val Cys Tyr Arg Asn
            20                  25

<210> SEQ ID NO 199
<211> LENGTH: 30
<212> TYPE: PRT
<213> ORGANISM: Hybanthus floribundus

<400> SEQUENCE: 199

Gly Ile Pro Cys Gly Glu Ser Cys Val Phe Ile Pro Cys Ile Ser Gly
 1               5                  10                  15

Val Ile Gly Cys Ser Cys Lys Ser Lys Val Cys Tyr Arg Asn
            20                  25                  30

<210> SEQ ID NO 200
<211> LENGTH: 29
<212> TYPE: PRT
<213> ORGANISM: Melicytus ramiflorus

<400> SEQUENCE: 200

```
Ile Pro Cys Gly Glu Gly Cys Val Phe Ile Pro Cys Ile Ser Ser Ile
 1               5                   10                  15

Val Gly Cys Ser Cys Lys Ser Lys Val Cys Tyr Lys Asn
            20                  25
```

<210> SEQ ID NO 201
<211> LENGTH: 30
<212> TYPE: PRT
<213> ORGANISM: Chassalia parviflora

<400> SEQUENCE: 201

```
Gly Ile Pro Cys Gly Glu Ser Cys Val Phe Ile Pro Cys Ile Thr Ser
 1               5                   10                  15

Val Ala Gly Cys Ser Cys Lys Ser Lys Val Cys Tyr Arg Asn
            20                  25              30
```

<210> SEQ ID NO 202
<211> LENGTH: 30
<212> TYPE: PRT
<213> ORGANISM: Viola baoshanensis

<400> SEQUENCE: 202

```
Gly Ile Pro Cys Gly Glu Ser Cys Val Leu Ile Pro Cys Ile Ser Ser
 1               5                   10                  15

Val Ile Gly Cys Ser Cys Lys Ser Lys Val Cys Tyr Arg Asn
            20                  25              30
```

<210> SEQ ID NO 203
<211> LENGTH: 29
<212> TYPE: PRT
<213> ORGANISM: Gloeospermum blakeanum

<400> SEQUENCE: 203

```
Ile Pro Cys Gly Glu Ser Cys Val Phe Ile Pro Cys Ile Ser Ser Val
 1               5                   10                  15

Leu Gly Cys Ser Cys Lys Asn Lys Val Cys Tyr Arg Asn
            20                  25
```

<210> SEQ ID NO 204
<211> LENGTH: 29
<212> TYPE: PRT
<213> ORGANISM: Gloeospermum blakeanum

<400> SEQUENCE: 204

```
Ile Pro Cys Gly Glu Ser Cys Val Phe Ile Pro Cys Ile Ser Ala Val
 1               5                   10                  15

Leu Gly Cys Ser Cys Lys Ser Lys Val Cys Tyr Arg Asn
            20                  25
```

<210> SEQ ID NO 205
<211> LENGTH: 29
<212> TYPE: PRT
<213> ORGANISM: Melicytus ramiflorus

<400> SEQUENCE: 205

```
Ile Pro Cys Gly Glu Ser Cys Val Phe Ile Pro Cys Ile Ser Ser Val
 1               5                   10                  15

Leu Gly Cys Ser Cys Lys Asn Lys Val Cys Tyr Arg Asn
            20                  25
```

<210> SEQ ID NO 206
<211> LENGTH: 28

```
<212> TYPE: PRT
<213> ORGANISM: Viola odorata

<400> SEQUENCE: 206

Pro Cys Gly Glu Ser Cys Val Trp Ile Pro Cys Ile Ser Ser Val Val
 1               5                  10                  15

Gly Cys Ser Cys Lys Ser Lys Val Cys Tyr Lys Asn
            20                  25

<210> SEQ ID NO 207
<211> LENGTH: 29
<212> TYPE: PRT
<213> ORGANISM: Melicytus ramiflorus

<400> SEQUENCE: 207

Ile Pro Cys Gly Glu Ser Cys Val Tyr Ile Pro Cys Ile Ser Ser Leu
 1               5                  10                  15

Leu Gly Cys Ser Cys Lys Ser Lys Val Cys Tyr Lys Asn
                20                  25

<210> SEQ ID NO 208
<211> LENGTH: 30
<212> TYPE: PRT
<213> ORGANISM: Leonia cymosa

<400> SEQUENCE: 208

Gly Ile Pro Cys Gly Glu Ser Cys Val Phe Ile Pro Cys Leu Thr Thr
 1               5                  10                  15

Val Ala Gly Cys Ser Cys Lys Asn Lys Val Cys Tyr Arg Asn
            20                  25                  30

<210> SEQ ID NO 209
<211> LENGTH: 29
<212> TYPE: PRT
<213> ORGANISM: Melicytus ramiflorus

<400> SEQUENCE: 209

Ile Pro Cys Gly Glu Ser Cys Val Phe Ile Pro Cys Leu Thr Ser Ala
 1               5                  10                  15

Ile Gly Cys Ser Cys Lys Ser Lys Val Cys Tyr Lys Asn
                20                  25

<210> SEQ ID NO 210
<211> LENGTH: 30
<212> TYPE: PRT
<213> ORGANISM: Oldenlandia affinis

<400> SEQUENCE: 210

Gly Val Pro Cys Gly Glu Ser Cys Val Phe Ile Pro Cys Leu Thr Ala
 1               5                  10                  15

Val Val Gly Cys Ser Cys Ser Asn Lys Val Cys Tyr Leu Asn
            20                  25                  30

<210> SEQ ID NO 211
<211> LENGTH: 30
<212> TYPE: PRT
<213> ORGANISM: Melicytus ramiflorus

<400> SEQUENCE: 211

Gly Ile Pro Cys Gly Glu Ser Cys Val Phe Ile Pro Cys Leu Thr Ser
 1               5                  10                  15

Ala Ile Gly Cys Ser Cys Lys Ser Lys Val Cys Tyr Arg Asn
            20                  25                  30
```

```
<210> SEQ ID NO 212
<211> LENGTH: 29
<212> TYPE: PRT
<213> ORGANISM: Melicytus ramiflorus

<400> SEQUENCE: 212

Ile Pro Cys Gly Glu Ser Cys Val Phe Ile Pro Cys Ile Ser Ser Ile
 1               5                  10                  15

Val Gly Cys Ser Cys Lys Ser Lys Val Cys Tyr Lys Asn
             20                  25

<210> SEQ ID NO 213
<211> LENGTH: 29
<212> TYPE: PRT
<213> ORGANISM: Melicytus ramiflorus

<400> SEQUENCE: 213

Ile Pro Cys Gly Glu Ser Cys Val Phe Ile Pro Cys Ile Ser Ser Ile
 1               5                  10                  15

Val Gly Cys Ser Cys Lys Ser Lys Val Cys Tyr Lys Asn
             20                  25

<210> SEQ ID NO 214
<211> LENGTH: 30
<212> TYPE: PRT
<213> ORGANISM: Viola odorata

<400> SEQUENCE: 214

Gly Ile Pro Cys Gly Glu Ser Cys Val Tyr Ile Pro Cys Leu Thr Ser
 1               5                  10                  15

Ala Val Gly Cys Ser Cys Lys Ser Lys Val Cys Tyr Arg Asn
             20                  25                  30
```

POLYNUCLEOTIDES ENCODING CYCLOTIDES HAVING NEMATOCIDAL ACTIVITY

CROSS REFERENCE TO RELATED APPLICATIONS

This application claims priority to U.S. Provisional Application No. 61/512,948, filed Jul. 29, 2011, which is hereby incorporated herein in its entirety by reference.

FIELD OF THE INVENTION

The present invention relates to polypeptides having nematicidal activity and polynucleotides that encode the same. Methods of the invention utilize these nematicidal polynucleotides and polypeptides to control plant pests and to increase pest resistance in plants.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 394018SEQLIST.txt, created on Jul. 28, 2011, and having a size of 176 kilobytes and is filed concurrently with the specification. The sequence listing contained in this ASCII formatted document is part of the specification and is herein incorporated by reference in its entirety.

BACKGROUND OF THE INVENTION

Plant pests, including plant-parasitic nematodes, are a major factor in the loss of the world's agricultural crops. Agriculturally significant nematodes include the sedentary endoparasites, such as those found in the genera *Meloidogyne* (root-knot nematodes), *Heterodera*, and *Globedera* (cyst nematodes).

Currently, plant-parasitic nematodes are generally controlled by chemical nematicides, crop rotation, and growing resistant cultivars. The use of chemical nematicides, however, increases costs to farmers and can cause harmful effects on the ecosystem, while consumers and government regulators alike are becoming increasingly concerned with the environmental hazards associated with the production and use of synthetic agrochemicals. At the same time, traditional breeding methods are time-consuming and require continuous effort to maintain disease resistance. See, for example, Grover and Gowthaman (2003) *Curr. Sci.* 84:330-340. Thus, there is substantial interest in developing novel alternatives for the control of plant pathogens that possess a lower risk of pollution and environmental hazards than is characteristic of traditional agrochemical-based methods and that are less cumbersome than conventional breeding techniques.

A number of biotechnology-based strategies, including disruption of the feeding structure of the nematodes by localized expression of phytotoxic gene product(s) have been investigated, but none of them have reached commercial success. Nevertheless, biological control of plant pests of agricultural significance using a microbial agent, such as proteins derived from fungi, bacteria, or insects, affords an environmentally friendly and commercially attractive alternative to synthetic chemical pesticides. Generally speaking, the use of biopesticides presents a lower risk of pollution and environmental hazards, and biopesticides provide greater target specificity than is characteristic of traditional broad-spectrum chemical insecticides. In addition, biopesticides often cost less to produce and thus improve economic yield for a wide variety of crops.

There remains a need for additional biopesticides having nematicidal activity and methods of using such biopesticides to protect crops from plant-parasitic nematodes.

BRIEF SUMMARY OF THE INVENTION

Compositions and methods for protecting a plant from a pest are provided. The compositions comprise cyclotide polypeptides that display pesticidal activity against nematodes, including plant-parasitic nematodes. Polynucleotides comprising nucleotide sequences that encode the presently disclosed cyclotide polypeptides are further provided. Compositions also include expression cassettes comprising a polynucleotide that encodes a cyclotide polypeptide disclosed herein. Plants, plant cells, seeds, and microorganisms comprising the presently disclosed polynucleotides and polypeptides are further provided.

The compositions are useful in methods directed to inducing pest resistance, particularly plant-parasitic nematode resistance, in plants. In particular embodiments, the methods comprise introducing into a plant at least one polynucleotide that encodes a cyclotide polypeptide of the invention. As a result, the cyclotide polypeptide is expressed in the plant, and the pest (e.g., plant parasitic nematode) is exposed to the preferred protein at the site of attack, thereby leading to increased pest resistance. A tissue-preferred promoter may be used to drive expression of a cyclotide polypeptide of the invention in specific plant tissues that are particularly vulnerable to pest attack. For control of nematodes, a root-preferred promoter may be used.

Further provided are biopesticide compositions and formulations and methods for their use in protecting a plant from a pest, particularly a plant-parasitic nematode or insect. In some embodiments, the biopesticide compositions comprise a cyclotide polypeptide of the invention or a microorganism comprising a polynucleotide encoding a cyclotide polypeptide of the invention, in combination with a carrier. Methods of using these compositions to protect a plant from a pest (e.g., a plant-parasitic nematode or insect) comprise applying the biopesticide composition to the environment of a plant pest by, for example, spraying, dusting, broadcasting, or seed coating.

The following embodiments are encompassed by the present invention:

1. An isolated polypeptide comprising an amino acid sequence selected from the group consisting of:
    (a) the amino acid sequence set forth in SEQ ID NO: 1, 2, or 3;
    (b) an amino acid sequence having at least 91% sequence identity to SEQ ID NO: 1, wherein said polypeptide has nematicidal and/or insecticidal activity;
    (c) an amino acid sequence having at least 94% sequence identity to SEQ ID NO: 2, wherein said polypeptide has nematicidal and/or insecticidal activity;
    (d) an amino acid sequence comprising at least 23 consecutive amino acids of SEQ ID NO: 1, wherein said polypeptide has nematicidal and/or insecticidal activity; and
    (e) an amino acid sequence comprising at least 18 consecutive amino acids of SEQ ID NO: 2, wherein said polypeptide has nematicidal and/or insecticidal activity.

2. The isolated polypeptide of embodiment 1, wherein said polypeptide further comprises an N-terminal extension sequence selected from the group consisting of the N-terminal extension sequences identified in Table 1.

3. The isolated polypeptide of embodiment 1 or 2, wherein said polypeptide further comprises an C-terminal extension sequence selected from the group consisting of the C-terminal extension sequences identified in Table 1.

4. The isolated polypeptide of embodiment 1, wherein said polypeptide has nematicidal activity against a nematode that is a member of a *Meloidogyne, Heterodera*, or *Globedera* genera or a nematode selected from the group consisting of *Panagrellus redivivus, Pristionchus pacificus*, and *Caenorhabditis elegans*.

5. The isolated polypeptide of embodiment 1, wherein said polypeptide has insecticidal activity against an insect that is a member of the order Lepidoptera, Coleoptera, or Hemiptera.

6. An isolated polynucleotide comprising a nucleotide sequence selected from the group consisting of:
  (a) a nucleotide sequence encoding an amino acid sequence comprising SEQ ID NO: 1, 2, or 3;
  (b) a nucleotide sequence that hybridizes under stringent conditions to the complement of the nucleotide sequence of (a), wherein said stringent conditions comprise hybridization in 50% formamide, 1 M NaCl, 1% SDS at 37° C., and a wash in 0.1×SSC at 60° C. to 65° C., wherein said polynucleotide encodes a polypeptide having nematicidal and/or insecticidal activity;
  (c) a nucleotide sequence encoding an amino acid sequence having at least 91% sequence identity to SEQ ID NO: 1, wherein said polynucleotide encodes a polypeptide having nematicidal and/or insecticidal activity; and
  (d) a nucleotide sequence encoding an amino acid sequence having at least 94% sequence identity to SEQ ID NO: 2, wherein said polynucleotide encodes a polypeptide having nematicidal and/or insecticidal activity.

7. The isolated polynucleotide of embodiment 6, further comprising a 5' extension sequence selected from the group consisting of the 5' extension sequences identified in Table 2.

8. The isolated polynucleotide of embodiment 6 or 7, further comprising a 3' extension sequence selected from the group consisting of the 3' extension sequences identified in Table 2.

9. The isolated polynucleotide of embodiment 6, wherein said polynucleotide encodes a polypeptide having nematicidal activity against a nematode that is a member of a *Meloidogyne, Heterodera*, or *Globedera* genera or a nematode selected from the group consisting of *Panagrellus redivivus, Pristionchus pacificus*, and *Caenorhabditis elegans*.

10. The isolated polynucleotide of embodiment 6, wherein said polypeptide has insecticidal activity against an insect that is a member of the order Lepidoptera, Coleoptera, or Hemiptera.

11. An expression cassette comprising a polynucleotide of embodiment 6, 7, or 8.

12. The expression cassette of embodiment 11, wherein said polynucleotide is operably linked to a promoter that drives expression in a plant.

13. The expression cassette of embodiment 11, wherein said polynucleotide is operably linked to a promoter that drives expression in a microorganism.

14. A host cell comprising the polynucleotide of embodiment 6, 7, or 8.

15. A host cell comprising the expression cassette of embodiment 11.

16. A plant comprising a heterologous polynucleotide operably linked to a promoter that drives expression in the plant, wherein said heterologous polynucleotide comprises a nucleotide sequence selected from the group consisting of:
  (a) a nucleotide sequence encoding an amino acid sequence comprising SEQ ID NO: 1, 2, or 3;
  (b) a nucleotide sequence that hybridizes under stringent conditions to the complement of the nucleotide sequence of (a), wherein said stringent conditions comprise hybridization in 50% formamide, 1 M NaCl, 1% SDS at 37° C., and a wash in 0.1×SSC at 60° C. to 65° C., and, wherein said polynucleotide encodes a polypeptide having nematicidal and/or insecticidal activity;
  (c) a nucleotide sequence encoding an amino acid sequence having at least 91% sequence identity to SEQ ID NO: 1, wherein said polynucleotide encodes a polypeptide having nematicidal and/or insecticidal activity; and
  (d) a nucleotide sequence encoding an amino acid sequence having at least 94% sequence identity to SEQ ID NO: 2, wherein said polynucleotide encodes a polypeptide having nematicidal and/or insecticidal activity.

17. The plant of embodiment 16, wherein the heterologous polynucleotide further comprises a 5' extension sequence selected from the group consisting of the 5' extension sequences identified in Table 2.

18. The plant of embodiment 16 or 17, wherein the heterologous polynucleotide further comprises a 3' extension sequence selected from the group consisting of the 3' extension sequences identified in Table 2.

19. The plant of embodiment 16, wherein said polynucleotide encodes a polypeptide having nematicidal activity against a nematode that is a member of a *Meloidogyne, Heterodera*, or *Globedera* genera or a nematode selected from the group consisting of *Panagrellus redivivus, Pristionchus pacificus*, and *Caenorhabditis elegans*.

20. The plant of embodiment 16, wherein said polynucleotide encodes a polypeptide having insecticidal activity against an insect that is a member of the order Lepidoptera, Coleoptera, or Hemiptera.

21. The plant of embodiment 16, 17, or 18, wherein said promoter is a root-preferred promoter.

22. The plant of embodiment 16, 17, or 18, wherein said plant is a monocot.

23. The plant of embodiment 22, wherein said monocot is maize, sugarcane, wheat, rice, barley, sorghum, or rye.

24. The plant of embodiment 16, 17, or 18, wherein said plant is a dicot.

25. The plant of embodiment 24, wherein the dicot is soybean, *Brassica*, sunflower, cotton, or alfalfa.

26. A transformed seed of the plant of any one of embodiments 16-25.

27. A method of enhancing pest resistance in a plant, said method comprising providing to said plant a polypeptide selected from the group consisting of:
  (a) the amino acid sequence set forth in SEQ ID NO: 1, 2, or 3;
  (b) an amino acid sequence having at least 91% sequence identity to SEQ ID NO: 1, wherein said polypeptide has nematicidal and/or insecticidal activity;
  (c) an amino acid sequence having at least 94% sequence identity to SEQ ID NO: 2, wherein said polypeptide has nematicidal and/or insecticidal activity;
  (d) an amino acid sequence comprising at least 23 consecutive amino acids of SEQ ID NO: 1, wherein said polypeptide has nematicidal and/or insecticidal activity; and (e) an amino acid sequence comprising at least 18 consecutive amino acids of SEQ ID NO: 2, wherein said polypeptide has nematicidal and/or insecticidal activity.

28. The method of embodiment 27, wherein said polypeptide further comprises an N-terminal extension sequence selected from the group consisting of the N-terminal extension sequences identified in Table 1.

29. The method embodiment 27 or 28, wherein said polypeptide further comprises an C-terminal extension sequence selected from the group consisting of the C-terminal extension sequences identified in Table 1.

30. The method of embodiment 27, wherein said polypeptide has nematicidal activity against a nematode that is a member of a *Meloidogyne, Heterodera*, or *Globedera* genera or a nematode selected from the group consisting of *Panagrellus redivivus, Pristionchus pacificus*, and *Caenorhabditis elegans*.

31. The method of embodiment 27, wherein said polypeptide has insecticidal activity against an insect that is a member of the order Lepidoptera, Coleoptera, or Hemiptera.

32. The method of embodiment 27, wherein said plant is planted in an area of cultivation, wherein said area of cultivation comprises said pest, or wherein environmental conditions in said area of cultivation are conducive to the growth of said pest.

33. The method of embodiment 27, wherein providing the polypeptide comprises introducing into said plant a heterologous polynucleotide comprising a nucleotide sequence selected from the group consisting of:
   (a) a nucleotide sequence encoding an amino acid sequence comprising SEQ ID NO: 1, 2, or 3;
   (b) the nucleotide sequence that hybridizes under stringent conditions to the complement of the nucleotide sequence of (a), wherein said stringent conditions comprise hybridization in 50% formamide, 1 M NaCl, 1% SDS at 37° C., and a wash in 0.1×SSC at 60° C. to 65° C., wherein said polynucleotide encodes a polypeptide having nematicidal and/or insecticidal activity;
   (c) a nucleotide sequence encoding an amino acid sequence having at least 91% sequence identity to SEQ ID NO: 1, wherein said polynucleotide encodes a polypeptide having nematicidal and/or insecticidal activity; and
   (d) a nucleotide sequence encoding an amino acid sequence having at least 94% sequence identity to SEQ ID NO: 2, wherein said polynucleotide encodes a polypeptide having nematicidal and/or insecticidal activity.

34. The method of embodiment 33, wherein the heterologous polynucleotide further comprises a 5' extension sequence selected from the group consisting of the 5' extension sequences identified in Table 2.

35. The method of embodiment 33 or 34, wherein the heterologous polynucleotide further comprises a 3' extension sequence selected from the group consisting of the 3' extension sequences identified in Table 2.

36. The method of embodiment 33, wherein said polynucleotide encodes a polypeptide having nematicidal activity against a nematode that is a member of a *Meloidogyne, Heterodera*, or *Globedera* genera or a nematode selected from the group consisting of *Panagrellus redivivus, Pristionchus pacificus*, and *Caenorhabditis elegans*.

37. The method of embodiment 33, wherein said polynucleotide encodes a polypeptide having insecticidal activity against an insect that is a member of the order Lepidoptera, Coleoptera, or Hemiptera.

38. The method of embodiment 33, 34, or 35, wherein said polynucleotide is stably integrated into the genome of the plant.

39. The method of embodiment 33, 34, or 35, wherein said heterologous polynucleotide is operably linked to a promoter active in said plant.

40. The method of embodiment 39, wherein said promoter is a tissue-preferred promoter.

41. The method of embodiment 40, wherein said tissue-preferred promoter is a root-preferred promoter.

42. A biopesticide composition comprising at least one polypeptide according to embodiment 1.

43. The biopesticide composition of embodiment 42 further comprising a carrier.

44. A method for protecting a plant from a plant pest comprising applying the biopesticide composition according to embodiment 42 to the environment of a plant pest.

45. The method of embodiment 44, wherein said composition is applied by a procedure selected from the group consisting of spraying, dusting, broadcasting, and seed coating.

46. The method of embodiment 44, wherein said plant pest is a nematode.

47. The method of embodiment 46, wherein said nematode is a member of a *Meloidogyne, Heterodera*, or *Globedera* genera.

48. The method of embodiment 44, wherein said plant pest is an insect.

49. The method of embodiment 48, wherein said insect is a member of the order Lepidoptera, Coleoptera, or Hemiptera.

50. A microorganism comprising at least one heterologous polynucleotide operably linked to a promoter that drives expression in the microorganism, wherein said polynucleotide comprises a nucleotide sequence selected from the group consisting of:
   (a) a nucleotide sequence encoding an amino acid sequence comprising SEQ ID NO: 1, 2, or 3;
   (b) a nucleotide sequence that hybridizes under stringent conditions to the complement of the nucleotide sequence of (a), wherein said stringent conditions comprise hybridization in 50% formamide, 1 M NaCl, 1% SDS at 37° C., and a wash in 0.1×SSC at 60° C. to 65° C., wherein said polynucleotide encodes a polypeptide having nematicidal and/or insecticidal activity;
   (c) a nucleotide sequence encoding an amino acid sequence having at least 91% sequence identity to SEQ ID NO: 1, wherein said polynucleotide encodes a polypeptide having nematicidal and/or insecticidal activity; and
   (d) a nucleotide sequence encoding an amino acid sequence having at least 94% sequence identity to SEQ ID NO: 2, wherein said polynucleotide encodes a polypeptide having nematicidal and/or insecticidal activity.

51. The microorganism of embodiment 50, wherein said polynucleotide encodes a polypeptide having nematicidal activity against a nematode that is a member of a *Meloidogyne, Heterodera*, or *Globedera* genera or a nematode selected from the group consisting of *Panagrellus redivivus, Pristionchus pacificus*, and *Caenorhabditis elegans*.

52. The microorganism of embodiment 50, wherein said polynucleotide encodes a polypeptide having insecticidal activity against an insect that is a member of the order Lepidoptera, Coleoptera, or Hemiptera.

53. A biopesticide composition comprising at least one microorganism according to embodiment 50.

54. The composition of embodiment 53 further comprising a carrier.

55. A method for protecting a plant from a pest comprising applying the biopesticide composition according to embodiment 53 to the environment of a plant pest.

56. The method of embodiment 55, wherein said biopesticide composition is applied by a procedure selected from the group consisting of spraying, dusting, broadcasting, and seed coating.

57. The method of embodiment 55, wherein said plant pest is a nematode.

58. The method of embodiment 57, wherein said nematode is a member of a *Meloidogyne, Heterodera*, or *Globedera* genera.

59. The method of embodiment 55, wherein said plant pest is an insect.

60. The method of embodiment 59, wherein said insect is a member of the order Lepidoptera, Coleoptera, or Hemiptera.

61. A method for controlling a pest in an area of cultivation, said method comprising:
   a) evaluating environmental conditions in an area of cultivation for the presence of a pest or conditions conducive to the growth of a pest;
   b) selecting an effective amount of a biopesticide composition, wherein the biopesticide composition is the composition according to embodiment 42 or embodiment 53; and
   c) applying said biopesticide composition to a crop, crop part, seed, or an area of cultivation of said crop.

62. A method for controlling a pest in an area of cultivation, said method comprising:
   a) evaluating environmental conditions in an area of cultivation for the presence of a pest or conditions conducive to the growth of a pest; and
   b) planting the area with crop seeds or plants comprising a heterologous polynucleotide operably linked to a promoter that drives expression in the plant, wherein said heterologous polynucleotide comprises a nucleotide sequence selected from the group consisting of:
      (i) a nucleotide sequence encoding an amino acid sequence comprising SEQ ID NO: 1, 2, or 3;
      (ii) the nucleotide sequence that hybridizes under stringent conditions to the complement of the nucleotide sequence of (i) or (ii), wherein said stringent conditions comprise hybridization in 50% formamide, 1 M NaCl, 1% SDS at 37° C., and a wash in 0.1×SSC at 60° C. to 65° C., and wherein said nucleotide sequence encodes a polypeptide having nematicidal and/or insecticidal activity;
      (iii) a nucleotide sequence encoding an amino acid sequence having at least 91% sequence identity to SEQ ID NO: 1, wherein said polynucleotide encodes a polypeptide having nematicidal and/or insecticidal activity; and
      (vi) a nucleotide sequence encoding an amino acid sequence having at least 94% sequence identity to SEQ ID NO: 2, wherein said polynucleotide encodes a polypeptide having nematicidal and/or insecticidal activity.

63. The method of embodiment 61 or 62, wherein said pest is a nematode.

64. The method of embodiment 63, wherein said nematode is a member of a *Meloidogyne, Heterodera*, or *Globedera* genera.

65. The method of embodiment 61 or 62, wherein said plant pest is an insect.

66. The method of embodiment 65, wherein said insect is a member of the order Lepidoptera, Coleoptera, or Hemiptera.

These and other aspects of the invention are disclosed in more detail in the description of the invention given below.

BRIEF DESCRIPTION OF THE FIGURES

In FIG. 1A, *C. elegans* L1 larvae were incubated with a control sample and photographed 48 hours later. In FIG. 1B, *C. elegans* L1 larvae were incubated with the *Clitoria ternatea* crude total seed protein extract and photographed 48 hours later.

DETAILED DESCRIPTION OF THE INVENTION

Figure 1:
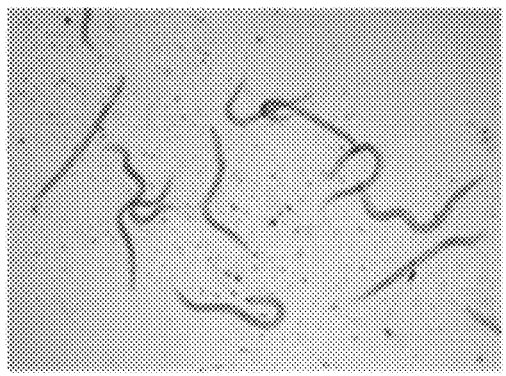
FIG. 1 depicts the results of the nematicidal activity assay for *Clitoria ternatea* crude total seed protein extract.
Figure 1:
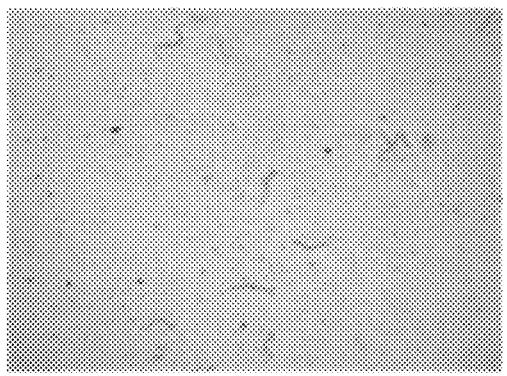

Compositions and methods for protecting plants from pests, particularly nematodes and insects, are provided. The compositions comprise cyclotide proteins that are toxic to nematodes. Accordingly, the invention provides isolated cyclotide polypeptides (e.g., pesticidal cyclotide polypeptides, particularly nematicidal cyclotide polypeptides), isolated polynucleotides that encode nematicidal polypeptides, and expression cassettes comprising the presently disclosed polynucleotides. Biopesticide compositions comprising a cyclotide polypeptide of the invention in combination with a carrier are also provided.

Cyclotides have been isolated from numerous plant species, including members of the Rubiaceae, Violaceae, and Cucurbitaceae families, where they are typically expressed in the leaves, stems and roots. See Craik et al. (2004), Curr. Protein Pept. Sci. 5:297-315. They are small peptides that form highly stable, circular molecules and are associated with a variety of protective activities, including anti-viral, anti-microbial, insecticidal, and nematicidal activities. See Jennings et al. (2001), Proc. Nat'l Acad. Sci. 98:10614-19; Barbeta et al. (2008), Proc. Nat'l Acad. Sci. 105:1221-25; Colgrave et al. (2008), Biochem. 47:5581-89.

Compositions of the invention include isolated cyclotide polypeptides having a sequence set forth in SEQ ID NO: 1 or 2, and fragments and variants thereof (e.g., SEQ ID NO: 3). Preferably, the cyclotide polypeptides of the invention have a head-to-tail cyclized backbone. Additional polypeptides of the invention include isolated polypeptides comprising a sequence set forth in SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 618, 170, 172, 174, 176, 178, 180, 182, 184, 186, 188, 190, 192, or 194, and fragments (e.g., N-terminal extensions, cyclotide domain polypeptides, and C-terminal extensions) and variants thereof.

The invention also includes isolated polynucleotides comprising a sequence that encodes an amino acid sequence of SEQ ID NO: 1, 2, 3, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 618, 170, 172, 174, 176, 178, 180, 182, 184, 186, 188, 190, 192, or 194, and fragments (e.g., encoding N-terminal extensions, cyclotide domain polypeptides, and C-terminal extensions) and variants thereof. In addition, the invention includes polynucleotides comprising a sequence set forth in SEQ ID NO: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 619, 171, 173, 175, 177, 179, 181, 183, 185, 187, 189, 191, 193, or 195, and fragments (e.g., encoding N-terminal extensions, cyclotide domain polypeptides, and C-terminal extensions) and variants thereof. In certain embodiments, the polynucleotides of the invention have been optimized for expression by the cells of a particular organism, e.g., nucleic acid sequences that have been back-translated (i.e., reverse translated) using plant-preferred codons based on the amino acid sequence of a pesticidal polypeptide of the invention.

As used herein, the terms "encoding" or "encoded" when used in the context of a specified polynucleotide mean that the polynucleotide comprises the requisite information to direct translation of the nucleotide sequence into a specified protein. The information by which a protein is encoded is specified by the use of codons. A polynucleotide encoding a protein may comprise non-translated sequences (e.g., introns) within translated regions of the polynucleotide or may lack such intervening non-translated sequences (e.g., as in cDNA).

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, about 4 kb, about 3 kb, about 2 kb, about 1 kb, about 0.5 kb, or about 0.1 kb of nucleotide sequence that naturally flank the polynucleotide in genomic DNA of the cell from which the polynucleotide is derived. A protein that is substantially free of cellular material includes preparations of protein having less than about 30%, about 20%, about 10%, about 5%, or about 1% (by dry weight) of contaminating protein. When the presently disclosed pesticidal proteins or biologically active portions thereof are recombinantly produced, optimally culture medium represents less than about 30%, about 20%, about 10%, about 5%, or about 1% (by dry weight) of chemical precursors or non-protein-of-interest chemicals.

Variants of the disclosed cyclotide polypeptides and polynucleotides encoding such variant polypeptides are also encompassed by the present invention. As used herein, "variants" refers to substantially similar sequences. For polynucleotides, a variant comprises a polynucleotide having deletions (i.e., truncations) at the 5' and/or 3' end; deletion and/or addition of one or more nucleotides at one or more internal sites within the native polynucleotide; and/or a substitution of one or more nucleotides at one or more sites in the native polynucleotide. Variants of interest include those that retain pesticidal (e.g., nematicidal) activity. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of SEQ ID NO: 1, 2, 3, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 618, 170, 172, 174, 176, 178, 180, 182, 184, 186, 188, 190, 192, or 194. Naturally occurring allelic variants can be identified with the use of well-known molecular biology techniques, including, for example, with polymerase chain reaction (PCR) and hybridization techniques as outlined elsewhere herein. Variant polynucleotides also include synthetically derived polynucleotides, such as those generated, for example, by using site-directed mutagenesis but which still encode a protein of the invention or a fragment thereof. Generally, variants of a particular polynucleotide of the invention will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, isolated polynucleotides that encode a polypeptide with a given percent sequence identity to the polypeptide of SEQ ID NO: 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 618, 170, 172, 174, 176, 178, 180, 182, 184, 186, 188, 190, 192, and 194 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 91%, about 92%, about 93%, about 94%, about 95%, about 96%, about 97%, about 98%, about 99% or more sequence identity.

"Variant" polypeptide is intended to mean a protein derived from the native protein or a fragment thereof by deletion (so-called truncation) of one or more amino acids at the N-terminal and/or C-terminal end of the native protein; deletion or addition of one or more amino acids at one or more internal sites in the native protein; and/or substitution of one or more amino acids at one or more sites in the native protein. Variant polypeptides encompassed by the present invention are biologically active, that is they continue to possess a desired biological activity of the native protein. For example, in certain embodiments, polypeptide variants of the invention have pesticidal activity (e.g., nematicidal and/or insecticidal activity). In general, biologically active variants of a polypeptide of the invention will have at least about 91%, about 92%, about 93%, about 94%, about 95%, about 96%, about 97%, about 98%, about 99% or more sequence identity to the amino acid sequence for the native protein (e.g., SEQ ID NO: 1 or 2, or any of the other cyclotide sequences disclosed herein), as determined by sequence alignment programs and parameters described elsewhere herein. A biologically active variant of a protein of the invention may differ from that protein by as few as 20, 15, 14, 13, 12, 11, 10, 9, 8, 7, 6, 5, 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants and fragments of the pesticidal proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the invention include both the naturally occurring sequences as well as mutant forms. Likewise, the proteins of the invention encompass both naturally occurring proteins as well as variations and modified forms thereof. Such variants will continue to possess the desired biological activity (e.g., pesticidal activity, particularly nematicidal and/or insecticidal activity). Obviously, the mutations that will be made in the DNA encoding the variant must not place the sequence out of reading frame and optimally will not create complementary regions that could produce secondary mRNA structure. See, e.g., EP Patent Application Publication No. 75,444.

The deletions, insertions, and substitutions of the protein sequences encompassed herein are not expected to produce radical changes in the characteristics of the protein. Sequence variants likely to have conserved structure and function can be identified by conventional methods. Multi-sequence alignment tools can be used to identify conserved amino acids in protein domains having related function (e.g., a number of cyclotide proteins have been identified, including Kalata B1, B2, B8, Palicourein, Violacin A, Vodo M, Vodo N, Vary A, Cycloviolacin O1 through O25, etc.; see, e.g., Wang et al. (2009), Biophysical J. 97:1471-81; Ireland et al. (2006), Biochem. J. 400:1-12). In general, variation of amino acids at non-conserved positions will typically result in functional variants, while variation of amino acids at positions that are conserved is more constrained, but is sometimes still permissible (e.g., conservative substitutions, and certain non-conservative substitutions may be permissible). Additionally, structural prediction tools such as CABS, ESyPred3D, HHpred, ROBETTA, and WHAT IF can be used to model the structure of protein domains based upon known protein structures (e.g., the structure of Kalata B1 or Cycloviolacin O1), allowing in silico evaluation of the potential effects of introducing amino acid changes into a sequence. Accordingly, using conventional sequence analysis tools, structural prediction tools, and/or screening methods disclosed in the present application, polypeptide variants of the invention having conserved structure and function relative to, e.g., SEQ ID NO: 1, SEQ ID NO: 2, or any other cyclotide sequence disclosed herein, can be identified and tested for function. See, e.g., Simonse et al. (2008), J. Biol. Chem. 283(15):9805-13; Ireland et al. (2006), Biochem. J. 400:1-12). Even when it is difficult to predict the exact effect of the substitution, deletion, or insertion in advance of doing so, one skilled in the art will appreciate that the effect can be evaluated by routine screening assays. That is, the activity can be evaluated by assays that measure pesticidal activity, such as nematicidal activity. Due to their small size, variant cyclotides can be chemically synthesized and readily assayed for activity. See, e.g., Simonse et al. (2008), J. Biol. Chem. 283(15):9805-13.

Variant polynucleotides and proteins also encompass sequences and proteins derived from a mutagenic and recombinogenic procedure such as DNA shuffling. With such a procedure, one or more different pesticidal protein coding sequences can be manipulated to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a gene encoding the cyclotide of SEQ ID NO: 1 or SEQ ID NO: 2 and other known pesticidal cyclotide genes, such as, for example, Kalata B1, B2, B8, Palicourein, Violacin A, Vodo M, Vodo N, Vary A, Cycloviolacin O1 through O25, etc., and other genes encoding cyclotides, including, e.g., SEQ ID NO: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 619, 171, 173, 175, 177, 179, 181, 183, 185, 187, 189, 191, 193, and 195, to obtain a new gene coding for a protein with an improved property of interest, such as increased pesticidal (e.g., nematicidal) activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The invention also encompasses fusion polypeptides in which one or more polypeptides of the invention are fused with at least one polypeptide of interest. In certain embodiments, the fusion polypeptides comprise a heterologous polypeptide of interest having an amino acid sequence that is not substantially homologous to a cyclotide polypeptide of the invention. In this embodiment, the receptor polypeptide and the heterologous polypeptide may or may not be operatively linked. An example of operative linkage is fusion in-frame so that a single polypeptide is produced upon translation. Such fusion polypeptides can, for example, facilitate the purification of a recombinant polypeptide. In another embodiment, the fusion polypeptide may contain sequences required for proper processing (e.g., cyclization).

In certain embodiments, cyclotide fusion proteins of the invention comprise a cyclotide polypeptide, e.g., SEQ ID NO: 1, 2, 3, or any other cyclotide domain sequence disclosed herein, fused to an N-terminal and/or a C-terminal extension. Suitable N-terminal and C-terminal extensions include, e.g., N-terminal and C-terminal polypeptides sequences that naturally flank a cyclotide polypeptide and/or are encoded by a cyclotide gene or mRNA (e.g., any of the N-terminal and C-terminal Extension polypeptides identified in Table 1).

The invention also encompasses polynucleotides that encode a cyclotide fusion protein of the invention. For example, polynucleotides of the invention can comprise a sequence encoding a cyclotide domain and further comprising a 5' and/or a 3' polynucleotide extension encoding an N-terminal and/or a C-terminal extension, respectively. Suitable 5' polynucleotide extensions include, e.g., polynucleotides that encode an N-terminal polypeptide sequence that naturally flanks a cyclotide polypeptide (e.g., polynucleotides encoding an N-terminal extension identified in Table 1, including any of the specific polynucleotide sequences identified in Table 2). Suitable 3' polynucleotide extensions include, e.g., polynucleotides that encode an C-terminal polypeptide sequence that naturally flanks a cyclotide polypeptide (e.g., polynucleotides encoding an C-terminal extension identified in Table 1, including any of the specific polynucleotide sequences identified in Table 2).

Preferred N-terminal and C-terminal extensions include the N-terminal and C-terminal extensions of SEQ ID NOs: 12, 14, 22, 28, 42, and 68, as shown in Table 1. Similarly, preferred 5' and 3' polynucleotide extensions include the 5' and 3' extensions of SEQ ID NOs: 13, 15, 23, 29, 43, and 69, as shown in Table 2. However, the sequences flanking any known cyclotide protein or gene may be suitable depending upon the particular use for the resulting polypeptide or polynucleotide, including any flanking sequences disclosed herein. Without intending to be bound by theory, it is believe that the N-terminal and C-terminal sequences encoded by cyclotide genes are required for proper processing of cyclotides proteins from a linear to circular form.

In certain embodiments, the polypeptides of the invention include a cyclotide domain or variant thereof flanked by N-terminal and C-terminal polypeptide extensions, wherein the extensions originate from the same cyclotide gene or mRNA (e.g., the N-terminal and C-terminal extensions of SEQ ID NO: 12, the N-terminal and C-terminal extensions of SEQ ID NO: 14, the N-terminal and C-terminal extensions of SEQ ID NO: 22, the N-terminal and C-terminal extensions of SEQ ID NO: 28, the N-terminal and C-terminal extensions of SEQ ID NO: 42, or the N-terminal and C-terminal extensions of SEQ ID NO: 68, etc.). In other embodiments, the polypeptides of the invention include a cyclotide domain flanked by N-terminal and C-terminal extensions, wherein the extensions originate from different cyclotide genes or mRNAs. In certain embodiments, the polynucleotides of the invention include a polynucleotide sequence encoding a cyclotide domain flanked by 5' and 3' polynucleotide extensions, wherein the extensions originate from the same cyclotide gene or mRNA (e.g., the 5' and 3' extensions of SEQ ID NO: 13, the 5' and 3' extensions of SEQ ID NO: 15, the 5' and 3' extensions of SEQ ID NO: 23, the 5' and 3' extensions of SEQ ID NO: 29, the 5' and 3' extensions of SEQ ID NO: 43, or the 5' and 3' extensions of SEQ ID NO: 69, etc.). In other embodiments, the polynucleotides of the invention include a polynucleotide sequence encoding a cyclotide domain flanked by 5' and 3' extensions, wherein the extensions originate from different cyclotide gene or mRNA sequences.

TABLE 1

Exemplary Polypeptide Fragments of the Invention

| Sequence Identifier | SEQ ID NO: | N-terminal Extension | Cyclotide Domain | C-terminal Extension |
|---|---|---|---|---|
| pk001.b7 | 4 | 1-23 | 24-54 | 55-119 |
| pk001.c18 | 6 | 1-28 | 29-59 | 60-124 |
| pk001.d16 | 8 | 1-24 | 25-54 | 55-119 |
| pk001.d20 | 10 | 1-28 | 29-58 | 59-112 |
| pk001.e19 | 12 | 1-28 | 29-58 | 59-123 |
| pk001.f13 | 14 | 1-28 | 29-59 | 60-124 |
| pk001.f6 | 16 | 1-24 | 25-54 | 55-119 |
| pk001.g6 | 18 | 1-28 | 29-58 | 59-123 |
| pk001.g8 | 20 | 1-28 | 29-58 | 59-123 |
| pk001.h6 | 22 | 1-22 | 23-52 | 53-126 |
| pk001.i6 | 24 | 1-28 | 29-58 | 59-123 |
| pk001.j1 | 26 | 1-28 | 29-59 | 60-124 |
| pk001.k23 | 28 | 1-28 | 29-58 | 59-123 |
| pk001.l20 | 30 | 1-28 | 29-59 | 60-124 |
| pk001.m13 | 32 | 1-28 | 29-59 | 60-124 |
| pk001.m19 | 34 | 1-28 | 29-59 | 60-124 |
| pk001.n19 | 36 | 1-8 | 9-39 | 40-104 |
| pk001.n23 | 38 | 1-28 | 29-58 | 59-123 |
| pk001.o2 | 40 | 1-22 | 23-52 | 53-126 |
| pk001.o5 | 42 | 1-28 | 29-58 | 59-123 |
| pk002.d3 | 44 | 1-25 | 26-56 | 57-130 |
| pk002.h1 | 46 | 1-28 | 29-58 | 59-123 |
| pk002.h18 | 48 | 1-28 | 29-58 | 59-123 |
| pk002.i6 | 50 | 1-28 | 29-58 | 59-123 |
| pk002.j8 | 52 | 1-28 | 29-58 | 59-123 |
| pk002.k10 | 54 | 1-28 | 29-58 | 59-125 |
| pk002.k14 | 56 | 1-28 | 29-58 | 59-123 |
| pk002.k20 | 58 | 1-40 | 41-71 | 72-136 |
| pk002.l11 | 60 | 1-28 | 29-58 | 59-123 |
| pk002.l14 | 62 | 1-28 | 29-58 | 59-123 |
| pk002.l24 | 64 | 1-28 | 29-59 | 60-124 |
| pk002.n5 | 66 | 1-28 | 29-58 | 59-123 |
| pk002.o12 | 68 | 1-28 | 29-58 | 59-123 |
| pk002.o2 | 70 | 1-28 | 29-58 | 59-123 |
| pk002.o6 | 72 | 1-25 | 26-56 | 57-123 |
| pk002.p4 | 74 | 1-22 | 23-52 | 53-126 |
| pk003.a9 | 76 | 1-28 | 29-58 | 59-123 |
| pk003.b8 | 78 | 1-28 | 29-58 | 59-123 |
| pk003.c21 | 80 | 1-28 | 29-58 | 59-123 |
| pk003.c22 | 82 | 1-28 | 29-58 | 59-123 |
| pk003.d17 | 84 | 1-28 | 29-58 | 59-123 |
| pk003.e22 | 86 | 1-28 | 29-58 | 59-123 |
| pk003.f6 | 88 | 1-5 | 6-35 | 36-89 |
| pk003.i7 | 90 | 1-28 | 29-58 | 59-123 |
| pk003.l23 | 92 | 1-28 | 29-58 | 59-123 |
| pk003.l5 | 94 | 1-28 | 29-59 | 60-124 |
| pk003.n8 | 96 | 1-28 | 29-58 | 59-123 |
| pk004.a10 | 98 | 1-28 | 29-58 | 59-123 |
| pk004.a23 | 100 | 1-28 | 29-59 | 60-124 |
| pk004.a5 | 102 | 1-28 | 29-59 | 60-124 |
| pk004.c11 | 104 | 1-28 | 29-58 | 59-123 |
| pk004.d15 | 106 | 1-28 | 29-59 | 60-124 |
| pk004.d21 | 108 | 1-28 | 29-58 | 59-123 |
| pk004.e2 | 110 | 1-28 | 29-58 | 59-123 |
| pk004.f14 | 112 | 1-28 | 29-58 | 59-123 |
| pk004.g14 | 114 | 1-28 | 29-58 | 59-123 |
| pk004.g23 | 116 | 1-28 | 29-59 | 60-124 |
| pk004.h20 | 118 | 1-28 | 29-58 | 59-123 |
| pk004.k21 | 120 | 1-28 | 29-59 | 60-124 |
| pk004.n7 | 122 | 1-28 | 29-58 | 59-123 |
| pk004.p11 | 124 | 1-22 | 23-52 | 53-126 |
| pk004.p5 | 126 | 1-22 | 23-52 | 53-126 |
| pk005.a23 | 128 | 1-28 | 29-58 | 59-123 |
| pk005.b14 | 130 | 1-28 | 29-58 | 59-123 |
| pk005.c2 | 132 | 1-28 | 29-59 | 60-124 |
| pk005.c24 | 134 | 1-28 | 29-58 | 59-123 |
| pk005.d1 | 136 | 1-25 | 26-56 | 57-130 |
| pk005.d17 | 138 | 1-28 | 29-58 | 59-123 |
| pk005.d18 | 140 | 1-28 | 29-59 | 60-124 |
| pk005.e1 | 142 | 1-28 | 29-59 | 60-124 |
| pk005.e8 | 144 | 1-28 | 29-58 | 59-123 |
| pk005.f20 | 146 | 1-28 | 29-58 | 59-123 |
| pk005.f4 | 148 | 1-28 | 29-58 | 59-123 |
| pk005.g18 | 150 | 1-28 | 29-58 | 59-123 |
| pk005.g20 | 152 | 1-28 | 29-58 | 59-123 |

TABLE 1-continued

Exemplary Polypeptide Fragments of the Invention

| Sequence Identifier | SEQ ID NO: | N-terminal Extension | Cyclotide Domain | C-terminal Extension |
|---|---|---|---|---|
| pk005.g4 | 154 | 1-22 | 23-52 | 53-126 |
| pk005.h11 | 156 | 1-28 | 29-58 | 59-123 |
| pk005.h24 | 158 | 1-28 | 29-59 | 60-124 |
| pk005.j2 | 160 | 1-28 | 29-59 | 60-124 |
| pk005.k2 | 162 | 1-28 | 29-58 | 59-123 |
| pk005.m5 | 164 | 1-28 | 29-58 | 59-123 |
| pk005.p11 | 166 | 1-28 | 29-58 | 59-123 |
| pk006.a22 | 168 | 1-28 | 29-58 | 59-123 |
| pk006.a3 | 170 | 1-28 | 29-58 | 59-123 |
| pk006.c13 | 172 | 1-9 | 10-39 | 30-104 |
| pk006.c8 | 174 | 1-28 | 29-58 | 59-123 |
| pk006.d14 | 176 | 1-28 | 29-59 | 60-124 |
| pk006.d2 | 178 | 1-28 | 29-58 | 59-123 |
| pk006.f10 | 180 | 1-28 | 29-58 | 59-123 |
| pk006.g3 | 182 | 1-28 | 29-58 | 59-123 |
| pk006.h6 | 184 | 1-28 | 29-59 | 60-124 |
| pk006.i3 | 186 | 1-22 | 23-52 | 53-126 |
| pk006.k8 | 188 | 1-28 | 29-59 | 60-124 |
| pk006.l6 | 190 | 1-28 | 29-58 | 59-123 |
| pk006.m1 | 192 | 1-28 | 29-58 | 59-83 |
| pk006.m21 | 194 | 1-22 | 23-52 | 53-126 |

TABLE 2

Exemplary Polynucleotide Fragments of the Invention

| Sequence Identifier | SEQ ID NO: | 5' Extension | Cyclotide Domain | 3' Extension |
|---|---|---|---|---|
| pk001.b7 | 5 | 1-69 | 70-162 | 163-357, 163-445 |
| pk001.c18 | 7 | 1-106, 23-106 | 107-199 | 200-394, 200-639 |
| pk001.d16 | 9 | 1-74, 3-74 | 75-164 | 165-359, 165-459 |
| pk001.d20 | 11 | 1-87, 4-87 | 88-177 | 178-339, 178-456 |
| pk001.e19 | 13 | 1-110, 27-110 | 111-200 | 201-395, 201-485 |
| pk001.f13 | 15 | 1-86, 3-86 | 87-179 | 180-374, 180-464 |
| pk001.f6 | 17 | 1-72 | 73-162 | 163-357, 163-461 |
| pk001.g6 | 19 | 1-98, 15-98 | 99-188 | 189-383, 189-475 |
| pk001.g8 | 21 | 1-87, 4-87 | 88-177 | 178-372, 178-466 |
| pk001.h6 | 23 | 1-115, 50-115 | 116-205 | 206-427, 206-497 |
| pk001.i6 | 25 | 1-101, 18-101 | 102-191 | 192-386, 192-454 |
| pk001.j1 | 27 | 1-119, 36-119 | 120-212 | 213-407, 213-499 |
| pk001.k23 | 29 | 1-111, 28-111 | 112-201 | 202-396, 202-492 |
| pk001.l20 | 31 | 1-115, 32-115 | 116-208 | 209-403, 209-594 |
| pk001.m13 | 33 | 1-122, 39-122 | 123-215 | 216-410, 216-477 |
| pk001.m19 | 35 | 1-122, 39-122 | 123-215 | 216-410, 216-498 |
| pk001.n19 | 37 | 1-29, 6-29 | 30-122 | 123-317, 123-454 |
| pk001.n23 | 39 | 1-85, 2-85 | 86-175 | 176-370, 176-452 |
| pk001.o2 | 41 | 1-117, 52-117 | 118-207 | 208-430, 208-567 |
| pk001.o5 | 43 | 1-112, 29-112 | 113-202 | 203-397, 203-494 |
| pk002.d3 | 45 | 1-124, 50-124 | 125-217 | 218-439, 218-516 |
| pk002.h1 | 47 | 1-112, 29-112 | 113-202 | 203-397, 203-496 |
| pk002.h18 | 49 | 1-111, 28-111 | 112-201 | 202-396, 202-497 |
| pk002.i6 | 51 | 1-112, 29-112 | 113-202 | 203-397, 203-488 |
| pk002.j8 | 53 | 1-113, 30-113 | 114-203 | 204-398, 204-496 |
| pk002.k10 | 55 | 1-134, 51-134 | 135-224 | 225-425, 225-541 |
| pk002.k14 | 57 | 1-111, 28-111 | 112-201 | 202-396, 202-500 |
| pk002.k20 | 59 | 1-146, 27-146 | 147-239 | 240-434, 240-605 |
| pk002.l11 | 61 | 1-112, 29-112 | 113-202 | 203-397, 203-466 |
| pk002.l14 | 63 | 1-112, 29-112 | 113-202 | 203-397, 203-496 |
| pk002.l24 | 65 | 1-122, 39-122 | 123-215 | 216-410, 216-588 |
| pk002.n5 | 67 | 1-111, 28-111 | 112-201 | 202-396, 202-502 |
| pk002.o12 | 69 | 1-112, 29-112 | 113-202 | 203-397, 203-496 |
| pk002.o2 | 71 | 1-110, 27-110 | 111-200 | 201-395, 201-494 |
| pk002.o6 | 73 | 1-114, 40-114 | 115-207 | 208-429, 208-603 |
| pk002.p4 | 75 | 1-117, 52-117 | 118-207 | 208-429, 208-578 |
| pk003.a9 | 77 | 1-112, 29-112 | 113-202 | 203-397, 203-506 |
| pk003.b8 | 79 | 1-112, 29-112 | 113-202 | 203-397, 203-484 |
| pk003.c21 | 81 | 1-111, 28-111 | 112-201 | 202-396, 202-490 |
| pk003.c22 | 83 | 1-112, 29-112 | 113-202 | 203-397, 203-476 |
| pk003.d17 | 85 | 1-112, 29-112 | 113-202 | 203-397, 203-492 |
| pk003.e22 | 87 | 1-110, 27-110 | 111-200 | 201-395, 201-473 |
| pk003.f6 | 89 | 1-19, 5-19 | 20-109 | 110-271, 110-507 |

TABLE 2-continued

Exemplary Polynucleotide Fragments of the Invention

| Sequence Identifier | SEQ ID NO: | 5' Extension | Cyclotide Domain | 3' Extension |
|---|---|---|---|---|
| pk003.i7 | 91 | 1-112, 29-112 | 113-202 | 203-397, 203-496 |
| pk003.l23 | 93 | 1-112, 29-112 | 113-202 | 203-397, 203-495 |
| pk003.l5 | 95 | 1-120, 37-120 | 121-213 | 214-408, 214-484 |
| pk003.n8 | 97 | 1-110, 27-110 | 111-200 | 201-395, 201-487 |
| pk004.a10 | 99 | 1-111, 28-111 | 112-201 | 202-396, 202-488 |
| pk004.a23 | 101 | 1-122, 39-122 | 123-215 | 216-410, 216-607 |
| pk004.a5 | 103 | 1-120, 37-120 | 121-213 | 214-408, 214-512 |
| pk004.c11 | 105 | 1-102, 19-102 | 103-192 | 193-387, 193-466 |
| pk004.d15 | 107 | 1-122, 39-122 | 123-215 | 216-410, 216-499 |
| pk004.d21 | 109 | 1-112, 29-112 | 113-202 | 203-397, 203-483 |
| pk004.e2 | 111 | 1-112, 29-112 | 113-202 | 203-397, 203-504 |
| pk004.f14 | 113 | 1-110, 27-110 | 111-200 | 201-395, 201-494 |
| pk004.g14 | 115 | 1-113, 30-113 | 114-203 | 204-398, 204-504 |
| pk004.g23 | 117 | 1-122, 39-122 | 123-215 | 216-410, 216-601 |
| pk004.h20 | 119 | 1-112, 29-112 | 113-202 | 203-397, 203-490 |
| pk004.k21 | 121 | 1-120, 37-120 | 121-213 | 214-408, 214-505 |
| pk004.n7 | 123 | 1-112, 29-112 | 113-202 | 203-397, 203-498 |
| pk004.p11 | 125 | 1-117, 52-117 | 118-207 | 208-429, 208-577 |
| pk004.p5 | 127 | 1-117, 52-117 | 118-207 | 208-429, 208-578 |
| pk005.a23 | 129 | 1-115, 32-115 | 116-205 | 206-400, 206-499 |
| pk005.b14 | 131 | 1-112, 29-112 | 113-202 | 203-397, 203-491 |
| pk005.c2 | 133 | 1-122, 39-122 | 123-215 | 216-410, 216-500 |
| pk005.c24 | 135 | 1-110, 27-110 | 111-200 | 201-395, 201-494 |
| pk005.d1 | 137 | 1-125, 51-125 | 126-218 | 219-440, 219-512 |
| pk005.d17 | 139 | 1-111, 28-111 | 112-201 | 202-396, 202-490 |
| pk005.d18 | 141 | 1-84 | 85-177 | 178-372, 178-464 |
| pk005.e1 | 143 | 1-119, 36-119 | 120-212 | 213-407, 213-507 |
| pk005.e8 | 145 | 1-115, 32-115 | 116-205 | 206-400, 206-499 |
| pk005.f20 | 147 | 1-112, 29-112 | 113-202 | 203-397, 203-496 |
| pk005.f4 | 149 | 1-111, 28-111 | 112-201 | 202-396, 202-495 |
| pk005.g18 | 151 | 1-112, 29-112 | 113-202 | 203-397, 203-488 |
| pk005.g20 | 153 | 1-112, 29-112 | 113-202 | 203-397, 203-499 |
| pk005.g4 | 155 | 1-115, 50-115 | 116-205 | 206-427, 206-530 |
| pk005.h11 | 157 | 1-111, 28-111 | 112-201 | 202-396, 202-488 |
| pk005.h24 | 159 | 1-122, 39-122 | 123-215 | 216-410, 216-495 |
| pk005.j2 | 161 | 1-120, 37-120 | 121-213 | 214-408, 214-498 |
| pk005.k2 | 163 | 1-112, 29-112 | 113-202 | 203-397, 203-495 |
| pk005.m5 | 165 | 1-98, 15-98 | 99-188 | 189-383, 189-402 |
| pk005.p11 | 167 | 1-94, 11-94 | 95-184 | 185-379, 185-486 |
| pk006.a22 | 169 | 1-86, 3-86 | 87-176 | 177-371, 177-457 |
| pk006.a3 | 171 | 1-109, 26-109 | 110-199 | 200-394, 200-473 |
| pk006.c13 | 173 | 1-32, 6-32 | 33-122 | 123-317, 123-417 |
| pk006.c8 | 175 | 1-111, 28-111 | 112-201 | 202-396, 202-496 |
| pk006.d14 | 177 | 1-122, 39-122 | 123-215 | 216-410, 216-505 |
| pk006.d2 | 179 | 1-115, 32-115 | 116-205 | 206-400, 206-493 |
| pk006.f10 | 181 | 1-110, 27-110 | 111-200 | 201-395, 201-486 |
| pk006.g3 | 183 | 1-112, 29-112 | 113-202 | 203-397, 203-476 |
| pk006.h6 | 185 | 1-109, 26-109 | 110-199 | 200-394, 200-463 |
| pk006.i3 | 187 | 1-114, 49-114 | 115-204 | 205-426, 205-573 |
| pk006.k8 | 189 | 1-122, 39-122 | 123-215 | 216-410, 216-499 |
| pk006.l6 | 191 | 1-111, 28-111 | 112-201 | 202-396, 202-481 |
| pk006.m1 | 193 | 1-111, 28-111 | 112-201 | 202-276, 202-493 |
| pk006.m21 | 195 | 1-115, 50-115 | 116-205 | 206-427, 206-573 |

The polynucleotides of the invention can be used to isolate corresponding sequences from other organisms, particularly other plant species, more particularly other legumes, including Butterfly pea and other Fabaceae family members. In this manner, methods such as PCR, hybridization, and the like can be used to identify such sequences based on their sequence homology to the sequences set forth herein. Sequences isolated based on their sequence identity to the entire sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Functions of orthologs are often highly conserved among species. Thus, isolated polynucleotides that encode for a pesticidal cyclotide protein and which hybridize under stringent conditions to the sequences disclosed herein, or to variants or fragments thereof, are encompassed by the present invention.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the polynucleotides of the invention. Methods for preparation of probes for hybridization and for construction of cDNA and genomic libraries are generally known in the art and are disclosed, e.g., in Sambrook et al. (1989) *Molecular Cloning: A Laboratory Manual* (2d ed., Cold Spring Harbor Laboratory Press, Plainview, N.Y.).

For example, a cyclotide sequence disclosed herein (e.g., any of the sequences identified in Table 2, or a polynucleotide encoding SEQ ID NO: 1 or 2), or one or more portions thereof, may be used as a probe capable of specifically hybridizing to corresponding cyclotide sequences and messenger RNAs. To achieve specific hybridization under a variety of conditions, such probes include sequences that are generally at least about 10 or 20 nucleotides in length. Such probes may be used to amplify corresponding cyclotide family sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook).

Hybridization of polynucleotide sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20× SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to about 12 hours. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that encode a cyclotide protein of the invention and hybridize under stringent conditions to the cyclotide sequences disclosed herein, or to fragments thereof, are encompassed by the present invention.

The following terms are used to describe the sequence relationships between two or more polynucleotides or polypeptides: (a) "reference sequence", (b) "comparison window", (c) "sequence identity", and (d) "percentage of sequence identity."

(a) As used herein, a "reference sequence" is a defined sequence used as a basis for sequence comparison. A reference sequence may be a subset or the entirety of a specified sequence; for example, a segment of a full-length cDNA or gene sequence (e.g., a segment that encodes a protein structural domain), the complete cDNA or gene sequence, a segment of a full-length protein (e.g., a structural domain), or the full-length protein.

(b) As used herein, "comparison window" makes reference to a contiguous and specified segment of a polynucleotide or polypeptide sequence, wherein the sequence in the comparison window may comprise additions or deletions (i.e., gaps) compared to the reference sequence (which does not comprise additions or deletions) for optimal alignment of the two polynucleotides or polypeptides. For polynucleotides, the comparison window is typically at least 20 contiguous nucleotides in length, and optionally can be 30, 40, 50, 100, or longer. For polypeptides, a useful comparison window is either a length corresponding to the full-length protein or an active fragment thereof, such as a structural domain, a functionally conserved sequence, or a sequence involved in important binding interactions.

(c) As used herein, "sequence identity" or "identity" in the context of two polynucleotides or polypeptide sequences makes reference to the residues in the two sequences that are the same when aligned for maximum correspondence over a specified comparison window.

(d) As used herein, "percentage of sequence identity" is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877. Computer implementations of these mathematical algorithms can be utilized for comparison of sequences to determine sequence identity. Such implementations include, but are not limited to: CLUSTAL, ALIGN, GAP, BESTFIT, BLAST, PSI-BLAST, FASTA, and TFASTA. Alignments using these programs can be performed using the default parameters. For closely related sequences, alignment may also be performed manually by inspection.

The polypeptides of the invention can be purified from cells that naturally express them, purified from cells that have been altered to express them (i.e., recombinant cells) or synthesized using polypeptide synthesis techniques that are well known in the art. In certain embodiments, the polypeptides are produced by recombinant DNA methods. In such methods a nucleic acid molecule encoding the polypeptide is cloned into an expression cassette as described more fully herein and expressed in an appropriate host cell according to known methods in the art. The polypeptide is then isolated from the host cells using polypeptide purification techniques well known to those of ordinary skill in the art. The purification process can be monitored using chromatographic methods, Western blot techniques, and/or other standard purification and immunoassay techniques.

The polynucleotides of the present invention can be expressed in a host cell, such as a bacterial, fungal, yeast, insect, mammalian, or preferably plant cells. By "host cell" is meant a cell which comprises a heterologous polynucleotide of the invention. Host cells may be prokaryotic cells, such as *E. coli*, or eukaryotic cells, such as yeast, insect, amphibian, or mammalian cells. In some embodiments, host cells are monocotyledonous or dicotyledonous plant cells.

The polynucleotides of the invention can be provided in expression cassettes for expression in a host cell. The expression cassettes of the invention, and vectors containing such cassettes, find use in generating transformed microorganisms, yeast, animal cells, plants, and plant cells and in practicing the methods disclosed herein (e.g., methods for protecting a plant from a pest). The cassette will include 5' and 3' regulatory sequences operably linked to a polynucleotide of the invention. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide that encodes a polypeptide (e.g., a cyclotide polypeptide of the invention) to be under the transcriptional regulation of the regulatory regions.

The expression cassette will include in the 5'-3' direction of transcription, a transcriptional and translational initiation region (i.e., a promoter), a polynucleotide of the invention, and a transcriptional and translational termination region (i.e., termination region) functional in the host organism. The regulatory regions (i.e., promoters, transcriptional regulatory regions, and translational termination regions) and/or the polynucleotide of the invention may be native/analogous to the host cell or to each other. Alternatively, the regulatory regions and/or the polynucleotide of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

A wide range of promoters are known in the art and can be selected for use in the practice of the invention based on the desired outcome. In addition to the promoter, the expression cassettes may contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989), *Proc. Natl. Acad. Sci. USA* 86:6126-6130) and human immunoglobulin heavy-chain binding protein (BiP) (Macejak et al. (1991), *Nature* 353:90-94).

The optionally included termination region may be native with the transcriptional initiation region, may be native with the operably linked polynucleotide of interest, may be native with the host (e.g., bacteria, yeast, insect, plant), or may be derived from another source (i.e., foreign or heterologous) to the promoter, the polynucleotide of interest, the host, or any combination thereof.

Where appropriate, the polynucleotides may be optimized for increased expression in the transformed organism. For example, the polynucleotides can be synthesized using host-preferred codons for improved expression. Such host-preferred codons are well-known in the art. Additional sequence modifications are known to enhance gene expression in a cellular host, including elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The foregoing list of selectable marker genes is not meant to be limiting. Any selectable marker gene can be used in the present invention.

Prokaryotic cells particularly useful as host cells include various strains of *Escherichia coli*; however, other microbial strains may also be used. In this regard, microbial host organisms of particular interest include yeast, such as *Rhodotorula* spp. (e.g., *R. rubra, R. glutinis, R. marina, R. aurantiaca*), *Aureobasidium* spp. (e.g., *A. pollulans*), *Saccharomyces* spp. (e.g., *S. cerevisiae, S. rosei, S. pretoriensis*), and *Sporobolomyces* spp. (e.g., *S. roseus, S. odorus*), phylloplane organisms such as *Pseudomonas* spp. (e.g., *P. aeruginosa, P. fluorescens, P. syringae*), *Erwinia* spp., and *Flavobacterium* spp., and other such organisms, including *Bacillus* (e.g., *B. thuringiensis, B. subtilis*) and the like.

Other suitable microbial hosts include bacteria such as *Serratia* (e.g., *S. marcescens*), *Klebsiella*, *Xanthomonas* (e.g., *Xanthomonas campestris*), *Streptomyces, Rhizobium* (e.g., *R. melioti*), *Rhodopseudomonas* (e.g., *R. spheroids*), *Methylius, Agrobacterium, Acetobacter* (e.g., *A. xylinum*), *Clavibacter* (e.g., *C. xyli*), *Lactobacillus, Arthrobacter, Azotobacter* (e.g., *A. vinelandii*), *Leuconostoc, Alcaligenes* (e.g., *A. entrophus*), Enterobacteriaceae (e.g., *Shigella, Salmonella*, and *Proteus*), Bacillaceae, Spirillaceae (e.g., photobacterium, *Zymomonas, Aeromonas, Vibrio, Desulfovibrio, Spirillum*), Lactobacillaceae, and Nitrobacteraceae, and fungi, particularly yeast, such as *Cryptococcus* (e.g., *C. albidus, C. diffluens, C. laurentii*), *Kluyveromyces* (e.g., *K. veronae*), *Phycomycetes*, and *Ascomycetes* (e.g., *Schizosaccharomyces*).

Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al. (1977) *Nature* 198:1056), the tryptophan (trp) promoter system (Goeddel et al. (1980) *Nucleic Acids Res.* 8:4057) and the lambda derived PL promoter and N-gene ribosome binding site (Simatake and Rosenberg (1981) *Nature* 292:128). Examples of selection markers for *E. coli* include, for example, genes specifying resistance to ampicillin, tetracycline, or chloramphenicol.

Vectors are commonly used for transformation of prokaryotic organisms. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (see, e.g., Palva et al. (1983) *Gene* 22:229-235 and Mosbach et al. (1983) *Nature* 302:543-545).

Synthesis of heterologous proteins in yeast is also well known. Sherman, F. et al. (1982) *Methods in Yeast Genetics*, Cold Spring Harbor Laboratory, is a well recognized work describing the various methods available to produce the protein in yeast. Two widely utilized yeast systems for production of eukaryotic proteins are *Saccharomyces cerevisia* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

The polynucleotides of the invention can also be ligated to various expression vectors for use in transfecting cell cultures of, for instance, mammalian, insect, or plant origin. As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague et al. (1983) *J. Virol.* 45:773-781). Additionally, gene sequences to control replication in the host cell may be incorporated into the vector such as those found in bovine papilloma virus-type vectors. Saveria-Campo, M., Bovine Papilloma Virus DNA a Eukaryotic Cloning Vector in *DNA Cloning Vol. II a Practical Approach*, D. M. Glover, ed., IRL Pres, Arlington, Va. pp. 213-238 (1985).

In some embodiments, transformed/transfected plant cells are employed as expression systems for production of the proteins of the instant invention. Suitable plant hosts include any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean and plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

For suitable plant-preferred expression cassettes, a wide range of plant promoters are discussed in the review of Potenza et al. (2004) *In Vitro Cell Dev Biol—Plant* 40:1-22, herein incorporated by reference. For example, the nucleic acids can be combined with constitutive, tissue-preferred, or other promoters for expression in plants. Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

In certain embodiments, it may be beneficial to express the gene from an inducible promoter (e.g., a pest-inducible promoter). For expression in plants, for example, the promoter can be a wound-inducible promoter. Wound-inducible promoters may respond to damage caused by insect feeding and include the potato proteinase inhibitor (pin II) promoter (Ryan (1990) *Ann. Rev. Phytopath.* 28: 425-449; Duan et al. (1996) *Nature Biotechnology* 14: 494-498), wun1 and wun2 promoters (U.S. Pat. No. 5,428,148) win1 and win2 promoters (Stanford et al. (1989) *Mol. Gen. Genet.* 215: 200-208), systemin promoter (McGurl et al. (1992) *Science* 225: 1570-1573), WIP1 promoter (Rohmeier et al. (1993) *Plant Mol. Biol.* 22: 783-792; Eckelkamp et al. (1993) *FEBS Letters* 323: 73-76), MPI promoter (Corderok et al. (1994) *Plant J.* 6(2): 141-150), and the like.

Tissue-preferred promoters can be utilized to target enhanced expression of the pesticidal polypeptides of the invention within a particular plant tissue. For example, a tissue-preferred promoter may be used to express a polypeptide of the invention in a plant tissue where disease resistance is particularly important, such as, for example, the roots or the leaves. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254(3):337-343; Russell et al. (1997) *Transgenic Res.* 6(2):157-168; Rinehart et al. (1996) *Plant Physiol.* 112(3): 1331-1341; Van Camp et al. (1996) *Plant Physiol.* 112(2): 525-535; Canevascini et al. (1996) *Plant Physiol.* 112(2): 513-524; Yamamoto et al. (1994) *Plant Cell Physiol.* 35(5): 773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.*

29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Where low level expression is desired, weak promoters can be used. Generally, the term "weak promoter" as used herein refers to a promoter that drives expression of a coding sequence at a low level. By low level expression at levels of about 1/1000 transcripts to about 1/100,000 transcripts to about 1/500,000 transcripts is intended. Alternatively, it is recognized that the term "weak promoters" also encompasses promoters that drive expression in only a few cells and not in others to give a overall low level of expression. Where a promoter drives expression at unacceptably high levels, portions of the promoter sequence can be deleted or modified to decrease expression levels.

Such weak constitutive promoters include, for example, the core of the Rsyn7 promoter (WO 99/43838 and U.S. Pat. No. 6,072,050), the core 35S CaMV promoter, and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142; and 6,177,611; herein incorporated by reference.

Preferred 5' leader sequences useful for expression in plants include potyvirus leaders, such as the TEV leader (Tobacco Etch Virus; Gallie et al. (1995), *Gene* 165(2):233-238), MDMV leader (Maize Dwarf Mosaic Virus; *Virology* 154:9-20), human immunoglobulin heavy-chain binding protein (BiP; Macejak et al. (1991), *Nature* 353:90-94), untranslated leader sequence from the coat protein mRNA of alfalfa mosaic virus (AMV RNA 4; Jobling et al. (1987), *Nature* 325:622-625), tobacco mosaic virus leader (TMV; Gallie et al. (1989), in *Molecular Biology of RNA*, ed. Cech (Liss, New York), pp. 237-256), and maize chlorotic mottle virus leader (MCMV; Lommel et al. (1991), *Virology* 81:382-385). See also, Della-Cioppa et al. (1987) *Plant Physiol.* 84:965-968.

Terminator sequences particularly suitable for inclusion in plant-preferred expression cassettes are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639. The potato proteinase inhibitor II gene (PinII) terminator can also be used. See, for example, Keil et al. (1986) *Nucl. Acids Res.* 14:5641-5650; and An et al. (1989) *Plant Cell* 1:115-122, herein incorporated by reference in their entirety.

Plant-preferred codons for improved expression are known in the art. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference. In addition, marker genes particularly useful in plants include those conferring resistance to herbicidal compounds, such as glufosinate ammonium, bromoxynil, imidazolinones, and 2,4-dichlorophenoxyacetate (2,4-D).

In certain embodiments, the methods of the invention involve introducing a polypeptide of the invention (e.g., a cyclotide) or polynucleotide of the invention (e.g., encoding a cyclotide) into a plant. "Introducing" is intended to mean presenting to the plant the polynucleotide or polypeptide in such a manner that the sequence gains access to the interior of a cell of the plant. In certain embodiments, the polypeptides are fusion polypeptides comprising an N-terminal and/or C-terminal extension, as described above. In certain embodiments, the polynucleotides encode such fusion polypeptides. The methods of the invention do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods. Polypeptides can also be introduced to a plant in such a manner that they gain access to the interior of the plant cell or remain external to the cell but in close contact with it.

As used herein, the term "plant" also includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. No. 5,563,055 and U.S. Pat. No. 5,981,840), direct gene transfer (Paszkowski et al. (1984) *EMBO J.* 3:2717-2722), and ballistic particle acceleration (see, for example, U.S. Pat. No. 4,945,050; U.S. Pat. No. 5,879,918; U.S. Pat. No. 5,886,244; and, U.S. Pat. No. 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al.

(1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; U.S. Pat. No. 5,736, 369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the sequences of the invention can be provided to a plant using a variety of transient transformation methods. Such transient transformation methods include, but are not limited to, the introduction of the protein or variants and fragments thereof directly into the plant or the introduction of a corresponding transcript into the plant. Such methods include, for example, microinjection or particle bombardment. See, for example, Crossway et al. (1986) *Mol. Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it's released to become integrated into the genome is greatly reduced. Such methods include the use particles coated with polyethylimine (PEI; Sigma #P3143).

In other embodiments, the polynucleotide of the invention may be introduced into plants by contacting plants with a virus or viral nucleic acids. Generally, such methods involve incorporating a nucleotide construct of the invention within a viral DNA or RNA molecule. It is recognized that the pesticidal polypeptide of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889, 190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in a transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

In certain embodiments, the polynucleotides of the present invention can be stacked with any combination of polynucleotide sequences of interest in order to create plants with a desired phenotype. For example, the polynucleotides of the present invention may be stacked with other pesticidal genes and the like. The combinations generated can also include multiple copies of any one of the polynucleotides of interest. The polynucleotides of the present invention can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990, 389; 5,885,801; 5,885,802; and 5,703,409); barley high lysine (Williamson et al. (1987) *Eur. J. Biochem.* 165:99-106; and WO 98/20122) and high methionine proteins (Pedersen et al. (1986) *J. Biol. Chem.* 261:6279; Kirihara et al. (1988) *Gene* 71:359; and Musumura et al. (1989) *Plant Mol. Biol.* 12:123)); increased digestibility (e.g., modified storage proteins (U.S. Pat. No. 6,858,778); and thioredoxins (U.S. Pat. No. 7,009,087)); the disclosures of which are herein incorporated by reference.

The polynucleotides of the present invention can also be stacked with traits desirable for insect, disease, or herbicide resistance (e.g., other *Bacillus thuringiensis* toxic proteins (U.S. Pat. Nos. 5,366,892; 5,747,450; 5,737,514; 5,723,756; 5,593,881; Geiser et al. (1986) *Gene* 48:109); lectins (Van Damme et al. (1994) *Plant Mol. Biol.* 24:825); fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (e.g., the EPSPS gene and the GAT gene; see, for example U.S. Publication No. 20040082770 and WO 03/092360)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

The present invention may be used to induce pest resistance or protect from pest attack any plant species, including, but not limited to, monocots and dicots (e.g., any monocot or dicot disclosed herein).

In particular aspects, methods for inducing pest resistance in a plant comprise introducing into a plant at least one polynucleotide, wherein the polynucleotide comprises a nucleotide sequence encoding a pesticidal cyclotide polypeptide of the invention. The polynucleotide is operably linked to a promoter that drives expression in the plant. In certain embodiments, the polynucleotide comprises 5' and/or 3' extensions (e.g., encoding N-terminal and/or C-terminal extensions). The plant expresses the pesticidal cyclotide polypeptide, thereby exposing the pest to the polypeptide at the site of attack. In particular embodiments, the cyclotide polypeptides have nematicidal activity and the pest is a nematode. In other embodiments, the cyclotide polypeptides have insecticidal activity and the pest is an insect. Expression of a cyclotide polypeptide of the invention may be targeted to specific plant tissues where pest resistance is particularly important. Such tissue-preferred expression may be accomplished by, e.g., root-preferred, leaf-preferred, vascular tissue-preferred, stalk-preferred, or seed-preferred promoters. For nematode control, root-preferred promoters are typically optimal. For insect control, leaf-preferred promoters are ofter optimal.

The compositions of the invention find further use in methods directed to protecting a plant from a pest or pathogen. "Protecting a plant from a pest or pathogen" is intended to mean killing the pest or pathogen or preventing or limiting disease formation on a plant. In some embodiments, a composition comprising a polypeptide of the invention and a carrier is applied directly to the environment of a plant pest or pathogen, such as, for example, on a plant or in the soil or other growth medium surrounding the roots of the plant, in order to protect the plant from pest and/or pathogen attack. Microorganisms comprising a polynucleotide encoding a polypeptide of the invention and methods of using them to protect a plant from a pest or pathogen are further provided. In some embodiments, the transformed microorganism is applied directly to a plant or to the soil in which a plant grows.

Thus, the invention involves biodegradable pesticides and genes that encode them, thereby providing new approaches for impacting plant pests that do not depend on the use of traditional, synthetic chemicals. As used herein, the term "plant pest" refers to any organism that can cause harm to a plant by inhibiting or slowing the growth of a plant, by damaging the tissues of a plant, by weakening the immune system of a plant, reducing the resistance of a plant to abiotic stresses, and/or by causing the premature death of the plant, etc. Relevant plant pests include, e.g., nematodes, insects, and the like.

As used herein, the term "impacting pests" refers to effecting changes in pest feeding, growth, and/or behavior at any stage of development, including but not limited to: killing the pest; retarding its growth; preventing or reducing its reproductive capability; preventing or reducing its ability to feed; and the like.

As used herein, the term "pesticidal activity" refers to the activity of an organism or a substance (such as, for example, a protein) that can be measured by, e.g., pest mortality, pest weight loss, pest repellency, and other behavioral and physical changes of a pest after feeding and exposure for an appropriate length of time. Thus, an organism or substance having pesticidal activity adversely impacts at least one measurable parameter of pest fitness. "Pesticidal proteins" are proteins that display pesticidal activity by themselves or in combination with other proteins.

In particular embodiments, the pesticidal activity exhibited by the cyclotide polypeptides of the invention is nematicidal activity. As used herein, "nematicidal activity" refers to the ability to adversely impact at least one measurable parameter of nematode fitness. In certain embodiments, the nematicidal activity is measured with respect to a nematode that is a member of a *Meloidogyne, Heterodera,* or *Globedera* genera. In other embodiments, the nematicidal activity is measured with respect to a nematode that is selected from the group consisting of *Panagrellus redivivus, Pristionchus pacificus,* and *Caenorhabditis elegans.* Evidence of nematicidal activity includes, for example, lack of pumping, inhibition of growth (i.e., small size), pale coloration, lethargy, decreased reproduction, and/or death. See, e.g., Wei et al. (2003), Proc. Nat'l Acad. Sci. 100(5):2760-65.

In other embodiments, the pesticidal activity exhibited by the cyclotide polypeptides of the invention is insecticidal activity. As used herein, "insecticidal activity" refers to the ability to adversely impact insect growth or reproduction, at any stage of development, or the ability to kill the insect. Insecticidal activity can be measured by insect assays known in the art.

As used herein, the term "pesticidally effective amount" connotes a quantity of a substance or organism that has pesticidal activity when present in the environment of a pest. For each substance or organism, the pesticidally effective amount is determined empirically for each pest affected in a specific environment. A "nematicidally effective amount" may be used to refer to a "pesticidally effective amount" when the pest is a nematode. Similarly, an "insecticidally effective amount" may be used to refer to a "pesticidally effective amount" when the pest is an insect pest.

Biopesticide compositions, particularly nematicidal and insecticidal compositions, are thus encompassed by the present invention. Biopesticide compositions may comprise pesticidal cyclotide polypeptides or microorganisms comprising a heterologous polynucleotide that encodes a pesticidal cyclotide polypeptide. The biopesticide compositions of the invention may be applied to the environment of a plant pest or pathogen, as described herein below, thereby protecting a plant from pest and/or pathogen attack. Moreover, a biopesticide composition can be formulated with an acceptable carrier that is, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

The biospesticide compositions find further use in the decontamination of plant pest and/or pathogens during the processing of grain for animal or human food consumption; during the processing of feedstuffs, and during the processing of plant material for silage. In this embodiment, the biopesticide compositions of the invention are presented to grain, plant material for silage, or a contaminated food crop, or during an appropriate stage of the processing procedure, in amounts effective for nematicidal and/or insecticidal activity.

Microorganisms that are known to occupy the "phytosphere" (phylloplane, phyllosphere, rhizosphere, and/or rhizoplane) of one or more crops of interest may be selected as host cells for making microbial-based biopesticide compositions. For example, polynucleotides encoding the pesticidal cyclotide polypeptides of the invention can be introduced into microorganisms that multiply on plants (i.e., epiphytes) to deliver pesticidal cyclotide proteins to potential target pests. Epiphytes, for example, can be gram-positive or gram-negative bacteria. Such microorganisms are selected so as to be capable of successfully competing in the particular environment with the wild-type microorganisms, and to provide for stable maintenance and expression of the gene expressing the pesticidal protein.

Root-colonizing bacteria, for example, can be isolated from the plant of interest by methods known in the art. Specifically, a *Bacillus cereus* strain that colonizes roots can be isolated from roots of a plant (see, for example, Handelsman et al. (1991) *Appl. Environ. Microbiol.* 56:713-718). Polynucleotides encoding the pesticidal polypeptides of the invention can be introduced into a root-colonizing *Bacillus cereus* by standard methods known in the art. Polynucleotides encoding pesticidal cyclotide polypeptides can be introduced, for example, into the root-colonizing *Bacillus* by means of electrotransformation. Specifically, polynucleotides encoding the pesticidal cyclotide proteins can be cloned into a shuttle vector, for example, pHT3101 (Lerecius et al. (1989) *FEMS Microbiol. Letts.* 60: 211-218. The shuttle vector pHT3101 containing the coding sequence for the particular pesticidal protein can, for example, be transformed into the root-colonizing *Bacillus* by means of electroporation (Lerecius et al. (1989) *FEMS Microbiol. Letts.* 60: 211-218).

Methods are provided for protecting a plant from a pest comprising applying an effective amount of a pesticidal cyclotide polypeptide or biopesticide composition of the invention to the environment of the pest. "Effective amount" is intended to mean an amount of a protein or composition sufficient to control a pest. The pesticidal proteins and compositions can be applied to the environment of the pest by methods known to those of ordinary skill in the art.

Prior to the application of a biopesticide composition of the invention to an area of cultivation, the environment can be evaluated to determine if the pest of interest is present or if conditions are conducive to pest growth or infestation. As used herein, an "area of cultivation" comprises any region in which one desires to grow a plant. Such areas of cultivations include, but are not limited to, a field in which a plant is cultivated (such as a crop field, a sod field, a tree field, a managed forest, a field for culturing fruits and vegetables, etc), a greenhouse, a growth chamber, etc. Evaluation of the environment can aid in determining the effective amount of the pesticidal cyclotide polypeptide or biopesticde composition of the invention needed to control a pest within an area of cultivation.

Environmental conditions that can be evaluated include, but are not limited to, ground and surface water pollution concerns, intended use of the crop, crop tolerance, soil residuals, weeds present in area of cultivation, humidity, soil texture, pH of soil, amount of organic matter in soil, water content of soil, application equipment, and tillage practices. Following the evaluation of the environmental conditions, an effective amount of a pesticidal cyclotide polypeptide or biopesticide composition of the invention can be applied to the crop, crop part, seed of the crop or area of cultivation.

The biopesticide compositions of the invention may be obtained by the addition of a surface-active agent, an inert carrier, a preservative, a humectant, a feeding stimulant, an attractant, an encapsulating agent, a binder, an emulsifier, a dye, a UV protective, a buffer, a flow agent or fertilizers, micronutrient donors, or other preparations that influence plant growth. One or more agrochemicals including, but not limited to, herbicides, insecticides, fungicides, bactericides, nematicides, molluscicides, acaricides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area, plant, or seed to be treated. For example, the compositions of the present invention may be applied to grain in preparation for or during storage in a grain bin or silo, etc. The compositions of the present invention may be applied simultaneously or in succession with other compounds. Methods of applying an active ingredient of the present invention or an agrochemical composition of the present invention that contains at least one of the pesticidal proteins, more particularly nematicidal or insecticidal proteins, of the present invention include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkylbenzene sulfonates or lower alkylnaphtalene sulfonates, e.g., butyl-naphthalene sulfonate; salts of sulfonated naphthaleneformaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates, or botanical materials such as cork, powdered corncobs, peanut hulls, rice hulls, and walnut shells.

The biopesticide compositions of the present invention can be in a suitable form for direct application or as a concentrate of primary composition that requires dilution with a suitable quantity of water or other diluent before application. The concentration of the pesticidal polypeptide will vary depending upon the nature of the particular formulation, specifically, whether it is a concentrate or to be used directly. The composition contains 1 to 98% of a solid or liquid inert carrier, and 0 to 50%, optimally 0.1 to 50% of a surfactant. These compositions will be administered at the labeled rate for the commercial product, optimally about 0.01 lb-5.0 lb. per acre when in dry form and at about 0.01 pts.-10 pts. per acre when in liquid form.

The biopesticide compositions of the invention can be applied to the environment of a plant pathogen by, for example, spraying, atomizing, dusting, scattering, coating or pouring, introducing into or on the soil, introducing into irrigation water, by seed treatment or general application or dusting at the time when the pathogen has begun to appear or before the appearance of pests as a protective measure. For example, the pesticidal protein and/or transformed microorganisms of the invention may be mixed with grain to protect the grain during storage. It is generally important to obtain good control of pests in the early stages of plant growth, as this is the time when the plant can be most severely damaged. In one embodiment of the invention, the composition is applied directly to the soil, at a time of planting, in granular form of a composition of a carrier and pesticidal polypeptides or transformed microorganisms of the invention. Another embodiment is a granular form of a composition comprising an agrochemical such as, for example, a herbicide, an insecticide, a fertilizer, an inert carrier, and pesticidal polypeptides or transformed microorganisms of the invention.

One of skill in the art will appreciate that the compositions and methods disclosed herein can be used with other compositions and methods available in the art for protecting plants from pathogen attack. For example, methods of the invention can comprise the use of one or more herbicides, insecticides, fungicides, nematocides, bactericides, acaricides, growth regulators, chemosterilants, semiochemicals, repellents, attractants, pheromones, feeding stimulants or other biologically active compounds or entomopathogenic bacteria, virus, or fungi to form a multi-component mixture giving an even broader spectrum of agricultural protection. General references for these agricultural protectants include The Pesticide Manual, 13th Edition, C. D. S. Tomlin, Ed., British Crop Protection Council, Farnham, Surrey, U.K., 2003 and The BioPesticide Manual, 2nd Edition, L. G. Copping, Ed., British Crop Protection Council, Farnham, Surrey, U.K., 2001.

The embodiments of the present invention may be effective against a variety of plant pathogens. Pathogens of the invention include, but are not limited to, nematodes, insects, viruses or viroids, bacteria, fungi, and the like. Nematodes pests include plant parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Insects pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera.

Insects of the order Lepidoptera include, but are not limited to, armyworms, cutworms, loopers, and heliothines in the family Noctuidae *Agrotis ipsilon* Hufnagel (black cutworm); *A. orthogonia* Morrison (western cutworm); *A. segetum* Denis & Schiffermüller (turnip moth); *A. subterranea* Fabricius (granulate cutworm); *Alabama argillacea* Hübner (cotton leaf worm); *Anticarsia gemmatalis* Hübner (velvetbean caterpillar); *Athetis mindara* Barnes and McDunnough (rough skinned cutworm); *Earias insulana* Boisduval (spiny bollworm); *E. vittella* Fabricius (spotted bollworm); *Egira (Xylomyges) curialis* Grote (citrus cutworm); *Euxoa messoria* Harris (darksided cutworm); *Helicoverpa armigera* Hübner (American bollworm); *H. zea* Boddie (corn earworm or cotton bollworm); *Heliothis virescens* Fabricius (tobacco budworm); *Hypena scabra* Fabricius (green cloverworm); *Hyponeuma taltula* Schaus; (*Mamestra configurata* Walker (bertha armyworm); *M. brassicae* Linnaeus (cabbage moth); *Melanchra picta* Harris (zebra caterpillar); *Mocis latipes* Guenée (small mocis moth); *Pseudaletia unipuncta* Haworth (armyworm); *Pseudoplusia includens* Walker (soybean looper); *Richia albicosta* Smith (Western bean cutworm); *Spodoptera frugiperda* JE Smith (fall armyworm); *S. exigua* Hübner (beet armyworm); *S. litura* Fabricius (tobacco cutworm, cluster caterpillar); *Trichoplusia ni* Hübner (cabbage looper); borers, casebearers, webworms, coneworms, and skeletonizers from the families Pyralidae and Crambidae such as *Achroia grisella* Fabricius (lesser wax moth); *Amyelois transitella* Walker (naval orangeworm); *Anagasta kuehniella* Zeller (Mediterranean flour moth); *Cadra cautella* Walker (almond moth); *Chilo partellus* Swinhoe (spotted stalk borer); *C. suppressalis* Walker (striped stem/rice borer); *C. terrenellus* Pagenstecher (sugarcane stemp borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenée (rice leaf roller); *Desmia funeralis* Hübner (grape leaffolder); *Diaphania hyalinata* Linnaeus (melon worm); *D. nitidalis* Stoll (pickleworm); *Diatraea flavipennella* Box; *D. grandiosella* Dyar (southwestern corn borer), *D. saccharalis* Fabricius (surgarcane borer); *Elasmopalpus lignosellus* Zeller (lesser cornstalk borer); *Eoreuma loftini* Dyar (Mexican rice borer); *Ephestia elutella* Hübner (tobacco (cacao) moth);

*Galleria mellonella* Linnaeus (greater wax moth); *Hedylepta accepta* Butler (sugarcane leafroller); *Herpetogramma licarsisalis* Walker (sod webworm); *Homoeosoma electellum* Hulst (sunflower moth); *Loxostege sticticalis* Linnaeus (beet webworm); *Maruca testulalis* Geyer (bean pod borer); *Orthaga thyrisalis* Walker (tea tree web moth); *Ostrinia nubilalis* Hübner (European corn borer); *Plodia interpunctella* Hübner (Indian meal moth); *Scirpophaga incertulas* Walker (yellow stem borer); *Udea rubigalis* Guenée (celery leaftier); and leafrollers, budworms, seed worms, and fruit worms in the family Tortricidae *Acleris gloverana* Walsingham (Western blackheaded budworm); *A. variana* Fernald (Eastern blackheaded budworm); *Adoxophyes orana* Fischer von Rösslerstamm (summer fruit tortrix moth); *Archips* spp. including *A. argyrospila* Walker (fruit tree leaf roller) and *A. rosana* Linnaeus (European leaf roller); *Argyrotaenia* spp.; *Bonagota salubricola* Meyrick (Brazilian apple leafroller); *Choristoneura* spp.; *Cochylis hospes* Walsingham (banded sunflower moth); *Cydia latiferreana* Walsingham (filbertworm); *C. pomonella* Linnaeus (codling moth); *Endopiza viteana* Clemens (grape berry moth); *Eupoecilia ambiguella* Hübner (vine moth); *Grapholita molesta* Busck (oriental fruit moth); *Lobesia botrana* Denis & Schiffermüller (European grape vine moth); *Platynota flavedana* Clemens (variegated leafroller); *P. stultana* Walsingham (omnivorous leafroller); *Spilonota ocellana* Denis & Schiffermüller (eyespotted bud moth); and *Suleima helianthana* Riley (sunflower bud moth).

Selected other agronomic pests in the order Lepidoptera include, but are not limited to, *Alsophila pometaria* Harris (fall cankerworm); *Anarsia lineatella* Zeller (peach twig borer); *Anisota senatoria* J.E. Smith (orange striped oakworm); *Antheraea pernyi* Guérin-Méneville (Chinese Oak Silkmoth); *Bombyx mori* Linnaeus (Silkworm); *Bucculatrix thurberiella* Busck (cotton leaf perforator); *Colias eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Erechthias flavistriata* Walsingham (sugarcane bud moth); *Euproctis chrysorrhoea* Linnaeus (browntail moth); *Harrisina americana* Guérin-Méneville (grapeleaf skeletonizer); *Heliothis subflexa* Guenée; *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Malacosoma* spp.; *Manduca quinquemaculata* Haworth (five spotted hawk moth, tomato hornworm); *M. sexta* Haworth (tomato hornworm, tobacco hornworm); *Operophtera brumata* Linnaeus (winter moth); *Orgyia* spp.; *Paleacrita vernata* Peck (spring cankerworm); *Papilio cresphontes* Cramer (giant swallowtail, orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval & Leconte (Southern cabbageworm); *Sabulodes aegrotata* Guenée (omnivorous looper); *Schizura concinna* J.E. Smith (red humped caterpillar); *Sitotroga cerealella* Olivier (Angoumois grain moth); *Telchin licus* Drury (giant sugarcane borer); *Thaumetopoea pityocampa* Schiffermüller (pine processionary caterpillar); *Tineola bisselliella* Hummel (webbing clothesmoth); *Tuta absoluta* Meyrick (tomato leafminer) and *Yponomeuta padella* Linnaeus (ermine moth).

Included as insects of interest are those of the order Hemiptera such as, but not limited to, the following families: Adelgidae, Aleyrodidae, Aphididae, Asterolecamidae, Cercopidae, Cicadellidae, Cicadidae, Cixiidae, Coccidae, Coreidae, Dactylopiidae, Delphacidae, Diaspididae, Eriococcidae, Flatidae, Fulgoridae, Issidae, Lygaeidae, Margarodidae, Membracidae, Miridae, Ortheziidae, Pentatomidae, Phoenicococcidae, Phylloxeridae, Pseudococcidae, Psyllidae, Pyrrhocoridae and Tingidae.

Agronomically important members from the order Hemiptera include, but are not limited to: *Acrosternum hilare* Say (green stink bug); *Acyrthisiphon pisum* Harris (pea aphid); *Adelges* spp. (adelgids); *Adelphocoris rapidus* Say (rapid plant bug); *Anasa tristis* De Geer (squash bug); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacaspis tegalensis* Zehntner (sugarcane scale); *Aulacorthum solani* Kaltenbach (foxglove aphid); *Bemisia tabaci* Gennadius (tobacco whitefly, sweetpotato whitefly); *B. argentifolii* Bellows & Perring (silverleaf whitefly); *Blissus leucopterus leucopterus* Say (chinch bug); *Blostomatidae* spp.; *Brevicoryne brassicae* Linnaeus (cabbage aphid); *Cacopsylla pyricola* Foerster (pear psylla); *Calocoris norvegicus* Gmelin (potato capsid bug); *Chaetosiphon fragaefolii* Cockerell (strawberry aphid); *Cimicidae* spp.; *Coreidae* spp.; *Corythuca gossypii* Fabricius (cotton lace bug); *Cyrtopeltis modesta* Distant (tomato bug); *C. notatus* Distant (suckfly); *Deois flavopicta* Stål (spittlebug); *Dialeurodes citri* Ashmead (citrus whitefly); *Diaphnocoris chlorionis* Say (honeylocust plant bug); *Diuraphis noxia* Kurdjumov/Mordvilko (Russian wheat aphid); *Duplachionaspis divergens* Green (armored scale); *Dysaphis plantaginea* Paaserini (rosy apple aphid); *Dysdercus suturellus* Herrich-Schäffer (cotton stainer); *Dysmicoccus boninsis* Kuwana (gray sugarcane mealybug); *Empoasca fabae* Harris (potato leafhopper); *Eriosoma lanigerum* Hausmann (woolly apple aphid); *Erythroneoura* spp. (grape leafhoppers); *Eumetopina flavipes* Muir (Island sugarcane planthopper); *Eurygaster* spp.; *Euschistus servus* Say (brown stink bug); *E. variolarius* Palisot de Beauvois (one-spotted stink bug); *Graptostethus* spp. (complex of seed bugs); and *Hyalopterus pruni* Geoffroy (mealy plum aphid); *Icerya purchasi* Maskell (cottony cushion scale); *Labopidicola allii* Knight (onion plant bug); *Laodelphax striatellus* Fallen (smaller brown planthopper); *Leptoglossus corculus* Say (leaf-footed pine seed bug); *Leptodictya tabida* Herrich-Schaeffer (sugarcane lace bug); *Lipaphis erysimi* Kaltenbach (turnip aphid); *Lygocoris pabulinus* Linnaeus (common green capsid); *Lygus lineolaris* Palisot de Beauvois (tarnished plant bug); *L. Hesperus* Knight (Western tarnished plant bug); *L. pratensis* Linnaeus (common meadow bug); *L. rugulipennis* Poppius (European tarnished plant bug); *Macrosiphum euphorbiae* Thomas (potato aphid); *Macrosteles quadrilineatus* Forbes (aster leafhopper); *Magicicada septendecim* Linnaeus (periodical cicada); *Mahanarva fimbriolata* Stål (sugarcane spittlebug); *M. posticata* Stål (little cicada of sugarcane); *Melanaphis sacchari* Zehntner (sugarcane aphid); *Melanaspis glomerate* Green (black scale); *Metopolophium dirhodum* Walker (rose grain aphid); *Myzus persicae* Sulzer (peach-potato aphid, green peach aphid); *Nasonovia ribisnigri* Mosley (lettuce aphid); *Nephotettix cinticeps* Uhler (green leafhopper); *N. nigropictus* Stål (rice leafhopper); *Nezara viridula* Linnaeus (southern green stink bug); *Nilaparvata lugens* Stål (brown planthopper); *Nysius ericae* Schilling (false chinch bug); *Nysius raphanus* Howard (false chinch bug); *Oebalus pugnax* Fabricius (rice stink bug); *Oncopeltus fasciatus* Dallas (large milkweed bug); *Orthops campestris* Linnaeus; *Pemphigus* spp. (root aphids and gall aphids); *Peregrinus maidis* Ashmead (corn planthopper); *Perkinsiella saccharicida* Kirkaldy (sugarcane delphacid); *Phylloxera devastatrix* Pergande (pecan phylloxera); *Planococcus citri* Risso (citrus mealybug); *Plesiocoris rugicollis* Fallen (apple capsid); *Poecilocapsus lineatus* Fabricius (four-lined plant bug); *Pseudatomoscelis seriatus* Reuter (cotton fleahopper); *Pseudococcus* spp. (other mealybug complex); *Pulvinaria elongata* Newstead (cottony grass scale); *Pyrilla perpusilla* Walker (sugarcane leafhopper); Pyrrhocoridae spp.; *Quadraspidiotus perniciosus* Comstock (San Jose scale); Reduviidae spp.; *Rhopalosiphum maidis* Fitch (corn leaf aphid); *R. padi* Linnaeus (bird cherry-oat aphid); *Saccharicoccus sacchari* Cockerell (pink sugarcane mealybug); *Scaptacoris castanea* Perty (brown root stink bug); *Schizaphis graminum* Rondani (greenbug); *Sipha flava* Forbes (yellow sugarcane aphid); *Sitobion avenae* Fabricius (English grain aphid); *Sogatella furcifera* Horvath (white-backed planthopper); *Sogatodes oryzicola* Muir (rice delphacid); *Spanagonicus albofasciatus* Reuter (whitemarked fleahopper); *Therioaphis maculata* Buckton (spotted alfalfa aphid); *Tinidae* spp.; *Toxoptera aurantii* Boyer de Fonscolombe (black citrus aphid); and *T. citricida* Kirkaldy (brown citrus aphid); *Trialeurodes abutiloneus* (bandedwinged whitefly) and *T. vaporariorum* Westwood (greenhouse whitefly); *Trioza diospyri* Ashmead (persimmon psylla); and *Typhlocyba pomaria* McAtee (white apple leafhopper).

Of interest are larvae and adults of the order Coleoptera including weevils from the families Anthribidae, Bruchidae, and Curculionidae including, but not limited to: *Anthonomus grandis* Boheman (boll weevil); *Cylindrocopturus adspersus* LeConte (sunflower stem weevil); *Diaprepes abbreviatus* Linnaeus (Diaprepes root weevil); *Hypera punctata* Fabricius (clover leaf weevil); *Lissorhoptrus oryzophilus* Kuschel (rice water weevil); *Metamasius hemipterus hemipterus* Linnaeus (West Indian cane weevil); *M. hemipterus sericeus* Olivier (silky cane weevil); *Sitophilus granarius* Linnaeus (granary weevil); *S. oryzae* Linnaeus (rice weevil); *Smicronyx fulvus* LeConte (red sunflower seed weevil); *S. sordidus* LeConte (gray sunflower seed weevil); *Sphenophorus maidis* Chittenden (maize billbug); *S. livis* Vaurie (sugarcane weevil); *Rhabdoscelus obscurus* Boisduval (New Guinea sugarcane weevil); flea beetles, cucumber beetles, rootworms, leaf beetles, potato beetles, and leafminers in the family Chrysomelidae including, but not limited to: *Chaetocnema ectypa* Horn (desert corn flea beetle); *C. pulicaria* Melsheimer (corn flea beetle); *Colaspis brunnea* Fabricius (grape *colaspis*); *Diabrotica barberi* Smith & Lawrence (northern corn rootworm); *D. undecimpunctata howardi* Barber (southern corn rootworm); *D. virgifera virgifera* LeConte (western corn rootworm); *Leptinotarsa decemlineata* Say (Colorado potato beetle); *Oulema melanopus* Linnaeus (cereal leaf beetle); *Phyllotreta cruciferae* Goeze (corn flea beetle); *Zygogramma exclamationis* Fabricius (sunflower beetle); beetles from the family Coccinellidae including, but not limited to: *Epilachna varivestis* Mulsant (Mexican bean beetle); chafers and other beetles from the family Scarabaeidae including, but not limited to: *Antitrogus parvulus* Britton (Childers cane grub); *Cyclocephala borealis* Arrow (northern masked chafer, white grub); *C. immaculata* Olivier (southern masked chafer, white grub); *Dermolepida albohirtum* Waterhouse (Greyback cane beetle); *Euetheola humilis rugiceps* LeConte (sugarcane beetle); *Lepidiota frenchi* Blackburn (French's cane grub); *Tomarus gibbosus* De Geer (carrot beetle); *T. subtropicus* Blatchley (sugarcane grub); *Phyllophaga crinita* Burmeister (white grub); *P. latifrons* LeConte (June beetle); *Popillia japonica* Newman (Japanese beetle); *Rhizotrogus majalis* Razoumowsky (European chafer); carpet beetles from the family Dermestidae; wireworms from the family Elateridae, *Eleodes* spp., *Melanotus* spp. including *M. communis* Gyllenhal (wireworm); *Conoderus* spp.; *Limonius* spp.; *Agriotes* spp.; *Ctenicera* spp.; *Aeolus* spp.; bark beetles from the family Scolytidae; beetles from the family Tenebrionidae; beetles from the family Cerambycidae such as, but not limited to, *Migdolus fryanus* Westwood (longhorn beetle); and beetles from the Buprestidae family including, but not limited to, *Aphanisticus cochinchinae seminulum* Obenberger (leaf-mining buprestid beetle).

Adults and immatures of the order Diptera are of interest, including leafminers *Agromyza parvicornis* Loew (corn blotch leafminer); midges including, but not limited to: *Contarinia sorghicola* Coquillett (sorghum midge); *Mayetiola destructor* Say (Hessian fly); *Neolasioptera murtfeldtiana* Felt, (sunflower seed midge); *Sitodiplosis mosellana* Géhin (wheat midge); fruit flies (Tephritidae), *Oscinella frit* Linnaeus (frit flies); maggots including, but not limited to: *Delia* spp. including *Delia platura* Meigen (seedcorn maggot); *D. coarctata* Fallen (wheat bulb fly); *Fannia canicularis* Linnaeus, *F. femoralis* Stein (lesser house flies); *Meromyza americana* Fitch (wheat stem maggot); *Musca domestica* Linnaeus (house flies); *Stomoxys calcitrans* Linnaeus (stable flies)); face flies, horn flies, blow flies, *Chrysomya* spp.; *Phormia* spp.; and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds); and other *Brachycera*, mosquitoes *Aedes* spp.; *Anopheles* spp.; *Culex* spp.; black flies *Prosimulium* spp.; *Simulium* spp.; biting midges, sand flies, sciarids, and other *Nematocera*.

Also included are adults and larvae of the order Acari (mites) such as *Aceria tosichella* Keifer (wheat curl mite); *Panonychus ulmi* Koch (European red mite); *Petrobia latens* Müller (brown wheat mite); *Steneotarsonemus bancrofti* Michael (sugarcane stalk mite); spider mites and red mites in the family Tetranychidae, *Oligonychus grypus* Baker & Pritchard, *O. indicus* Hirst (sugarcane leaf mite), *O. pratensis* Banks (Banks grass mite), *O. stickneyi* McGregor (sugarcane spider mite); *Tetranychus urticae* Koch (two spotted spider mite); *T. mcdanieli* McGregor (McDaniel mite); *T. cinnabarinus* Boisduval (carmine spider mite); *T. turkestani* Ugarov & Nikolski (strawberry spider mite), flat mites in the family Tenuipalpidae, *Brevipalpus lewisi* McGregor (citrus flat mite); rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick); and scab and itch mites in the families Psoroptidae, Pyemotidae, and Sarcoptidae.

Insect pests of the order Thysanura are of interest, such as *Lepisma saccharina* Linnaeus (silverfish); *Thermobia domestica* Packard (firebrat).

In an embodiment of the invention, the compositions of the invention may be used as a pharmaceutical composition for treatment of parasites (e.g., namatode parasites) in humans and other animals. Examples of nematode parasites include, but are not limited to, ascarids (*Ascaris*), filarias (e.g.,

*Onchocerca volvulus*), hookworms, pinworms (*Enterobius*), whipworms (e.g., *Trichuris trichiura*), *Trichinella spiralis, Baylisascaris, Dirofilaria immitis, Haemonchus contortus, Nippostrongylus brasiliensis, Ancylostoma duodenale,* and *Necator americanus.* In some of these embodiments, the pesticidal polypeptide is combined with a pharmaceutically acceptable carrier. As used herein the term "pharmaceutically acceptable carrier" includes solvents, dispersion media, coatings, antibacterial and antifungal agents, isotonic and absorption delaying agents, and the like, compatible with pharmaceutical administration. Supplementary active compounds also can be incorporated into the compositions.

The presently disclosed pharmaceutical compositions may be administered to a patient through numerous means. Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 µg/kg to about 15 mg/kg (e.g., 0.1 to 20 mg/kg) of active compound is an initial candidate dosage for administration to the patient, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

"Treatment" is herein defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A "therapeutic agent" comprises, but is not limited to, the polypeptides and pharmaceutical compositions of the invention.

The cyclotide polypeptides of the invention can be used for any application including coating surfaces to target parasites. In this manner, target parasites include parasitic nematodes that infect humans and animals (e.g., domestic livestock). Surfaces that might be coated with the pesticidal compositions of the invention include carpets and sterile medical facilities. Polymer bound polypeptides of the invention may be used to coat surfaces. Methods for incorporating compositions with antimicrobial properties into polymers are known in the art. See U.S. Pat. No. 5,847,047 herein incorporated by reference.

The articles "a" and "an" are used herein to refer to one or more than one (i.e., to at least one) of the grammatical object of the article. By way of example, "a polypeptide" is understood to represent one or more polypeptides. As such, the terms "a" (or "an"), "one or more," and "at least one" can be used interchangeably herein.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Unless defined otherwise, all technical and scientific terms used herein have the same meaning as commonly understood by one of skill in the art to which the invention pertains. Although any methods and materials similar herein can be used in the practice or testing of the present invention, the preferred methods and materials are described herein.

The following examples are offered by way of illustration and not by way of limitation.

EXPERIMENTAL

Example 1

Total Protein Extraction from *Clitoria ternatea* Seeds

*Clitoria ternatea* seeds were rinsed with 70% ethanol for 10 min, then rinsed three times with distilled water. Afterwards, the seeds were soaked in distilled water overnight, then ground up in distilled water using a mortar and pestal. The ground mixture was transferred into a centrifuge tube and centrifuge at 100,000 rpm for 10 minutes. The resulting supernatant was transferred into a new centrifuge tube and centrifuged two more times to remove any insoluble material.

The final supernatant was transferred into a new tube and designated as the crude total seed protein extract.

Example 2

Nematicidal Plate Assay

The assays for nematicidal activity are carried out in 96-well microtiter plates. Each assay well contains 120 µL of liquid with ~50 L1 staged *C. elegans*, 30 µg/mL tetracycline, 30 µg/mL chloramphenicol, a test sample (e.g., protein sample or an overnight culture), and S-medium (Marroquin et al., 2000; Wei et al., 2003). L1 larvae of *C. elegans* are synchronized by bleaching adult worms and hatching eggs overnight (Sulston & Hodgkin, 1988). *E. coli* strain OP50 is used as a control. Forty eight hours after setting up the assay wells, the plates are scored under a microscope by checking the worm's growth and development.

Crude total seed protein extract from *Clitoria ternatea* was tested for nematicidal activity using the foregoing assay conditions and was found to inhibit worm development. *C. elegans* larvae treated with as little as 0.5 µl crude total seed protein extract (depending upon the batch, protein concentration for the crude extract ranged from 2-5 mg/ml) were all arrested at the L1 stage, indicating that the seed protein extract has nematicidal activity. See FIG. 1.

Example 3

Isolation of Novel Cyclotides from *Clitoria ternatea*

Figure 2A:
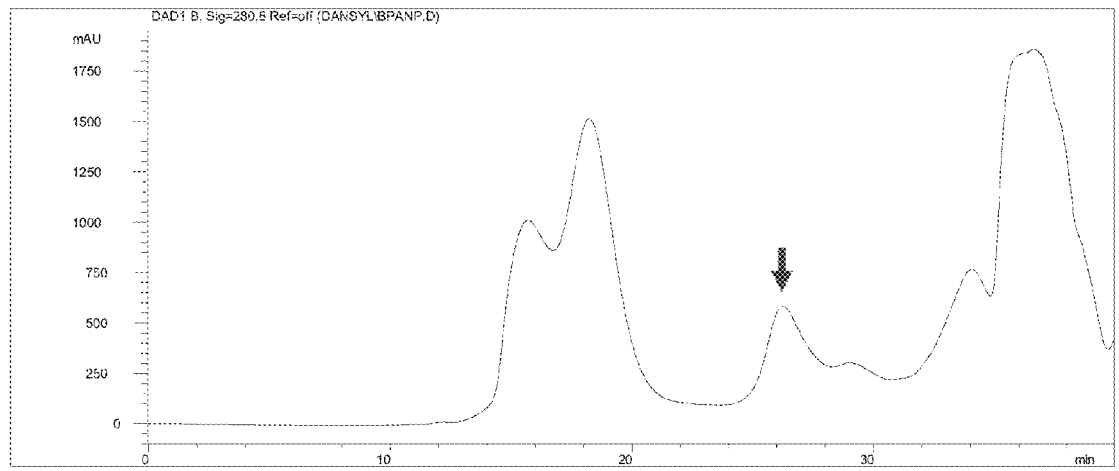
FIG. 2A depicts the elution profile of the *Clitoria ternatea* crude total seed protein extract separated on a Superdex-Peptide gel-filtration column. The arrow shows the peak having nematicidal activity.
Figure 2B:
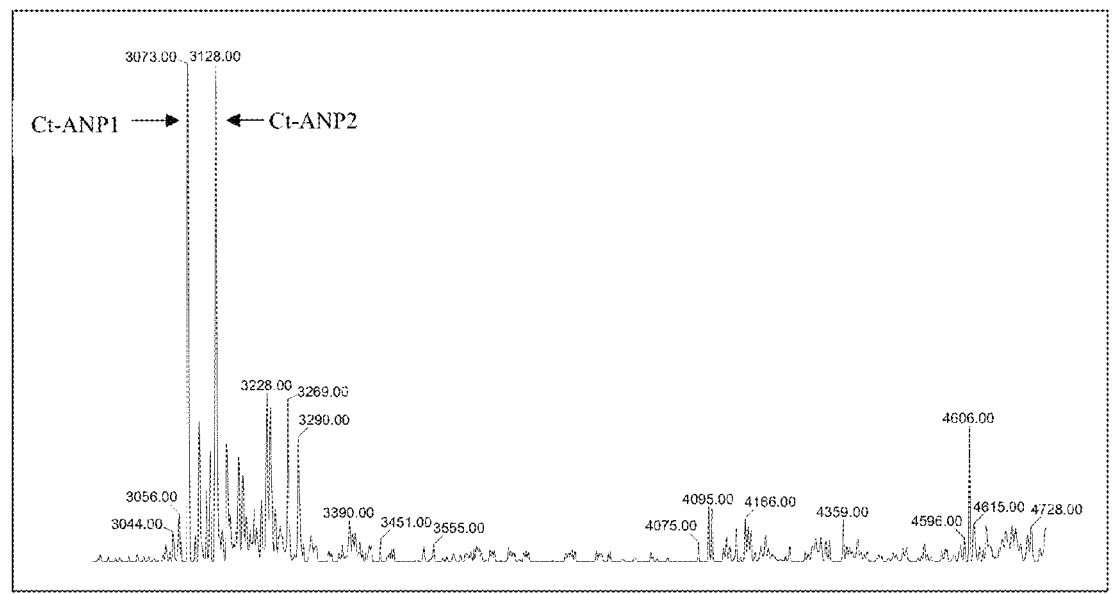
FIG. 2B depicts the mass spectrometry profile obtained from nematicidal fractions of the *Clitoria ternatea* crude total seed protein extract, following separation by Superdex-Peptide gel-filtration column and then reverse phase liquid chromatography.

To identify the active agent in the *Clitoria ternatea* crude total seed protein extract, 600 microliters of extract was fractionated on a Superdex-Peptide (GE Healthcare) gel-filtration chromatography column run at 0.5 ml/min. 0.2 ml fractions were collected and tested for nematicidal activity using the assay described in Example 2. The peak of activity occurred at fraction 67 (see FIG. 2A), which correlates with the active agent having a mass of 3000 Da.

Fractions from the Superdex-Peptide column exhibiting nematicidal activity were pooled and prepared for further purification by reverse phase liquid chromatography. To 200 microliters of pooled fractions, 50 microliters of acetonitrile and 25 microliters of 0.8% trifluoroacetic acid were added. 100 microliters of the resulting solution were injected into a Luna C8, 3 micron, 2×150 mm (Phenomenex) stationary phase column. The mobile phase at the time of application consisted of 66% solvent A (water), 20% solvent B (acetonitrile), and 14% solvent C (0.2% trifluoroacetic acid) and had a flow rate of 0.18 ml/min. During the 40 minute run, the composition of the mobile phase was a linear gradient to 48% solvent A, 40% solvent B and 12% solvent C. 0.4 minute fractions (72 ul) were collected. The fractions were then air dried, reconstituted in water, and assayed as described in Example 2. Nematicidal activity eluted in two peaks, at 30 and 33 min (designated CtANP1 and CtANP2, respectively).

Pooled protein from five identical runs was air dried and sent out for amino acid sequencing by the Edman degradation method (see below). Active fractions eluted by reverse phase chromatography were analyzed by mass spectrometry. Molecular masses of 3073 and 3128 Da for CtANP1 and CtANP2, respectively, were determined (see FIG. 3).

The two peaks identified by reverse phase chromatography were collected separately and further purified on a C-18 RP-HPLC column. The final fractions were lyophilized and reconstituted with approximately 100 ul of 20 mM Tris pH 8. The protein concentrations were determined with Nanodrop and comparison with known preotin on DSD-PAGE. The activity of the purified proteins was tested using the assay of Example 2. At concentrations of 16 ppm, both proteins strongly inhibited the development of *C. elegans* (see Table 3).

TABLE 3

Nematicidal activity of Ct-ANP1 and Ct-ANP2

|  | Ct-ANP1 | Ct-ANP2 | 0.4 ug/ul | ppm |
|---|---|---|---|---|
| 1 ul | no | no | 0.4 ug | 4 ppm |
| 2 ul | no | no | 0.8 ug | 8 ppm |
| 4 ul | yes | yes | 1.6 ug | 16 ppm |
| 6 ul | yes | yes | 2.4 ug | 24 ppm |
| 8 ul | yes | yes | 3.2 ug | 32 ppm |

Example 4

Protein Linearization and Sequencing

Initial attempt with Edman sequencing failed, indicating that the active proteins were potentially circular. The protein samples were then reduced, alkylated and digested as follows. 100 ug of CtANP protein in 100 ul 20 mM Tris pH8 was mixed with 0.6 mg DTT and incubated at 55° C. for 1 hour. Next, 5 mg of IAA was added to the reaction and the resulting mixture was allowed to incubate at room temperature for 1 hour. The pH was subsequently adjusted to pH 8 using ABC buffer. 5 ul Gluc was next added and the mixture was incubated at room temperature overnight, after which 40 ul 10% formic acid was added. After each step, a small amount of sample was taken and the molecular mass of the sample was checked with by mass spectrometry. Based on the mass calculation, it was confirmed that both Ct-ANPs are circular proteins having six cysteine residues. The treated samples were the successfully sequenced using the Edman method and the amino acid sequences of both Ct-ANPs were determined as showed in Table 4.

TABLE 4

Mass, Sequence, and Molecular Weight of Ct-ANP1 and Ct-ANP2

|  | Mass | Amino acid sequence | MW (linear) | MW (circular) |
|---|---|---|---|---|
| Ct-ANP1 | 3073 | SCVFIPCISSVVGCSCKSKVCYNNGIPCGE (amino acids 7-30, amino acids 1-6 of SEQ ID NO: 1) | 3097.65 | 3073.65 |

TABLE 4-continued

Mass, Sequence, and Molecular Weight of Ct-ANP1 and Ct-ANP2

| | Mass | Amino acid sequence | MW (linear) | MW (circular) |
|---|---|---|---|---|
| Ct-ANP2 | 3128 | SCVFIPCLTTVVGCSCKNKVCYNNGIPCGE (amino acids 7-30, amino acids 1-6 of SEQ ID NO: 2) | 3152.73 | 3128.73 |

Blast searches indicated that Ct-ANP1 and CT-ANP2 show homology to viola cyclotides. Cyclotides are a group of small peptides which form circular molecules. Cyclotides have been isolated from various members of the Rubiaceae, Violaceae, and Cucurbitaceae (see, e.g., Craik et al. 2004. Curr Protein Pept Sci 5:297"C315). All reported cyclotides are from leaves, stems and roots. In contrast, the presently disclosed cyclotides are from the Fabaceae family and were isolated from seeds.

Example 5

Cyclotide Variants

A. mRNA Isolation

To isolate the coding sequences of Ct-ANP1 and Ct-ANP2, genomic DNA was extracted from *Clitoria ternatea* leaves, stems and buds and degenerate primers were designed based on the amino acid sequences. Degenerate PCR and RACE (rapid amplifying cDNA ends) were run and the products were sequenced and analyzed. None of the products showed the coding sequence of the two Ct-ANPs. Next, total RNA was extracted from flower buds and enriched, and then a cDNA library was constructed. 2000 cloned have been sequenced and analyzed. 96 clones, when translated into protein sequences, show high homology to Ct-ANP1 and Ct-ANP2 (see Tables 1 and 2). This indicates that *Clitoria ternatea* contain a family of cyclotides. Each of the cloned sequences encodes an ORF having a cyclotide sequence flanked by N-terminal and C-terminal extensions.

B. Polynucleotide Variants

The nucleotide sequences identified in Table 2 are used to generate variant nucleotide sequences having the nucleotide sequence of the open reading frame with about 70%, 76%, 81%, 86%, 92%, and 97% nucleotide sequence identity when compared to the starting unaltered ORF nucleotide sequence. These functional variants are generated using a standard codon table. While the nucleotide sequence of the variant is altered, the amino acid sequence encoded by the open reading frame does not change.

C. Variant Amino Acid Sequences

Variant amino acid sequences of SEQ ID NO: 1 or SEQ ID NO: 2 are generated. In this example, one amino acid is altered. The selection of the amino acid to change is made by consulting a multi-sequence alignment (see below). An amino acid is selected that is deemed to be under relatively less selection pressure and which is rather easily substituted by an amino acid with similar chemical characteristics (i.e., similar functional side-chain). Once a targeted amino acid is identified, an appropriate change is made.

A multi-sequence alignment between CtANP1 (SEQ ID NO: 1) and its closest homologs based on protein Blast analysis is as follows:

```
                         (CtANP1; SEQ ID NO: 1)
GIPCGESCVFIPCISSVVGCSCKSKVCYNN (Mra 18; SEQ ID NO: 196)
_IPCGESCVFIPCISSIVGCSCKSKVCYKN (Mra 14a; SEQ ID NO: 197)
_IPCGESCVFIPCISSVVGCSCKNKVCYKN (V.bao2e; SEQ ID NO: 198)
_IPCGESCVFIPCISSVIGCSCKSKVCYRN (H.floI; SEQ ID NO: 199)
GIPCGESCVFIPCISGVIGCSCKSKVCYRN (Mra 30a; SEQ ID NO: 200)
_IPCGEGCVFIPCISSIVGCSCKSKVCYKN (Circ.C; SEQ ID NO: 201)
GIPCGESCVFIPCITSVAGCSCKSKVCYRN (V.bao2c; SEQ ID NO: 202)
GIPCGESCVLIPCISSVIGCSCKSKVCYRN (G.blaG; SEQ ID NO: 203)
_IPCGESCVFIPCISSVLGCSCKNKVCYRN (G.blaB; SEQ ID NO: 204)
_IPCGESCVFIPCISAVLGCSCKSKVCYRN (Mra 23; SEQ ID NO: 205)
_IPCGESCVFIPCISSVLGCSCKNKVCYRN (Cyc-08; SEQ ID NO: 206)
__PCGESCVWIPCISSVVGCSCKSKVCYKN (Mra 4; SEQ ID NO:207)
_IPCGESCVYIPCISSLLGCSCKSKVCYKN
```

Amino acids in the homologous sequences that differ from the corresponding amino acid in CtANP1 are underlined. Possible single amino acid variants of CtANP1 suggested by this multi-sequence alignment include: S→G at position 7; F→L at position 10; F→Y at position 10; F→W at position 10; S→T at position 15; S→A at position 16; S→G at position 16; V→I at position 17; V→L at position 17; V→I at position 18; V→L at position 18; V→A at position 18; and S→N at position 24.

A multi-sequence alignment between CtANP2 (SEQ ID NO: 2) and its closest homologs based on protein Blast analysis is as follows:

```
                         (CtANP2; SEQ ID NO: 2)
GIPCGESCVFIPCLTTVVGCSCKNKVCYNN (Cyc-C; SEQ ID NO: 208)
GIPCGESCVFIPCLTTVAGCSCKNKVCYRN (Mra14a; SEQ ID NO: 197)
_IPCGESCVFIPCISSVVGCSCKNKVCYKN
```

-continued

```
                           (Mra14b; SEQ ID NO: 209)
_IPCGESCVFIPCLTSAIGCSCKSKVCYKN (Oak8; SEQ ID NO: 210)
GVPCGESCVFIPCLTAVVGCSCSNKVCYLN (Mra29b; SEQ ID NO: 211)
GIPCGESCVFIPCLTSAIGCSCKSKVCYRN (Mra29a; SEQ ID NO: 212)
_IPCGESCVFIPCISSIVGCSCKSKVCYKN (Mra30b; SEQ ID NO: 213)
_IPCGESCVFIPCISSIVGCSCKSKVCYKN (Cyc-O10; SEQ ID NO: 214)
GIPCGESCVYIPCLTSAVGCSCKSKVCYRN (Circ-C; SEQ ID NO: 201)
GIPCGESCVFIPCITSVAGCSCKSKVCYRN
```

Amino acids in the homologous sequences that differ from the corresponding amino acid in CtANP2 are underlined. Possible single amino acid variants of CtANP2 suggested by this multi-sequence alignment include: I→V at position 2; F→Y at position 10; L→I at position 14; T→S at position 15; T→S at position 16; T→A at position 16; V→A at position 17; V→I at position 17; V→I at position 18; V→A at position 18; and N→S at position 24.

Multiple amino acid changes in a single variant can also be envisioned. Thus, for example, based on the multi-sequence alignments shown above a degenerate sequence describing a family of single and multiple change variants can be described by the sequence:

```
                                        (SEQ ID NO: 3)
G-X1-P-C-X2-E-S-C-V-X3-I-P-C-X4-X5-X6-X7-X8-G-C-S-C-X9-X10-K-V-C-Y-
N-N,
``` where
- $X_1$=I or V
- $X_2$=G or S
- $X_3$=F, Y, W or L
- $X_4$=I or L
- $X_5$=S or T
- $X_6$=S, T, A or G
- $X_7$=V, I, L or A
- $X_8$=V, I, L or A
- $X_9$=K or S
- $X_{10}$=S or N.

D. Additional Amino Acid Sequence Variants

In this example, artificial protein sequences are created having 82%, 87%, 92%, and 97% identity relative to the reference protein sequence (SEQ ID NO: 1 or SEQ ID NO: 2). This latter effort requires identifying conserved and variable regions and then the judicious application of an amino acid substitutions table. These parts will be discussed in more detail below.

The determination of which amino acid sequences are altered is made largely based on the conserved cyclotide domains and the extent to which amino acid residues in those domains tend to be conserved between cyclotide. Based on sequence alignments, the various regions of SEQ ID NO: 1 or SEQ ID NO: 2 that can likely be altered are identified. Typically, conservative substitutions can be made without altering function. In addition, one of skill will understand that functional variants of the polypeptides of the invention can also have some non-conserved amino acid alterations.

Artificial protein sequences are then created that are different from the original in the intervals of 80-85%, 85-90%, 90-95%, and 95-100% identity. Midpoints of these intervals are targeted, with liberal latitude of plus or minus 1%, for example. The amino acids substitutions will be effected by a custom Perl script. The substitution table is provided below in Table 5.

TABLE 5

Substitution Table

| Amino Acid | Strongly Similar and Optimal Substitution | Rank of Order to Change | Comment |
|---|---|---|---|
| I | L, V | 1 | 50:50 substitution |
| L | I, V | 2 | 50:50 substitution |
| V | I, L | 3 | 50:50 substitution |
| A | G | 4 | |
| G | A | 5 | |
| D | E | 6 | |
| E | D | 7 | |
| W | Y | 8 | |
| Y | W | 9 | |
| S | T | 10 | |
| T | S | 11 | |
| K | R | 12 | |
| R | K | 13 | |
| N | Q | 14 | |
| Q | N | 15 | |
| F | Y | 16 | |
| M | L | 17 | First methionine cannot change |
| H | | Na | No good substitutes |

TABLE 5-continued

Substitution Table

| Amino Acid | Strongly Similar and Optimal Substitution | Rank of Order to Change | Comment |
|---|---|---|---|
| C | | Na | No good substitutes |
| P | | Na | No good substitutes |

First, any conserved amino acids in the protein that should not be changed is identified and "marked off" for insulation from the substitution. Next, the changes are made.

H, C, and P are not changed in any circumstance. The changes will occur with isoleucine first, sweeping N-terminal to C-terminal. Then leucine, and so on down the list until the desired target it reached. Interim number substitutions can be made so as not to cause reversal of changes. The list is ordered 1-17, so start with as many isoleucine changes as needed before leucine, and so on down to methionine. Clearly many amino acids will in this manner not need to be changed. L, I and V will involved a 50:50 substitution of the two alternate optimal substitutions.

The variant amino acid sequences are written as output. Perl script is used to calculate the percent identities. Using this procedure, variants are generating having about 82%, 87%, 92%, and 97% amino acid identity to the starting unaltered ORF nucleotide sequence of SEQ ID NO: 1 or SEQ ID NO: 2.

Example 6

Transformation and Regeneration of Transgenic Maize Plants

Immature maize embryos from greenhouse donor plants are bombarded with a plasmid containing a nucleotide sequence encoding a cyclotide polypeptide of the invention (SEQ ID NO: 1) operably linked to a promoter that drives expression in a maize plant cell and a selectable marker (e.g., the selectable marker gene PAT (Wohlleben et al. (1988) *Gene* 70:25-37), which confers resistance to the herbicide Bialaphos). Alternatively, the selectable marker gene is provided on a separate plasmid.

Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising a nucleotide sequence encoding a cyclotide polypeptide of the invention operably linked to a promoter that drives expression in a maize cell is made. This plasmid DNA, plus plasmid DNA containing a selectable marker (e.g., PAT), is precipitated onto 1.1 μm (average diameter) tungsten pellets using a $CaCl_2$ precipitation procedure as follows:

100 μL prepared tungsten particles in water
10 μL (1 μg) DNA in Tris EDTA buffer (1 μg total DNA)
100 μL 2.5 M $CaCl_2$
10 μL 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 mL 100% ethanol, and centrifuged for 30 seconds. Again the liquid is removed, and 105 μL 100% ethanol is added to the final tungsten particle pellet. For particle gun bombardment, the tungsten/DNA particles are briefly sonicated and 10 μL spotted onto the center of each macrocarrier and allowed to dry about 2 minutes before bombardment.

Particle Gun Treatment

The sample plates are bombarded at level #4 in a particle gun. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/L Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for nematode and/or insect resistance.

Bombardment and Culture Media

Bombardment medium (560Y) comprises 4.0 g/L N6 basal salts (SIGMA C-1416), 1.0 mL/L Eriksson's Vitamin Mix (1000× SIGMA-1511), 0.5 mg/L thiamine HCl, 120.0 g/L sucrose, 1.0 mg/L 2,4-D, and 2.88 g/L L-proline (brought to volume with D-I $H_2O$ following adjustment to pH 5.8 with KOH); 2.0 g/L Gelrite (added after bringing to volume with D-I $H_2O$); and 8.5 mg/L silver nitrate (added after sterilizing the medium and cooling to room temperature). Selection medium (560R) comprises 4.0 g/L N6 basal salts (SIGMA C-1416), 1.0 mL/L Eriksson's Vitamin Mix (1000× SIGMA-1511), 0.5 mg/L thiamine HCl, 30.0 g/L sucrose, and 2.0 mg/L 2,4-D (brought to volume with D-I $H_2O$ following adjustment to pH 5.8 with KOH); 3.0 g/L Gelrite (added after bringing to volume with D-I $H_2O$); and 0.85 mg/L silver nitrate and 3.0 mg/L bialaphos (both added after sterilizing the medium and cooling to room temperature).

Plant regeneration medium (288J) comprises 4.3 g/L MS salts (GIBCO 11117-074), 5.0 mL/L MS vitamins stock solution (0.100 g nicotinic acid, 0.02 g/L thiamine HCL, 0.10 g/L pyridoxine HCL, and 0.40 g/L glycine brought to volume with polished D-I $H_2O$) (Murashige and Skoog (1962) *Physiol. Plant.* 15:473), 100 mg/L myo-inositol, 0.5 mg/L zeatin, 60 g/L sucrose, and 1.0 mL/L of 0.1 mM abscisic acid (brought to volume with polished D-I $H_2O$ after adjusting to pH 5.6); 3.0 g/L Gelrite (added after bringing to volume with D-I $H_2O$); and 1.0 mg/L indoleacetic acid and 3.0 mg/L bialaphos (added after sterilizing the medium and cooling to 60° C.). Hormone-free medium (272V) comprises 4.3 g/L MS salts (GIBCO 11117-074), 5.0 mL/L MS vitamins stock solution (0.100 g/L nicotinic acid, 0.02 g/L thiamine HCL, 0.10 g/L pyridoxine HCL, and 0.40 g/L glycine brought to volume with polished D-I $H_2O$), 0.1 g/L myo-inositol, and 40.0 g/L sucrose (brought to volume with polished D-I $H_2O$ after adjusting pH to 5.6); and 6 g/L bacto-agar (added after bringing to volume with polished D-I $H_2O$), sterilized and cooled to 60° C.

Example 7

*Agrobacterium*-Mediated Transformation of Maize and Regeneration of Transgenic Plants For *Agrobacterium*-mediated transformation of maize with a nucleotide sequence encoding a cyclotide polypeptide of the invention, the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the polynucleotide construct to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is performed.

In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

Example 8

Transformation of Soybean Embryos

Culture Conditions

Soybean embryogenic suspension cultures (cv. Jack) are maintained in 35 ml liquid medium SB196 (see recipes below) on rotary shaker, 150 rpm, 26° C. with cool white fluorescent lights on 16:8 hr day/night photoperiod at light intensity of 60-85 µE/m2/s. Cultures are subcultured every 7 days to two weeks by inoculating approximately 35 mg of tissue into 35 ml of fresh liquid SB196 (the preferred subculture interval is every 7 days).

Soybean embryogenic suspension cultures are transformed with the plasmids and DNA fragments described in the following examples by the method of particle gun bombardment (Klein et al. (1987) *Nature*, 327:70).

Soybean Embryogenic Suspension Culture Initiation

Soybean cultures are initiated twice each month with 5-7 days between each initiation.

Pods with immature seeds from available soybean plants 45-55 days after planting are picked, removed from their shells and placed into a sterilized magenta box. The soybean seeds are sterilized by shaking them for 15 minutes in a 5% Clorox solution with 1 drop of ivory soap (95 ml of autoclaved distilled water plus 5 ml Clorox and 1 drop of soap). Mix well. Seeds are rinsed using 2 1-liter bottles of sterile distilled water and those less than 4 mm are placed on individual microscope slides. The small end of the seed is cut and the cotyledons pressed out of the seed coat. Cotyledons are transferred to plates containing SB1 medium (25-30 cotyledons per plate). Plates are wrapped with fiber tape and stored for 8 weeks. After this time secondary embryos are cut and placed into SB196 liquid media for 7 days.

Preparation of DNA for Bombardment

Either an intact plasmid or a DNA plasmid fragment containing the genes of interest and the selectable marker gene are used for bombardment. Plasmid DNA for bombardment are routinely prepared and purified using the method described in the Promega™ Protocols and Applications Guide, Second Edition (page 106). Fragments of the plasmids carrying a cyclotide protein coding sequence are obtained by gel isolation of double digested plasmids. In each case, 100 ug of plasmid DNA is digested in 0.5 ml of the specific enzyme mix that is appropriate for the plasmid of interest. The resulting DNA fragments are separated by gel electrophoresis on 1% SeaPlaque GTG agarose (BioWhitaker Molecular Applications) and the DNA fragments containing the cyclotide protein coding sequence are cut from the agarose gel. DNA is purified from the agarose using the GELase digesting enzyme following the manufacturer's protocol.

A 50 µl aliquot of sterile distilled water containing 3 mg of gold particles (3 mg gold) is added to 5 µl of a 1 µg/µl DNA solution (either intact plasmid or DNA fragment prepared as described above), 50 µl 2.5M $CaCl_2$ and 20 µl of 0.1 M spermidine. The mixture is shaken 3 min on level 3 of a vortex shaker and spun for 10 sec in a bench microfuge. After a wash with 400 µl 100% ethanol the pellet is suspended by sonication in 40 µl of 100% ethanol. Five µl of DNA suspension is dispensed to each flying disk of the Biolistic PDS1000/HE instrument disk. Each 5 µl aliquot contains approximately 0.375 mg gold per bombardment (i.e. per disk).

Tissue Preparation and Bombardment with DNA

Approximately 150-200 mg of 7 day old embryonic suspension cultures are placed in an empty, sterile 60×15 mm petri dish and the dish covered with plastic mesh. Tissue is bombarded 1 or 2 shots per plate with membrane rupture pressure set at 1100 PSI and the chamber evacuated to a vacuum of 27-28 inches of mercury. Tissue is placed approximately 3.5 inches from the retaining/stopping screen.

Selection of Transformed Embryos

Transformed embryos were selected either using hygromycin (when the hygromycin phosphotransferase, HPT, gene was used as the selectable marker) or chlorsulfuron (when the acetolactate synthase, ALS, gene was used as the selectable marker).

Hygromycin (HPT) Selection

Following bombardment, the tissue is placed into fresh SB196 media and cultured as described above. Six days post-bombardment, the SB196 is exchanged with fresh SB196 containing a selection agent of 30 mg/L hygromycin. The selection media is refreshed weekly. Four to six weeks post selection, green, transformed tissue may be observed growing from untransformed, necrotic embryogenic clusters. Isolated, green tissue is removed and inoculated into multiwell plates to generate new, clonally propagated, transformed embryogenic suspension cultures.

Chlorsulfuron (ALS) Selection

Following bombardment, the tissue is divided between 2 flasks with fresh SB196 media and cultured as described above. Six to seven days post-bombardment, the SB196 is exchanged with fresh SB196 containing selection agent of 100 ng/ml Chlorsulfuron. The selection media is refreshed weekly. Four to six weeks post selection, green, transformed tissue may be observed growing from untransformed, necrotic embryogenic clusters. Isolated, green tissue is removed and inoculated into multiwell plates containing SB196 to generate new, clonally propagated, transformed embryogenic suspension cultures.

Regeneration of Soybean Somatic Embryos into Plants

In order to obtain whole plants from embryogenic suspension cultures, the tissue must be regenerated.

Embryo Maturation

Embryos are cultured for 4-6 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 uE/m2s. After this time embryo clusters are removed to a solid agar media, SB166, for 1-2 weeks. Clusters are then subcultured to medium SB103 for 3 weeks. During this period, individual embryos can be removed from the clusters and screened for nematode and/or insect resistance.

Embryo Desiccation and Germination

Matured individual embryos are desiccated by placing them into an empty, small petri dish (35×10 mm) for approximately 4-7 days. The plates are sealed with fiber tape (creating a small humidity chamber). Desiccated embryos are planted into SB71-4 medium where they were left to germinate under the same culture conditions described above. Germinated plantlets are removed from germination medium and rinsed thoroughly with water and then planted in Redi-Earth in 24-cell pack tray, covered with clear plastic dome. After 2 weeks the dome is removed and plants hardened off for a further week. If plantlets looked hardy they are transplanted to 10" pot of Redi-Earth with up to 3 plantlets per pot. After 10 to 16 weeks, mature seeds are harvested, chipped and analyzed for proteins.

Media Recipes

| SB 196 - FN Lite liquid proliferation medium (per liter) | |
|---|---|
| MS FeEDTA - 100x Stock 1 | 10 ml |
| MS Sulfate - 100x Stock 2 | 10 ml |
| FN Lite Halides - 100x Stock 3 | 10 ml |
| FN Lite P, B, Mo - 100x Stock 4 | 10 ml |
| B5 vitamins (1 ml/L) | 1.0 ml |
| 2,4-D (10 mg/L final concentration) | 1.0 ml |
| KNO3 | 2.83 gm |
| (NH4)2SO4 | 0.463 gm |
| Asparagine | 1.0 gm |
| Sucrose (1%) | 10 gm |
| pH 5.8 | |

FN Lite Stock Solutions

| Stock # | | 1000 ml | 500 ml |
|---|---|---|---|
| 1 | MS Fe EDTA 100x Stock | | |
| | Na$_2$ EDTA* | 3.724 g | 1.862 g |
| | FeSO$_4$—7H$_2$O | 2.784 g | 1.392 g |
| 2 | MS Sulfate 100x stock | | |
| | MgSO$_4$—7H$_2$O | 37.0 g | 18.5 g |
| | MnSO$_4$—H$_2$O | 1.69 g | 0.845 g |
| | ZnSO$_4$—7H$_2$O | 0.86 g | 0.43 g |
| | CuSO$_4$—5H$_2$O | 0.0025 g | 0.00125 g |
| 3 | FN Lite Halides 100x Stock | | |
| | CaCl$_2$—2H$_2$O | 30.0 g | 15.0 g |
| | KI | 0.083 g | 0.0715 g |
| | CoCl$_2$—6H$_2$O | 0.0025 g | 0.00125 g |
| 4 | FN Lite P, B, Mo 100x Stock | | |
| | KH$_2$PO$_4$ | 18.5 g | 9.25 g |
| | H$_3$BO$_3$ | 0.62 g | 0.31 g |
| | Na$_2$MoO$_4$—2H$_2$O | 0.025 g | 0.0125 g |

*Add first, dissolve in dark bottle while stirring

SB1 solid medium (per liter) comprises: 1 pkg. MS salts (Gibco/BRL—Cat#11117-066); 1 ml B5 vitamins 1000× stock; 31.5 g sucrose; 2 ml 2,4-D (20 mg/L final concentration); pH 5.7; and, 8 g TC agar.

SB 166 solid medium (per liter) comprises: 1 pkg. MS salts (Gibco/BRL—Cat#11117-066); 1 ml B5 vitamins 1000× stock; 60 g maltose; 750 mg MgCl2 hexahydrate; 5 g activated charcoal; pH 5.7; and, 2 g gelrite.

SB 103 solid medium (per liter) comprises: 1 pkg. MS salts (Gibco/BRL—Cat#11117-066); 1 ml B5 vitamins 1000× stock; 60 g maltose; 750 mg MgCl2 hexahydrate; pH 5.7; and, 2 g gelrite.

SB 71-4 solid medium (per liter) comprises: 1 bottle Gamborg's B5 salts w/sucrose (Gibco/BRL—Cat#21153-036); pH 5.7; and, 5 g TC agar.

2,4-D stock is obtained premade from Phytotech cat #D 295—concentration is 1 mg/ml.

B5 Vitamins Stock (per 100 ml) which is stored in aliquots at −20 C comprises: 10 g myo-inositol; 100 mg nicotinic acid; 100 mg pyridoxine HCl; and, 1 g thiamine. If the solution does not dissolve quickly enough, apply a low level of heat via the hot stir plate. Chlorsulfuron Stock comprises 1 mg/ml in 0.01 N Ammonium Hydroxide All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the foregoing list of embodiments and appended claims. Although specific terms are employed herein, they are used in a generic and descriptive sense only and not for purposes of limitation.

That which is claimed:

1. An isolated polynucleotide comprising:
   (i) a nucleotide sequence selected from the group consisting of:
      (a) a nucleotide sequence encoding a polypeptide comprising the amino acid sequence of SEQ ID NO: 1; and
      (b) a nucleotide sequence encoding a polypeptide comprising an amino acid sequence having at least 94% sequence identity to the amino acid sequence of SEQ ID NO: 1, wherein said polypeptide has nematicidal and/or insecticidal activity; and
   (ii) a sequence that is 5' to the nucleotide sequence of (i), wherein the 5' sequence is selected from the group consisting of: SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, and SEQ ID NO: 25.

2. An expression cassette comprising the isolated polynucleotide of claim 1.

3. The expression cassette of claim 2, wherein said isolated polynucleotide is operably linked to a promoter that drives expression in a plant.

4. The isolated polynucleotide of claim 1, wherein the isolated polynucleotide further comprises:
   (iii) a sequence that is 3' to the nucleotide sequence of (i), wherein the 3' sequence is selected from the group consisting of: SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, SEQ ID NO: 169, SEQ ID NO: 171, SEQ ID NO: 173, SEQ ID NO: 175, SEQ ID NO: 177, SEQ ID NO: 179, SEQ ID NO: 181, SEQ ID NO: 183, SEQ ID NO: 185, SEQ ID NO: 187, SEQ ID NO: 189, SEQ ID NO: 191, SEQ ID NO: 193, and SEQ ID NO: 195.

5. An isolated polynucleotide comprising:
(i) a nucleotide sequence selected from the group consisting of:
   (a) a nucleotide sequence encoding a polypeptide comprising the amino acid sequence of SEQ ID NO: 1; and
   (b) a nucleotide sequence encoding a polypeptide comprising an amino acid sequence having at least 94% sequence identity to the amino acid sequence of SEQ ID NO: 1, wherein said polypeptide has nematicidal and/or insecticidal activity; and
(ii) a sequence that is 3' to the nucleotide sequence of (i), wherein the 3' sequence is selected from the group consisting of: SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, and SEQ ID NO: 25.

6. The isolated polynucleotide of claim 5, wherein the isolated polynucleotide further comprises:
(iii) a sequence that is 5' to the nucleotide sequence of (i), wherein the 5' sequence is selected from the group consisting of: SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167, SEQ ID NO: 169, SEQ ID NO: 171, SEQ ID NO: 173, SEQ ID NO: 175, SEQ ID NO: 177, SEQ ID NO: 179, SEQ ID NO: 181, SEQ ID NO: 183, SEQ ID NO: 185, SEQ ID NO: 187, SEQ ID NO: 189, SEQ ID NO: 191, SEQ ID NO: 193, and SEQ ID NO: 195.

7. An expression cassette comprising the isolated polynucleotide of claim 4, 5, or 6.

8. The expression cassette of claim 7, wherein said isolated polynucleotide is operably linked to a promoter that drives expression in a plant.

\* \* \* \* \*